United States Patent
Wang et al.

(10) Patent No.: US 10,722,160 B2
(45) Date of Patent: Jul. 28, 2020

(54) NON-INVASIVE AND WEARABLE CHEMICAL SENSORS AND BIOSENSORS

(71) Applicant: The Regents of the University of California, Oakland, CA (US)

(72) Inventors: Joseph Wang, San Diego, CA (US); Amay Jairaj Bandodkar, La Jolla, CA (US); Patrick Mercier, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 370 days.

(21) Appl. No.: 15/531,982

(22) PCT Filed: Dec. 3, 2015

(86) PCT No.: PCT/US2015/063836
§ 371 (c)(1),
(2) Date: May 31, 2017

(87) PCT Pub. No.: WO2016/090189
PCT Pub. Date: Jun. 9, 2016

(65) Prior Publication Data
US 2017/0325724 A1 Nov. 16, 2017

Related U.S. Application Data

(60) Provisional application No. 62/087,172, filed on Dec. 3, 2014, provisional application No. 62/112,608, filed on Feb. 5, 2015.

(51) Int. Cl.
*A61B 5/1486* (2006.01)
*A61B 5/00* (2006.01)
(Continued)

(52) U.S. Cl.
CPC ........ *A61B 5/1486* (2013.01); *A61B 5/14521* (2013.01); *A61B 5/14532* (2013.01);
(Continued)

(58) Field of Classification Search
None
See application file for complete search history.

(56) References Cited

U.S. PATENT DOCUMENTS 5,422,246 A   6/1995  Koopal et al.
6,120,460 A   9/2000  Abreu
(Continued)

FOREIGN PATENT DOCUMENTS

EP          1372602      4/2007
WO       2007040938 A1   4/2007
(Continued)

OTHER PUBLICATIONS

Zhu, et al. 2002. Planar Amperometric glucose sensor based on glucose oxidase immobilized by chitosan film on prussian blue layer. (Year: 2002).*

(Continued)

*Primary Examiner* — Michael R Bloch
(74) *Attorney, Agent, or Firm* — Perkins Coie LLP

(57) ABSTRACT

A non-invasive epidermal electrochemical sensor device includes an adhesive membrane; a flexible or stretchable substrate disposed over the adhesive membrane; and an anodic electrode assembly disposed over the flexible or stretchable substrate including an iontophoretic electrode. The device includes a cathodic electrode assembly disposed adjacent to the anodic electrode assembly over the flexible or stretchable substrate and includes an iontophoretic electrode. Either the cathodic electrode assembly or the anodic electrode assembly also includes a sensing electrode that includes a working electrode and at least one of a counter (Continued)

electrode or a reference electrode. The iontophoretic electrode in either the anodic electrode assembly or the cathodic electrode assembly that includes the sensing electrode is disposed on the substrate to at least partially encompass the working electrode and the at least one of the counter electrode or the reference electrode. The device includes an electrode interface assembly including independent electrically conductive contacts.

33 Claims, 50 Drawing Sheets

(51) Int. Cl.
*A61B 5/145* (2006.01)
*G01N 33/66* (2006.01)
(52) U.S. Cl.
CPC ........ *A61B 5/6833* (2013.01); *A61B 2562/00* (2013.01); *A61B 2562/0215* (2017.08); *G01N 33/66* (2013.01)

(56) References Cited

U.S. PATENT DOCUMENTS

| | | | |
|---|---|---|---|
| 6,465,091 B1 | 10/2002 | Ou-Yang | |
| 6,546,268 B1 | 4/2003 | Ishikawa et al. | |
| 6,587,705 B1 | 7/2003 | Kim et al. | |
| 2002/0004640 A1* | 1/2002 | Conn | A61B 5/1486 604/20 |
| 2002/0055704 A1 | 5/2002 | Scott et al. | |
| 2002/0072784 A1 | 6/2002 | Sheppard, Jr. et al. | |
| 2002/0105080 A1 | 8/2002 | Speakman | |
| 2002/0121438 A1 | 9/2002 | Saffell et al. | |
| 2003/0235817 A1* | 12/2003 | Bartkowiak | A61B 5/14532 435/5 |
| 2004/0262582 A1 | 12/2004 | Kirkor et al. | |
| 2006/0127964 A1 | 6/2006 | Ford et al. | |
| 2007/0078445 A1 | 4/2007 | Malloy | |
| 2008/0027369 A1 | 1/2008 | Carter et al. | |
| 2008/0114220 A1 | 5/2008 | Banet et al. | |
| 2008/0275327 A1 | 11/2008 | Faarbaek et al. | |
| 2009/0047550 A1 | 2/2009 | Kakuta et al. | |
| 2009/0084678 A1 | 4/2009 | Joshi et al. | |
| 2009/0101498 A1 | 4/2009 | Papadimitrakopoulos et al. | |
| 2009/0191616 A1 | 7/2009 | Lu et al. | |
| 2009/0242429 A1 | 10/2009 | Sitdikov et al. | |
| 2010/0137779 A1* | 6/2010 | Seitz | A61N 1/30 604/20 |
| 2010/0158788 A1 | 6/2010 | Kim et al. | |
| 2011/0140703 A1 | 6/2011 | Chiao et al. | |
| 2011/0275918 A1 | 11/2011 | Yamashita et al. | |
| 2011/0288388 A1 | 11/2011 | Shah et al. | |
| 2011/0293894 A1 | 12/2011 | Sato et al. | |
| 2011/0319787 A1 | 12/2011 | Lamoise et al. | |
| 2012/0018302 A1 | 1/2012 | Shiraki et al. | |
| 2012/0228137 A1 | 9/2012 | Cho et al. | |
| 2012/0277629 A1 | 11/2012 | Bernstein et al. | |
| 2013/0345597 A1 | 12/2013 | Hagino et al. | |
| 2014/0135679 A1 | 5/2014 | Mann et al. | |
| 2015/0126834 A1 | 5/2015 | Wang et al. | |
| 2015/0335288 A1* | 11/2015 | Toth | A61B 5/6833 600/373 |

FOREIGN PATENT DOCUMENTS

| | | |
|---|---|---|
| WO | 2010014959 A2 | 2/2010 |
| WO | 2010045247 A1 | 4/2010 |
| WO | 2011156095 A2 | 12/2011 |

OTHER PUBLICATIONS

PCT Application No. PCT/US2015/063836, International Search Report and Written Opinion, dated Feb. 12, 2016, 13 pages.

Amos, A.F. et al., "The Rising Global Burden of Diabetes and its Complications: Estimates and Projections to the Year 2010", Diabetic Med., 1997, 14, pp. S7-S85.

Bandodkar, A. J. et al., "Epidermal tattoo potentiometric sodium sensors with wireless signal transduction for continuous noninvasive sweat monitoring", Biosens. Bioelectron. 2014, 54, pp. 603-609.

Bandodkar, A. J. et al., "Non-invasive wearable electrochemical sensors: a review", Trends Biotechnol. 2014, 32, pp. 363-371.

Bandodkar, A. J. et al., "Tattoo-based potentiometric ion-selective sensors for epidermal pH monitoring", Analyst, 2013, 138, pp. 123-128.

Ching, C. T. S. et al., "A Mediated Glucose Biosensor Incorporated with Reverse Iontophoresis Function for Noninvasive Glucose Monitoring", Annals Biomed. Eng. 2010, vol. 38, No. 4, pp. 1548-1555.

Choleau, C. et al., "Calibration of a subcutaneous amperometric glucose sensor implanted for 7 days in diabetic patients Part 2. Superiority of the one-point calibration method", Biosens. Bioelectron. 2002, 17, pp. 647-654.

Gross, T. M. et al., "Performance Evaluation of the MiniMed Continuous Glucose Monitoring System During Patient Home Use", Diabetes Technol. Therapeutics, 2000, 2, pp. 49-56.

Jia, W. et al., "Electrochemical Tattoo Biosensors for Real-Time Noninvasive Lactate Monitoring in Human Perspiration", Anal. Chem. 2013,85, pp. 6553-6560.

Karyakin, A. A., "Prussian Blue and Its Analogues: Electrochemistry and Analytical Applicants", Electroanal. 2001, 13, No. 10, pp. 813-819.

Mccormick, C. et al., "Towards blood free measurement of glucose and potassium in humans using reverse iontophoresis", Sensors and Actuators B 166-167, 2012, pp. 593-600.

Mcgarraugh, G., "The Chemistry of Commercial Continuous Glucose Monitors", Diabetes Technol. Therapeutics 2009, 11, S17-S24.

Newman, J. D. et al., "Home blood glucose biosensors: a commercial perspective", Biosensors and Bioelectronics, 20, 2005, pp. 2435-2453.

Oliver, N. S. et al., "Glucose sensors: a review of current and emerging technology", Diabetic Medicine, 2009, 26, pp. 197-210.

Rebrin, K. et al., "Can Interstitial Glucose Assessment Replace Blood Glucose Measurements", Diabetes Technology & Therapeutics, vol. 2, No. 3, 2000, pp. 461-472.

Stout, P. J. et al., "A Novel Approach to Mitigating the Physiological Lag Between Blood and Interstitial Fluid Glucose Measurements", Diabetes Technology & Therapeutics, vol. 6, No. 5, 2004, pp. 635-644.

Sun, T. P. et al., "Carbon nanotube composites for glucose biosensor incorporated with reverse iontophoresis function for noninvasive glucose monitoring", Inter. J. Nanomed. 2010, 20, pp. 343-349.

Tanenberg, R. et al., "Use of the Continuous Glucose Monitoring System to Guide Thereapy in Patients with Insulin-Treated Diabetes: A Randomized Controlled Trial", Mayo Clin. Proc. 2004, 79, pp. 1521-1526.

Tierney, M. J. et al., "Electroanalysis of Glucose in Transcutaneously Extrated Samples", Electroanal. 2000, 12, pp. 666-671.

Vashist, S. K.., "Non-invasive glucose monitoring technology in diabetes management: A review", Anal. Chim. Acta 2012, 750, pp. 16-27.

Whiting, D. R. et al., "IDF Diabetes Atlas: Global estimates of theprevalence of diabetes for 2011 and 2030", Diabetes Res. Clin. Pract. 2011, 94, pp. 311-321.

Windmiller, J. R., et al., "Electrochemical sensing b ased on printable temporary transfer tattoos", Chem. Commun. 2012, 48, pp. 6794-6796.

Windmiller, J. R., et al., "Wearable Electrochemical Sensors and Biosensors: A Review", Electroanal. 2013, 25, No. 1, pp. 29-46.

Cheng, H. et al., "An analytical model of strain isolation for stretchable and flexible electronics", Appl. Phys. Lett. 98, 061902 (2011), 4 pages.

Chuang, M. C. et al. "Textile-based electrochemical sensing: effect of fabric substrate and detection of nitroaromatic explosives", Electroanal. 22, 2010, pp. 2511-2518.

(56) References Cited

OTHER PUBLICATIONS

Chuang, M.C. et al., "Flexible thick-film glucose bionsensor: Influence of mechanical bending on the performance", Talanta, 2010, 81, pp. 15-19.

Coyle, S. et al., "Smart nanotextiles: A review of materials and applications", MRS Bull. 32, May 2007, pp. 434-442.

Diamond, D. et al., "Wireless sensor networks and chemo-/biosensing", Chem. Rev. 108, 2008, pp. 652-679.

EPO, Extended European Search Report for European Patent Application 13827958.3; dated Dec. 18, 2015; 9 pages.

Gutowski, T. G. et al., "The elastic deformation of lubricated carbon fiber bundles: Comparison of theory and experiments", J. Compos. Mater. vol. 26, No. 16, 1992, pp. 2330-2347.

Kim, D. H.et al., "Epidermal Electronics", Science 333, 2011, pp. 838-843.

Ma, R. et al., A stretchable electrode array for non-invasive, skin-mounted measurement of electrocardiography (ECG), electromyography (EMG) and electroencephalography (EEG), 2nd Annual International Conference of the IEEE EMBS, 2010, pp. 6405-6408.

Malzahn, K.. et al., "Wearable electrochemical sensors for in situ analysis in marine environments" Analyst 136, 2011, pp. 2912-2917.

Matsuyama, H. et al., "Analysis of solute diffusion in poly(vinyl alcohol) hydrogel membrane",.J. Membrane Sci. 126, 1997, pp. 151-160.

Rogers, J.A. et al., "A curvy, stretchy future for electronics", PNAS, Jul. 7, 2009, vol. 106, No. 27, pp. 10875-10876.

Romolo, F. S. et al., "Identification of gunshot residue: A critical review", Forensic Sci. Int.119, 2001, pp. 195-211.

Tibbetts, G. C. et al., "Mechanical properties of vapor-grown carbon fiber composites with thermoplastic matrices", J. Mater. Res. 14, 1999, pp. 2871-2880.

USPTO, International Search Report and Written Opinion for PCT Application No. PCT/US2013/040671, dated Mar. 7, 2014, 11 pages.

Wang, "Electrochemical Glucose Biosensors", Chem. Rev., 108: 2008, pp. 814-825.

Wang, J. et al. "Screen-printed electrochemical hybridization biosensor for the detection of DNA sequences from the *Escherichia coli* pathogen", Electroanal., 1996, 9, pp. 395-398.

Wang, J. et al., "Bismuth-coated carbon electrodes for anodic stripping voltammetry" Anal.Chem. 72, 2000, pp. 3218-3222.

Wang, J. et al., "Miniaturized glucose sensors based on electrochemical codeposition of rhodium and glucose oxidase onto carbon-fiber electrodes", Anal.Chem. 64, 1992, pp. 456-459.

Wang, J., "Sol-gel materials for electrochemical biosensors", Anal. Chim. Acta, 399, 1999, pp. 21-27.

Windmiller, J.R. et al., "Bioelectronic system for the control and readout of enzyme logic gates", Sensor. Actuat. B 155, 2011, pp. 206-213.

Yang, Y. L. et al., "Thick-film textile-based amperometric sensors and biosensors" Analyst 135, 2010, pp. 1230-1234.

\* cited by examiner

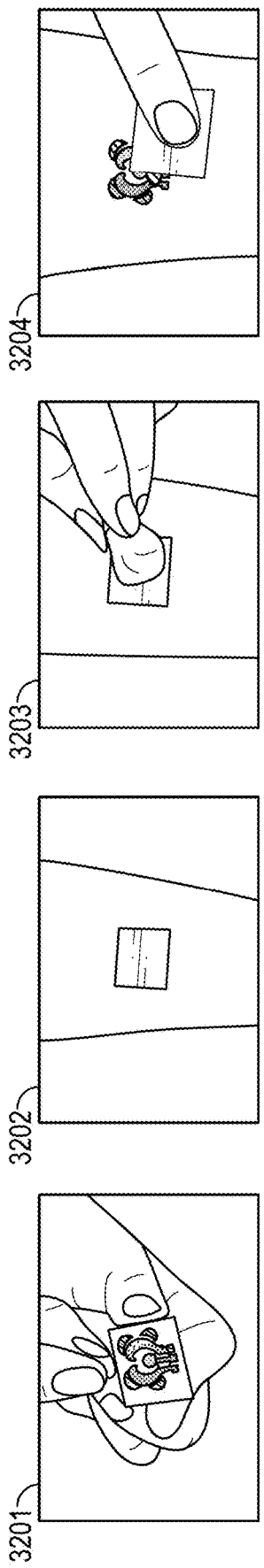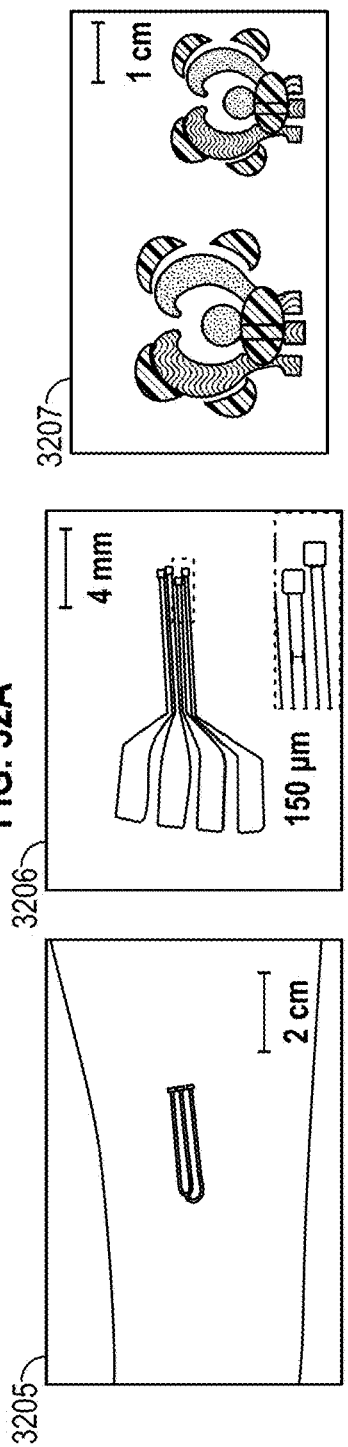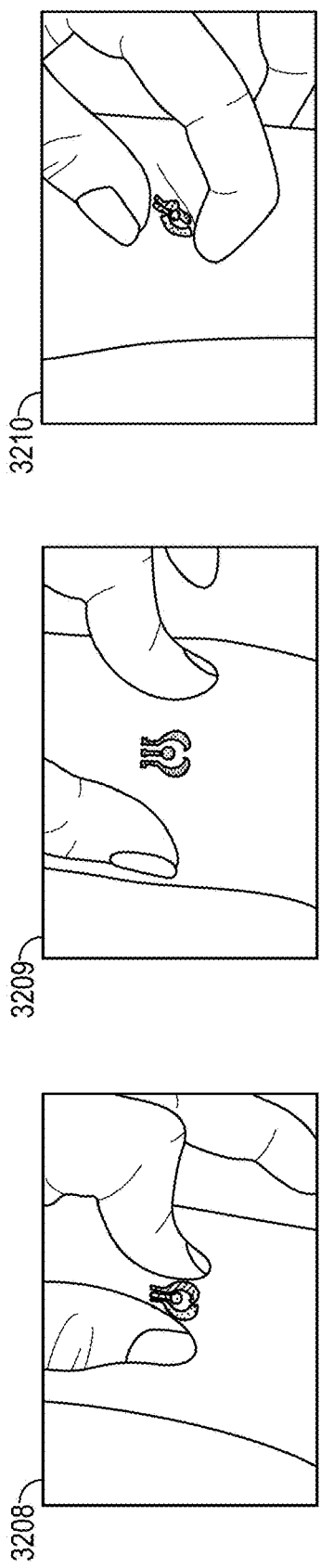
FIG. 32A
FIG. 32B
FIG. 32C

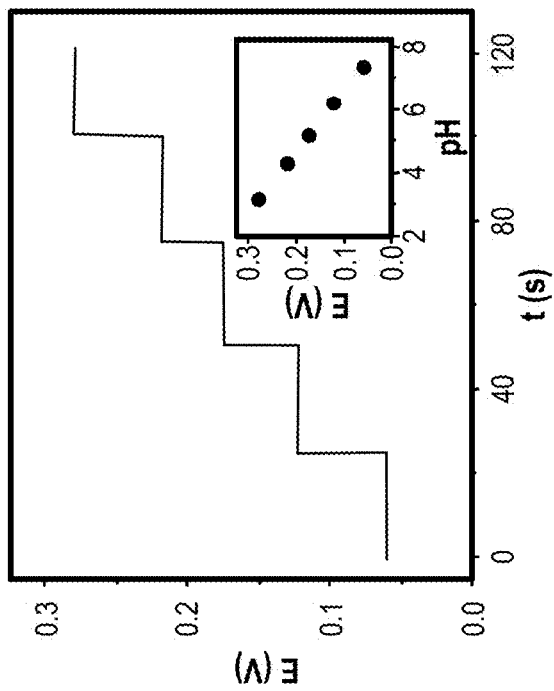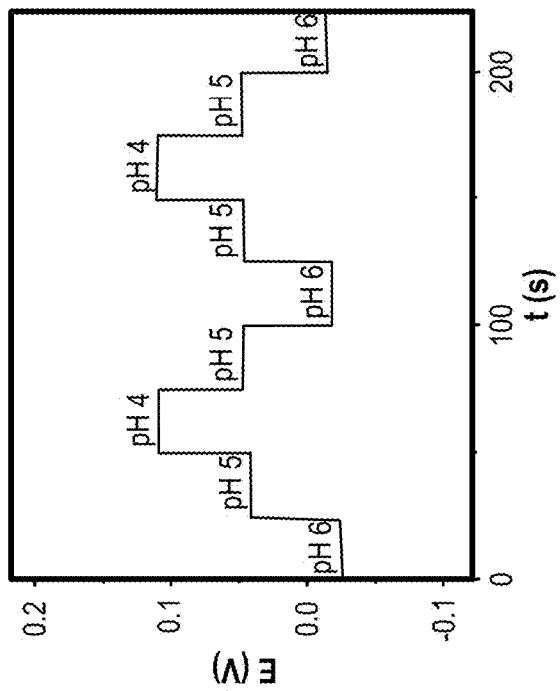
FIG. 37A
FIG. 37B
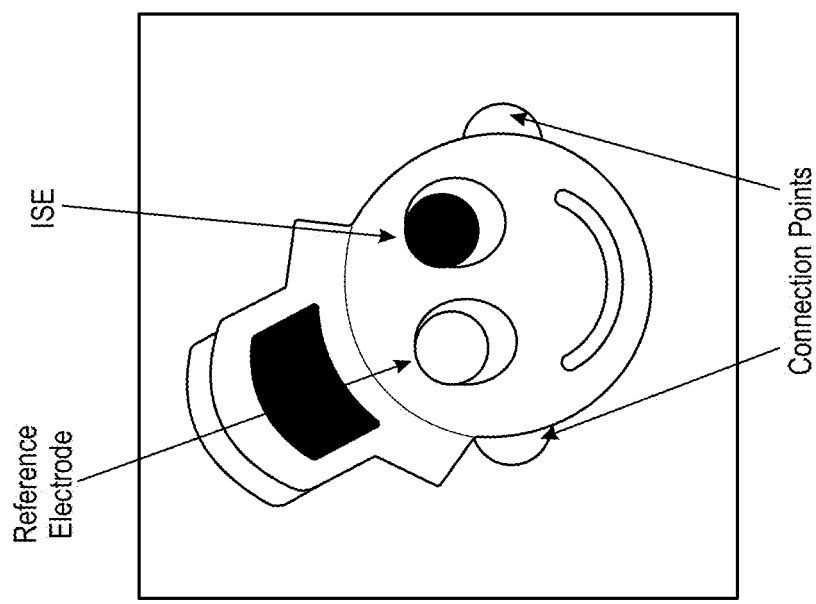
FIG. 36B

NON-INVASIVE AND WEARABLE CHEMICAL SENSORS AND BIOSENSORS

CROSS-REFERENCE TO RELATED APPLICATIONS

This patent document is a 35 USC § 371 National Stage application of International Application No. PCT/US2015/063836, entitled "NON-INVASIVE AND WEARABLE CHEMICAL SENSORS AND BIOSENSORS," filed on Dec. 3, 2015, which claims priorities to and benefits of U.S. Provisional Patent Application No. 62/087,172 entitled "NON-INVASIVE AND WEARABLE GLUCOSE MONITORING SENSORS" filed on Dec. 3, 2014, and U.S. Provisional Patent Application No. 62/112,608 entitled "SINGLE-USE NON-INVASIVE WEARABLE ELECTROCHEMICAL SENSORS BASED ON "PLACE-DETECT-DISPOSE" ("PDD") OPERATION" filed on Feb. 5, 2015. The entire content of the above patent applications are incorporated by reference as part of the disclosure of this patent document.

TECHNICAL FIELD

This patent document relates to electrochemical sensor devices, systems, and techniques.

BACKGROUND

Various medical conditions of patients need regular or frequent patient-operated testing to monitor conditions or well-being of patients. One example for such patient-operated testing is measuring the glucose level of diabetes patients. Diabetes (diabetes mellitus) is a metabolic disease associated with high blood sugar due to insufficient production of insulin by the body or inadequate response by cells to the insulin that is produced. There are three types of diabetes: type 1, type 2, and gestational diabetes. Type 1 diabetes is associated with the body's failure to produce insulin. Type 2 diabetes is associated with insulin resistance, in which cells fail to use insulin properly. The third form of diabetes is referred to as gestational diabetes, which can occur when pregnant women develop a high blood glucose level (e.g., even without a previous history of diabetes). Gestational diabetes can develop into type 2 diabetes, but often resolves after the pregnancy. Diabetes is widely-spread globally, affecting hundreds of millions of people, and is among the leading causes of deaths globally. Various medical conditions of patients need regular or frequent patient-operated testing to monitor conditions or well-being of patients. One example for such patient-operated testing is measuring the glucose level of a diabetes patients.

SUMMARY

Techniques, systems, and devices are disclosed for non-invasive and wearable biosensing or chemical monitoring, such as glucose monitoring. The disclosed technology enables monitoring in continuous or quasi-continuous mode through multiple measurements performed using the same sensor over a time period (longer than measured in minutes, e.g., a few hours to several days). A continuous chemical monitoring device can be obtained by selecting a hydrogel layer that allows fast transport of all the extracted chemical analyte to the sensor surface. The basic implementation of the disclosed technology is a single-use on-body electrochemical sensors for non-invasive detection of physiologically relevant chemicals. For example, the disclosed technology provides an economical and easy-to-use biosensor platform that allows a user to "place-detect-dispose" (PDD)' the sensor to obtain bioanalytical information for health and performance monitoring. However, the disclosed biosensor is reusable for multiple testing that allows for the continuous or quasi-continuous monitoring of a target analyte. Thus, the PPD application is described in this patent document as an exemplary use case and a variety of reusable protocols can be implemented to performing a target analyte monitoring over a period of time continuously or periodically. The disclosed technology can detect pre-selected chemicals in the skin interstitial fluid (ISF) or in sweat at a particular time to allow for non-invasive and easy measurements that can be carried out by the patients with ease without cutting or piercing skin or any body tissues of the patients. For example, the disclosed technology can be implemented as disposable, non-invasive electrochemical sensors to be conveniently carried by the patents at times of their choice, e.g., after a meal, such as for glucose testing, or after beverage consumption, such as for alcohol testing. For example, a user can apply an exemplary single-use electrochemical sensor device to a selected skin area such that the device then quantifies a target chemical analyte in a biological fluid, e.g., including an analyte in ISF that is non-invasively extracted from under the epidermal layer of the skin for external detection by the device. Thereafter, the user can remove the device from the skin.

The subject matter described in this patent document can be implemented in specific ways that provide one or more of the following features. The disclosed technology can be used for a variety of applications including digital/mobile health applications; its customizable consumable lends itself to a range of business models and services. For example, in applications of detecting chemicals in the ISF, an electrochemical sensor device includes a reverse iontophoretic electrode assembly that will first extract the ISF to the surface of the skin followed by electrochemical detection of the desired chemical analyte via electrochemical sensor electrodes of the device. In applications of detecting chemicals in the sweat, an iontophoretic electrode assembly is included into the device that will first induce localized sweating (in the vicinity of the device) by transdermally administering sweat-inducing drugs into the skin, followed by detection of the chemical analyte in the induced sweat via the electrochemical sensor electrodes. Also, for example, the device can be configured with visual designs that can be customized for the purpose of branding, aesthetics, user specification (user's own design), time/condition labeling etc.

In one aspect, a non-invasive epidermal electrochemical sensor device includes a flexible substrate including an electrically insulative material structured to adhere to skin of a user; an anodic electrode assembly and a cathodic electrode assembly each formed and separately arranged on the substrate and each including a working electrode, a counter/reference electrode, and a reverse iontophoretic electrode, in which the reverse iontophoretic electrode is structured on the substrate to at least partially encompass the working electrode and the counter/reference electrode and operable to apply an electric field to drive ion flow from interstitial fluid (ISF) toward the working electrode and the counter/reference electrode, and in which the working electrode includes a electrochemical transducer layer including a catalyst to selectively catalyze a corresponding analyte in the ISF to cause a reaction detectable at the anodic and cathodic electrode assemblies; and an electrode interface assembly comprising independent electrically conductive conduits formed on the substrate and electrically coupled to each of the working, counter/reference, and reverse iontophoretic electrodes of the anodic electrode assembly and the cathodic electrode assembly. The non-invasive epidermal electrochemical sensor device, when attached to the skin and electrically coupled to one or more electrical circuits via the electrode interface assembly, the device is operable to detect the analyte from the ISF in a local environment of the skin.

The subject matter described in this patent document can be implemented in specific ways that provide one or more of the following features. In some aspects, a glucose monitoring device of the disclosed technology includes an all-printed temporary tattoo-based glucose sensor for non-invasive glycemic monitoring. The exemplary flexible tattoo-based epidermal diagnostic device uses reverse iontophoretic extraction of interstitial glucose and an enzyme-based amperometric biosensor. Exemplary in vitro implementations of the flexible tattoo-based epidermal glucose monitoring device produced exemplary data showing the tattoo sensor's linear response towards physiologically relevant glucose levels with negligible interferences from common co-existing electroactive species. The disclosed iontophoretic-biosensing tattoo sensor technology platform can be applied on human subjects, e.g., by attaching to the subject's skin, to monitor variations in glycemic levels due to food consumption. Also, for example, exemplary implementations to compare performance of the disclosed non-invasive and wearable glucose monitoring technology with conventional glucose meters were performed, in which the exemplary results included correlation of the disclosed sensor response with that of a commercial glucose meter, which underscores the benefits of the exemplary tattoo sensor to detect glucose levels in a non-invasive fashion. The exemplary implementations included control on-body experiments that demonstrated the importance of the reverse iontophoresis operation and validate the sensor specificity. The disclosed tattoo-based iontophoresis-sensor platform holds considerable promise for efficient diabetes management and can be extended towards non-invasive monitoring of other physiologically relevant analytes present in the interstitial fluid.

In one aspect, a non-invasive epidermal biosensor device includes a flexible substrate including an electrically insulative material structured to adhere to skin of a user; an anodic electrode assembly and a cathodic electrode assembly disposed on the flexible substrate, in which each of the anodic and cathodic electrode assemblies includes (i) electrochemical sensing electrodes including a working electrode and a second electrode and being configured to form an electrochemical sensor, and (ii) an iontophoretic electrode disposed on the flexible substrate to at least partially encompass an area occupied by the working electrode to apply an electric field to a skin area of the user including a tissue area underneath the skin surface to drive ions flow in interstitial fluid (ISF) underneath the skin surface toward the electrochemical sensing electrodes, in which the iontophoretic electrodes are configured not part of the electrochemical sensing electrodes, and in which the working electrode of the cathode and/or the anode electrode assembly includes a electrochemical transducer layer including a catalyst to selectively catalyze a corresponding analyte to cause a reaction detectable at the electrochemical sensing electrodes of the anodic and cathodic electrode assemblies; a layer disposed over the iontophoretic electrodes of the anodic and cathodic electrode assemblies to provide an electrically conductive medium between the iontophoretic electrodes and the skin for the electric field applied; and an electrode interface assembly comprising independent electrically conductive conduits disposed on the flexible substrate that are electrically coupled to the anodic and cathodic electrode assemblies to electrically couple the anodic and cathodic electrode assemblies to one or more external electrical circuits to electrically energize the electrochemical sensing electrodes and to separately electrically energize the iontophoretic electrode. When attached to the skin, the device is operable to detect the analyte from the ISF in a local environment of the skin.

Implementations of the device can include one or more of the following features. In some implementations, for example, the analyte is glucose, and the catalyst can include glucose oxidase (GOx) or glucose dehydrogenase (GDH). For example, the electrochemical transducer layer can include a solution of GOx or GDH and a solution of a biopolymer, for example, chitosan to immobilize the GOx or GDH in the electrochemical transducer layer. For example, the device is operable to extract the glucose from the ISF in a region containing the electrochemical sensing electrodes at the cathodic electrode assembly to cause the working electrode of the cathodic electrode assembly to react with (e.g., electrochemically oxidize) the glucose via the GOx or GDH for selective glucose detection. In some implementations, for example, the flexible substrate includes paper. In some implementations, for example, the flexible substrate includes plastic. In some implementations, for example, the substrate includes fabric. In some implementations, for example, the flexible or stretchable substrate includes at least one of silicone or polyurethane. In some implementations, for example, the second electrode of the electrochemical sensing electrodes and the iontophoretic electrode are structured as Ag/AgCl electrodes. In some implementations, for example, the electrochemical sensor includes a third electrochemical sensing electrode, in which the third electrode can be of same material or of different material as compared to the working electrode. For example, in a two electrode configuration of the electrochemical sensor, the second electrode is operable as a reference and counter electrode. Also, for example, in a three electrode configuration of the electrochemical sensor, the second electrode is operable as a reference electrode, and the third electrode is operable as a counter electrode. In some implementations, for example, the working electrode includes a hydrogen peroxide sensing transducer, such as Prussian Blue. In some implementations, for example, the working electrode includes metal. In some implementations, for example, the working electrode includes carbon. In some implementations, for example, the working electrode includes mediators for efficient electron transfer between enzyme and electrode. In some implementations, for example, the iontophoretic electrode is arranged to extract interstitial fluid (ISF) in a region within 10 mm or less of the working electrode. In some implementations, for example, the device further includes a first insulating layer formed over the anodic electrode assembly and a second insulating layer formed over the cathodic electrode assembly, the first and second insulating layers to confine electrode and contact areas of the device. In some implementations, for example, the layer includes a hydrogel layer. For example, the layer (e.g., the hydrogel layer) can also be coated over at least some of the electrochemical sensing electrodes (e.g., the working electrode) of the anodic and cathodic electrode assemblies to assist the flow of the extracted ISF to the electrochemical sensor.

In one aspect, a method of non-invasively detecting an analyte using an non-invasive electrochemical sensor includes attaching an electrochemical sensor device to a user's skin, in which the electrochemical sensor device includes: (i) a flexible or stretchable and electrically insulative substrate, (ii) an anode electrode assembly and a cathode electrode assembly separately disposed on the substrate and each including an iontophoretic electrode and two or more electrochemical sensor electrodes, which include a working electrode, in which the iontophoretic electrode is structured on the substrate to at least partially encompass the working electrode, and in which the working electrode of the cathode and/or anode electrode assembly includes a electrochemical transducer layer including a catalyst to selectively catalyze a corresponding analyte to cause a reaction detectable at the electrochemical sensor electrodes of the anode and cathode electrode assemblies, and (iii) hydrogel layer formed over the iontophoretic electrodes of the anode and cathode electrode assemblies to provide an electrically conductive medium between the iontophoretic electrodes and the skin. The attaching includes placing the anode and the cathode electrode assemblies in contact with the skin, in which the substrate of the electrochemical sensor device adheres to the skin. The method includes extracting interstitial fluid (ISF) containing the analyte onto the skin by applying an electric field from the iontophoretic electrodes of the anode and the cathode electrode assemblies to drive ion flow of the ISF under an epidermal layer of the skin toward the electrochemical sensor electrodes. The method includes providing an electrical potential at the working electrode to cause a redox reaction with the analyte in the extracted ISF that produces an electrical signal. And, the method includes detecting the electrical signal at the electrochemical sensor electrodes, in which the electrical signal is associated with a parameter of the analyte, and in which the detecting includes the oxidation or reduction of the analyte by the catalyst (for example, enzyme) to generate electrical signal.

Implementations of the method can include one or more of the following features. In some implementations, for example, the analyte is glucose, and the catalyst can include glucose oxidase (GOx) or glucose dehydrogenase (GDH). In some implementations, for example, the method further includes processing the detected electrical signal to determine a concentration level of the glucose in the ISF.

In one aspect, a non-invasive epidermal biosensor device to detect an analyte in a biological fluid includes a flexible or stretchable substrate including an electrically insulative material structured to adhere to skin of a user; an anodic electrode assembly and a cathodic electrode assembly disposed on the flexible substrate, in which each of the anodic and cathodic electrode assemblies includes (i) electrochemical sensing electrodes including a working electrode and a second electrode being configured to form an electrochemical sensor, and (ii) an iontophoretic electrode disposed on the flexible substrate to at least partially encompass an area occupied by the working electrode to apply an electric field into the skin, in which the iontophoretic electrodes are configured not part of the electrochemical sensing electrodes, and in which the working electrode of the cathode and/or anode electrode assembly includes a electrochemical transducer layer including a chemical agent to selectively catalyze or react with a corresponding analyte to cause a reaction detectable at the electrochemical sensing electrodes of the anodic and cathodic electrode assemblies; a layer disposed over the iontophoretic electrodes of the anodic and cathodic electrode assemblies to provide an electrically conductive medium between the iontophoretic electrodes and the skin for the electric field applied, in which the layer of the anodic electrode assembly contains a chemical compound capable of inducing perspiration of the skin, such that, when the electric field is applied by the iontophoretic electrodes, the electric field causes the release of the chemical compound from the layer into the skin; and an electrode interface assembly comprising independent electrically conductive conduits disposed on the flexible substrate that are electrically coupled to the anodic and cathodic electrode assemblies to electrically couple the anodic and cathodic electrode assemblies to one or more external electrical circuits to electrically energize the electrochemical sensing electrodes and to separately electrically energize the iontophoretic electrode. When attached to the skin, the device is operable to detect the analyte in sweat in a local environment of the skin that was induced by the device.

Implementations of the device can include one or more of the following features. In some implementations, for example, the chemical compound can include pilocarpine. In some implementations, for example, the analyte includes alcohol or an electrolyte. In some implementations, for example, the chemical agent includes sodium nitrate. In some implementations, for example, the flexible substrate includes paper. In some implementations, for example, the substrate includes fabric. In some implementations, for example, the flexible or stretchable substrate includes at least one of silicone or polyurethane. In some implementations, for example, the flexible substrate includes plastic. In some implementations, for example, the second electrode of the electrochemical sensing electrodes and the iontophoretic electrode are structured as Ag/AgCl electrodes. In some implementations, for example, the electrochemical sensor includes a third electrochemical sensing electrode, in which the third electrode can be of same material or of different material as compared to the working electrode. For example, in a two electrode configuration of the electrochemical sensor, the second electrode is operable as a reference and counter electrode. Also, for example, in a three electrode configuration of the electrochemical sensor, the second electrode is operable as a reference electrode, and the third electrode is operable as a counter electrode. In some implementations, for example, the working electrode includes a hydrogen peroxide sensing transducer, such as Prussian Blue. In some implementations, for example, the device further includes a first insulating layer formed over the anodic electrode assembly and a second insulating layer formed over the cathodic electrode assembly, the first and second insulating layers to confine electrode and contact areas of the device. In some implementations, for example, the layer includes a hydrogel layer. For example, the layer (e.g., the hydrogel layer) can also be disposed over the at least some of the electrochemical sensing electrodes (e.g., the working electrode) of the anodic and cathodic electrode assemblies to assist the flow of the extracted ISF to the electrochemical sensor.

In one aspect, a method of non-invasively detecting an analyte in a biological fluid using an non-invasive electrochemical sensor includes attaching an electrochemical sensor device to a user's skin, in which electrochemical sensor device includes: (i) a flexible or stretchable and electrically insulative substrate, (ii) an anode electrode assembly and a cathode electrode assembly separately disposed on the substrate and each including an iontophoretic electrode and two or more electrochemical sensor electrodes, which include a working electrode, in which the iontophoretic electrode is structured on the substrate to at least partially encompass the working electrode, and in which the working electrode of the cathode and/or anode electrode assembly includes a electrochemical transducer layer including a chemical agent to selectively catalyze or react with a corresponding analyte to cause a reaction detectable at the electrochemical sensor electrodes of the anode and cathode electrode assemblies, and (iii) hydrogel layer formed over the iontophoretic electrodes of the anode and cathode electrode assemblies to provide an electrically conductive medium between the iontophoretic electrodes and the skin. The attaching includes placing the anode and the cathode electrode assemblies in contact with the skin, in which the substrate of the electrochemical sensor device adheres to the skin. The method includes applying an electric field from the iontophoretic electrodes of the anode and the cathode electrode assemblies to cause the release of the chemical compound from the hydrogel layer into the skin to induce perspiration onto the skin containing the analyte. The method includes providing an electrical potential at the working electrode to cause a redox reaction with the analyte in the perspiration on the skin that produces an electrical signal. And, the method includes detecting the electrical signal at the electrochemical sensor electrodes, in which the electrical signal is associated with a parameter of the analyte.

Implementations of the method can include one or more of the following features. In some implementations, for example, the detecting includes releasing the catalyst corresponding to the analyte into the local environment to catalytically or meditatively participate in the redox reaction. In some implementations, for example, the chemical compound includes pilocarpine, and the analyte includes alcohol or an electrolyte. In some implementations, for example, the method further includes processing the detected electrical signal to determine a concentration level of the alcohol or the electrolyte in the perspiration.

In one aspect, a non-invasive epidermal biosensor device includes a flexible substrate to adhere to skin of a user; an iontophoretic electrode assembly on the flexible substrate to apply an electric field to a skin area of the user including a tissue area underneath the skin surface to extract interstitial fluid (ISF) from underneath the skin surface outward from the skin; an electrochemical sensor comprising an anodic electrode assembly and a cathodic electrode assembly on the flexible substrate to sense an electrical signal from an electrochemical reaction involving an analyte in the extracted ISF; a layer disposed over the iontophoretic electrodes to provide an electrically conductive medium between the iontophoretic electrodes and the skin for the electric field applied; and an electrode interface assembly comprising independent electrically conductive conduits on the flexible substrate that electrically couple the anodic and cathodic electrode assemblies of the electrochemical sensor and the iontophoretic electrode assembly to one or more external electrical circuits, respectively, to electrically energize the electrochemical sensing electrodes and to separately electrically energize the iontophoretic electrode. When attached to the skin, the device is operable to detect the analyte from the ISF in a local environment of the skin.

Implementations of the device can include one or more of the following features. In some implementations, for example, each of the anodic and cathodic electrode assemblies includes electrochemical sensing electrodes including a working electrode and a second electrode. In some implementations, for example, the electrochemical sensor electrodes include a third electrode, in which the third electrode can be of same material or of different material as compared to the working electrode. For example, in a two electrode configuration of the electrochemical sensing electrodes, the second electrode is operable as a reference and counter electrode. Also, for example, in a three electrode configuration of the electrochemical sensing electrodes, the second electrode is operable as a reference electrode, and the third electrode is operable as a counter electrode. In some implementations, for example, the iontophoretic electrode assembly is disposed on the flexible substrate to at least partially encompass an area occupied by the working electrode. In some implementations, for example, the working electrode of the cathode and/or anode electrode assembly includes a electrochemical transducer layer including a catalyst to selectively catalyze a corresponding analyte to cause a reaction detectable at the electrochemical sensor. In some implementations, for example, the analyte includes glucose, and the catalyst includes glucose oxidase (GOx). In some implementations, for example, the electrochemical transducer layer includes a solution of GOx and a solution of chitosan to immobilize the GOx in the electrochemical transducer layer. In some implementations, for example, the device is operable to extract the glucose from the ISF in a region containing the electrochemical sensing electrodes at the cathodic electrode assembly to cause the working electrode of the cathodic electrode assembly to modify (e.g., electrochemically oxidize) the glucose via the GOx for selective glucose detection. In implementations, for example, the iontophoretic electrode assembly is configured to not be part of the electrochemical sensor. In some implementations, for example, the device further includes a first insulating layer formed over the anodic electrode assembly and a second insulating layer formed over the cathodic electrode assembly, the first and second insulating layers to confine electrode and contact areas of the device. In some implementations, for example, the layer includes a hydrogel layer. For example, the layer (e.g., the hydrogel layer) can also be disposed over the at least some of the electrochemical sensing electrodes (e.g., the working electrode) of the anodic and cathodic electrode assemblies to assist the flow of the extracted ISF to the electrochemical sensor. In some implementations, for example, the flexible substrate includes paper, fabric, silicone, or polyurethane.

BRIEF DESCRIPTION OF THE DRAWINGS

FIG. 32A shows images for transferring an exemplary epidermal electrochemical sensor device, e.g., such as the exemplary device shown in the images, on a user's skin.

FIG. 32B shows images of several representative design permutations transferred onto the epidermis.

FIG. 32C shows images that validate the structural resiliency of the exemplary T3 sensors to extreme mechanical deformations, e.g., in which various strain permutations were applied to the sensors.

FIG. 36B shows an image of an exemplary ISE tattoo sensor including two electrodes, e.g., including an ISE and a reference electrode, and connection points that can interface with a voltmeter, for example, via electrically conductive conduits.

FIG. 37A shows a data plot of the potential-time response of an exemplary ISE tattoo sensor for decreasing pH levels and an inset plot of electrical potential versus pH, e.g., using the standard McIlvaine's buffers.

FIG. 37B shows a data plot of the potential-time response of the exemplary ISE tattoo sensors, which demonstrates the reproducibility of the sensors in response to large pH fluctuations.

DETAILED DESCRIPTION

Figure 1B:
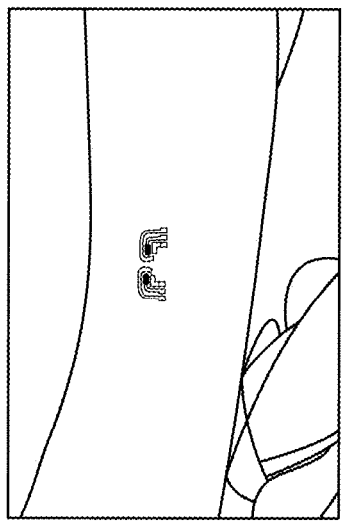
FIG. 1B shows a photograph of an exemplary iontophoretic-sensing tattoo device applied to a human subject.

Several diseases and disorders require patients to continuously monitor certain analytes associated with the disease on a continuous basis, e.g., such as multiple times per day. Diabetes is one of the most widely spread modern lifestyle diseases affecting hundreds of millions of people and is among the leading causes of deaths globally. Patients with diabetes must frequent monitor their glucose levels in order to manage the disease and avoid its associated problems, which can be severe and deadly.

Extensive research and development of analyte monitoring devices has evolved over the past few decades, which has led to the introduction and widespread use of self-testing blood glucose meters. However, such self-testing methods rely on inconvenient and painful blood sampling from the finger tip that compromises the patient's compliance. Furthermore, it requires active patient participation and this 'patient involvement' is a major factor affecting optimal disease management.

The present self-testing and self-monitoring blood glucose meter market relies on painful finger stick processes to draw blood samples followed by amperometric detection of glucose. While these finger stick-blood drawing technologies can be highly accurate in detecting glycemic levels in blood, the painful finger pricking is a major drawback. The need for active patient participation can lead to compromised diabetes management. For example, such finger stick (needle) devices have been attributed to patient noncompliance, particularly among neonatals, children, elderlies, hemophobics and trypanophobics patients. Because it can be hard for users to take blood samples, it is of great interest to develop new ways to obtain blood samples without a skin puncture.

Some enzyme-based micro-needle sensors inserted under the skin to measure chemical analytes in tissue fluid have been introduced in the markets to address these limitations. These micro-needle sensors are 'minimally' invasive, as they include needles that pierce the human skin to detect glucose levels in the interstitial fluid (ISF). These minimally invasive sensing methods are based on the correlation between chemical concentration in the ISF and in blood. Yet, these minimally invasive devices too face limitations, for example, biofouling, finger stick validation, and microbial infection. There have been several prototypes of non-invasive glucose monitoring systems to overcome such challenges. However, low specificity towards glucose and skin irritation has resulted in the withdrawal of some of these non-invasive devices from the market.

Techniques, systems, and devices are described for non-invasive wearable electrochemical sensors for detection of physiologically relevant chemicals for health and performance monitoring. The monitoring can occur in continuous or quasi-continuous mode through multiple measurements performed using the same sensor over a time period (longer than measured in minutes, e.g., a few hours to several days). A continuous chemical monitoring device can be obtained by selecting a hydrogel layer that allows fast transport of all the extracted chemical analyte to the sensor surface. Ideal hydrogels can be prepared by using polymers belong to the family of agarose, polyvinyl alcohol, acrylates, polyurethane, polyethylene glycol, etc. A combination of the above polymers can also be utilized to achieve the desired hydrogels. The hydrogels can be stabilized (to avoid drying) by incorporating humectants, such as, glycerol, glycols, sugar polyols. By playing with the ratio of the above components, the porosity of the hydrogel can be varied, thus manipulating the transport speed of the analyte.

In some implementations, a control working electrode can be incorporated into the device to reduce the effect of interference and obtain highly reliable data. The additional working electrode is not functionalized with the receptor (e.g.: enzyme) but has all the other components. This additional electrode can be placed close to the receptor functionalized working electrode. Data can be recorded for both these electrodes simultaneously and compared to obtain interference-free signal (Signal from control working electrode is subtracted from receptor-functionalized electrode).

The transport speed in the ideal hydrogel can depend on a number of factors including hydrogel porosity, iontophoresis current, etc. An ideal hydrogel remains hydrated for at least a week under ambient conditions and allows rapid mass transport, thus reducing the time required for iontophoresis and detection to a few minutes (<5 min). Furthermore, the high mass transport speed towards the working electrode allows rapid detection and consumption of most of the extracted analyte to obtain a analyte-free hydrogel layer, ready for the next iontophoresis-detection cycle without any memory effect (sensor response being affected by the analyte extracted during previous iontophoretic-detection cycle). A rough estimate for fast analyte transport that allows the analyte to move quickly from the skin to the electrode surface can be approximately 0.1 mm/s. The higher the speed, the faster the transport and the better the result.

In some implementations, the hydrogel can be optimized to limit biofouling and enhance sensor stability. For example, the hydrogel can also incorporate anti-fouling, bactericidal and anti-fungal chemical agents widely used in the wound dressing industry.

For example, the disclosed technology can be implemented as devices, systems and methods for a wearable and non-invasive glucose sensor for continuous monitoring of glucose levels for efficient diabetes management. In some aspects, the wearable glucose sensor device includes a reverse iontophoretic-amperometric hybrid platform on diverse wearable substrates to obtain rapid and sensitive glucose response, in which glucose is extracted from the ISF to the skin surface by passing a low current through the human skin followed by detection of the extracted glucose using a highly selective amperometric sensor. For example, in some embodiments, the wearable substrates include temporary tattoo paper and stretchable elastomeric membranes that attach to the skin for continuous glucose monitoring without the need for blood sampling.

The present electrochemical sensor technology includes single-use 'place-detect-dispose' (PDD) on-body sensors for non-invasive and painless detection of particular analytes associated with disease or health performance metrics. In some aspects, the single-use mode of the disclosed wearable electrochemical sensors can be employed on a device patch that can be fabricated or integrated on various substrates, e.g., including, but not limited to, paper, fabric, bendable and/or stretchable plastics or stretchable elastomeric membranes. Exemplary single-use wearable electrochemical sensor devices of the present technology can be fabricated using variety of techniques, e.g., including, but not limited to, printing processes such as screen printing, roll-to-roll printing, ink-jet printing, and/or lithographic techniques. The present technology can provide a pain-free single-use non-invasive test as an alternative to single-use strips used for detecting chemicals in blood.

Some implementations of the wearable electrochemical sensor devices can be used for detecting chemicals in the ISF. In such applications, for example, an electrochemical sensor device includes a reverse iontophoretic electrode assembly that will first extract the ISF to the surface of the skin followed by electrochemical detection of the desired chemical analyte via electrochemical sensor electrodes of the device. Other implementations of the wearable electrochemical sensor devices can be used for detecting chemicals in a user's biological fluid, such as sweat. In such applications, for example, the electrochemical sensor device includes an iontophoretic electrode assembly that will first induce localized sweating (in the vicinity of the electrochemical electrodes platform the device) by transdermally administering sweat-inducing drugs into the skin, followed by detection of the chemical analyte in the induced sweat via the electrochemical sensor electrodes.

The disclosed wearable electrochemical sensor devices and techniques can be used for diabetes management by providing a non-invasive highly selective single-use pain-free glucose monitoring platform, e.g., as an alternative to the painful strip-based glucose monitors. The disclosed technology can also be used for detecting and analyzing other blood analytes, for example, such as for non-invasive detection of alcohol (e.g., in which a test can be utilized by the user in car or bar before driving), lactate (e.g., in sport activity) or urea (e.g., for kidney patients), among others.

In one exemplary embodiment, a non-invasive electrochemical sensor device of the disclosed technology includes an anodic and a cathodic electrode contingent. Each contingent includes an electrochemical sensor electrode assembly including working electrode, a counter and/or reference electrode, and an iontophoresis electrode. The iontophoretic electrodes are configured to not be part of the electrochemical sensor electrode assembly. The iontophoretic electrodes operate independently from the electrochemical sensor electrode assembly. The iontophoretic electrodes are utilized for extraction of ISF to the surface of the skin or for administrating sweat-inducing drug for generating localized perspiration. The working, and counter and/or reference electrodes together constitute the electrochemical sensor electrode assembly that is utilized for sensitive chemical detection. In implementations of a two electrode configuration of the electrochemical sensor, for example, in addition to the working electrode, the second electrode is operable as a reference and counter electrode. In implementations of a three electrode configuration of the electrochemical sensor, for example, in addition to the working electrode, one electrode is operable as a reference electrode, and the other electrode is operable as a counter electrode. In some embodiments, for example, the working electrode of the cathode and/or the anode is modified with specific receptors like enzyme, ionophores and/or other reagents for achieving selective detection of the desired chemical analyte. In some implementations, for example, the anodic and cathodic contingent can be coated with a biocompatible hydrogel layer, e.g., covering the iontophoretic electrodes, or covering the iontophoretic electrode and at least some of the electrochemical sensor electrodes. For example, the biocompatible and conductive hydrogel layer can be disposed over the electrodes of the anodic and cathodic contingent to assist the flow of the extracted ISF to the electrochemical sensor. In some implementations, for example, the hydrogel layer can be loaded with specific chemicals agents (e.g., including FDA approved chemical agents) to enhance ISF extraction at low iontophoretic currents (in case of chemical detection in ISF) or with sweat-inducing drugs for localized sweating (in case of chemical detection in sweat).

The non-invasive electrochemical sensor device, when attached to the skin and electrically coupled to one or more electrical circuits or electronic devices, is operable to detect the chemical analyte from the extracted ISF or the sweat induced to the outer or local environment of the skin. For example, the non-invasive electrochemical sensor device can include an electrode interface assembly comprising individual or independent electrically conductive conduits disposed on the flexible substrate that are electrically coupled to the anodic and cathodic electrode assemblies. The flexible substrate can include bendable and/or stretchable properties. The individual or independent conduits are configured to electrically couple the electrochemical sensor electrodes of the anodic and cathodic electrode assemblies and the iontophoretic electrodes to the external electrical circuits or electronic devices, which are able to electrically energize the electrochemical sensing electrodes and to separately electrically energize the iontophoretic electrode for their respective operations.

In some implementations for alcohol detection, a three electrode system for the electrochemical sensor electrode assembly is preferred. Whereas for glucose detection, the electrochemical sensor electrode assembly may include a two electrode system (e.g., working electrode and counter/reference electrode) because the current measured as a function of glucose concentration is relatively low, such that the two electrode system is sufficient to detect glucose. For example, in case of alcohol detection, the concentration of alcohol can be relatively high in the biofluid (e.g., sweat), and hence the current measured is higher, and thereby a three electrode system can be utilized.

Figure 1A:
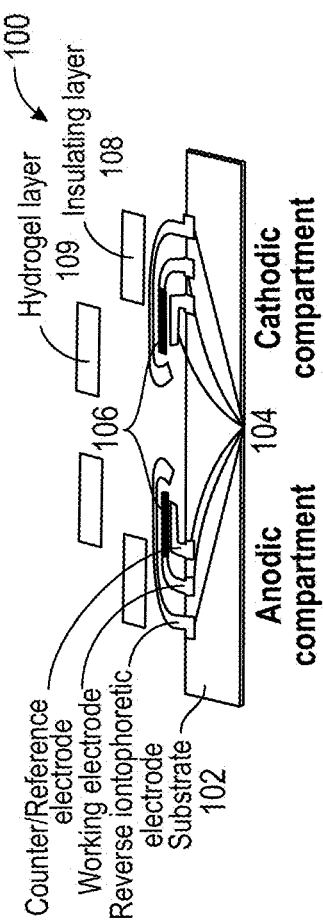
FIG. 1A shows a schematic illustration of an exemplary wearable electrochemical sensor platform for non-invasive analyte sensing.
Figure 1C:
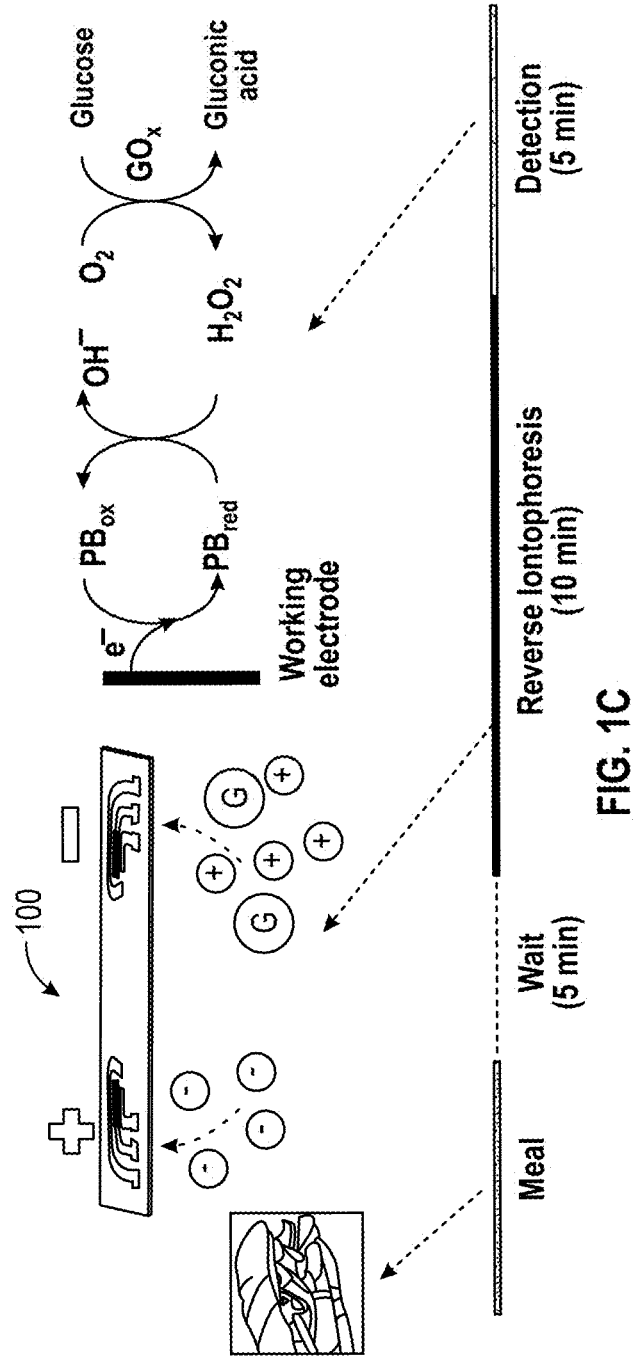
FIG. 1C shows a schematic illustration of the timeframe of an exemplary on-body implementation and the different processes involved in each phase.

FIG. 1A shows a schematic illustration of an exemplary iontophoretic-electrochemical sensor platform 100 for non-invasive analyte sensing, e.g. such as for glucose as shown in FIG. 1C, including a printable iontophoretic-sensing system displaying the tattoo-based paper (e.g., substrate shown in purple 102), Ag/AgCl electrodes (e.g., electrode contingents shown in silver 104), Prussian Blue electrodes (e.g., transducer shown in black 106), transparent insulating layer (e.g., shown in green 108) and hydrogel layer (e.g., shown in blue 109). FIG. 1B shows a photograph of an exemplary glucose iontophoretic-biosensing device applied to a human subject.

To operate the device, a wearer applies the non-invasive electrochemical sensor device to his/her skin for non-invasive chemical detection.

During operation for detection of the chemical analyte or analytes in ISF, a mild current (e.g., such as 0.3 mA/cm$^2$ or less) is passed between the iontophoretic electrodes (e.g., Ag/AgCl electrodes) of the anodic and cathodic electrode contingents to create an electric field through the wearer's skin to extract ISF to the surface of the skin by driving ions of the ISF toward the electrode contingents. For example, the electric field can be applied for one, a few, or several minutes (e.g., 5 to 10 minutes) to extract sufficient ISF containing physiologically relevant and detectable glucose levels to the surface of the skin. Subsequently, the chemical analyte present in the extracted ISF is quantified by the electrochemical sensor. For example, the electrochemical sensor electrodes can be operated to perform amperometric, potentiometric or voltammetric techniques that produce an electrical signal at the sensor electrodes, e.g., associated with an electrochemical or redox reaction sustained at the anodic and cathodic electrode contingents. Operation of the non-invasive electrochemical sensor device preferably includes extracting the ISF prior to operating the electrochemical sensor electrodes for electrochemical analysis, e.g., to save power and to avoid interference in the analyte detection that could be caused by the iontophoretic electrodes. However, in some implementations, the extracting and the detecting techniques can be performed concurrently.

Figure 1D:
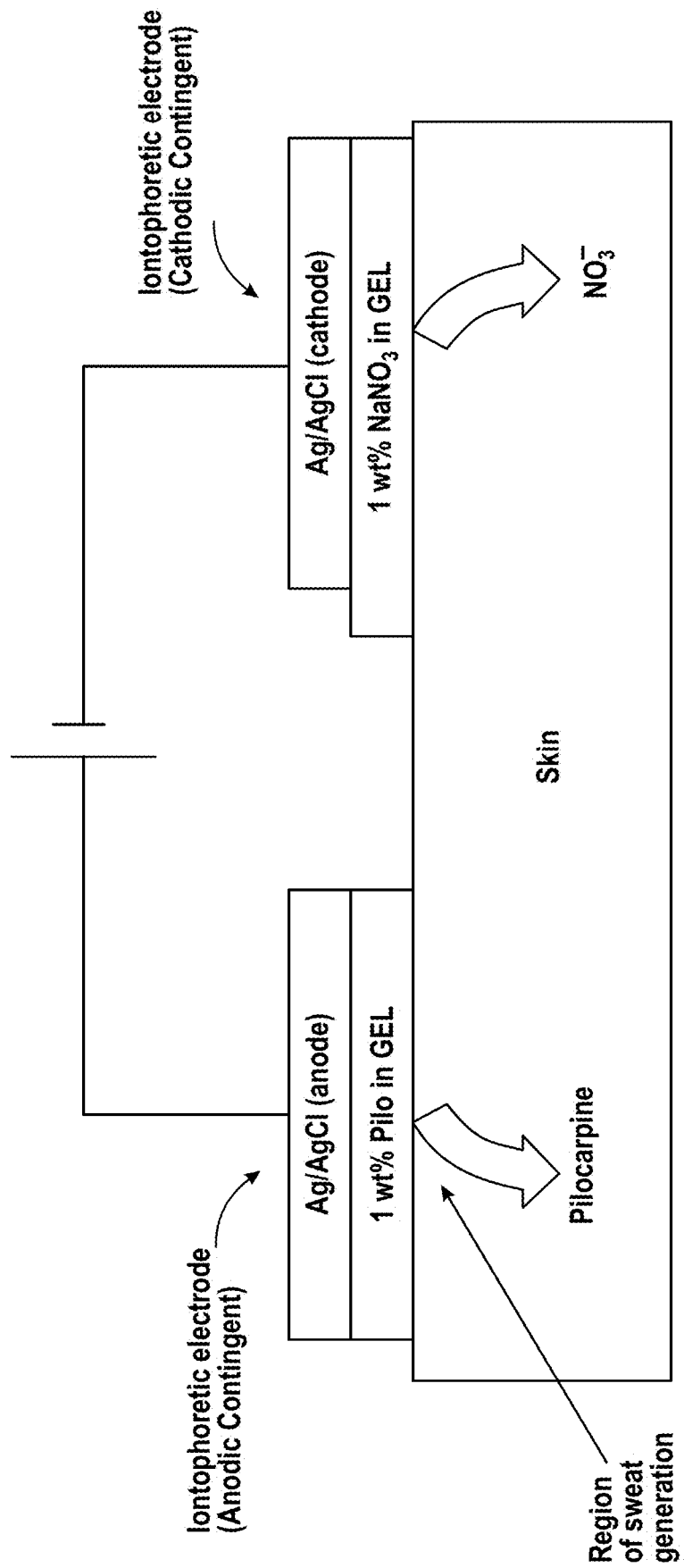
FIG. 1D shows an illustration of the sweat inducing mechanism using the present technology.

During operation for detection of the chemical analyte or analytes in a user's sweat, a mild current (e.g., such as 0.3 mA/cm$^2$ or less) is passed between the iontophoretic electrodes to create an electric field to administer sweat-inducing drug or chemical compounds into the skin. For example, the drugs or chemical compounds can be stored in the overlaying hydrogel over one or both of the iontophoretic electrodes (e.g., such as the hydrogel over the iontophoretic electrode of the anodic contingent). When the iontophoretic current passes through the hydrogel layer and through the skin, the electric field creates a force upon the drugs or chemical compounds that drives them into the skin. The drug or compound, while in the skin, induces the physiological process of perspiring (sweat) in the location of the drug or compound administration. FIG. 1D shows an illustration of the sweat inducing mechanism using the present technology. For example, the drug may be a positively charged compound so that electrostatic repulsion between the anode and the drug causes the drug to be administered into the skin. In the example shown in FIG. 1D, pilocarpine (Pilo) is illustrated. Subsequently, the chemical analyte present in the sweat that is present due to the sweat-inducing mechanism is quantified by the electrochemical sensor. For example, the electrochemical sensor electrodes can be operated to perform amperometric, potentiometric or voltammetric techniques that produce an electrical signal at the sensor electrodes, e.g., associated with an electrochemical or redox reaction sustained at the anodic and cathodic electrode contingents.

Upon completion of the test, the user can remove or replace the device and subsequently dispose of the removed device. For the next test, a wearer may utilize a new non-invasive electrochemical sensor device.

The non-invasive electrochemical sensor device is connected to an external electronic system, which can be portable and/or wearable on the user. The electronic system is used to power the electrochemical sensor device and analyze the acquired sensor signal (e.g., detected electrical current, voltage, etc.) to produce data on the analyte, e.g., such as the chemical concentration. In some implementations, the electronic system can include a display to present the analyzed data to the user. The information can be transmitted wirelessly from the electronic system to a user computing device, e.g., such as a smartphone, tablet, wearable computing device such as smartglasses, smartwatch, etc., and/or laptop or desktop computer. The electronic system can be connected to such user computing devices via physical contact (e.g., wired) or wirelessly using RF or Bluetooth communication, or other wireless communication techniques.

FIGS. 1A and 1B show a diagram and image of an exemplary non-invasive electrochemical sensor device for skin-worn glucose sensing on a temporary 'tattoo' platform, which can be operated by the described 'place-detect-dispose' on-body monitoring technique. The example device shown in FIGS. 1A and 1B can be utilized for detecting other analytes in ISF (e.g., lactate, urea, etc.) and sweat (e.g., alcohol, electrolytes, etc.). Also, such devices can be fabricated or integrated on other platforms, for example, paper, fabric, flexible plastics or stretchable elastomeric membranes using variety of fabrication routes. For example, the substrate can include silicone or polyurethane membranes, e.g., such as a polyurethane-based elastomer. The example device shown in FIGS. 1A and 1B include substrates with highly favorable substrate-skin elasticity with an attractive electrochemical performance.

FIG. 1C shows an illustrative diagram of using the exemplary non-invasive electrochemical sensor device for glucose monitoring. The example device uses a lower current density to extract the ISF glucose followed by selective amperometric biosensing using a glucose oxidase (GOx)-modified Prussian Blue transducer. Such flexible, low-cost and aesthetically pleasing iontophoretic-biosensing platform can be easily mated with the human skin with minimal intrusion to the wearer's routine. For the extraction and sensing operations using such printable skin-worn platform, the example device includes a Ag/AgCl reverse-iontophoresis electrodes (which can include an agarose hydrogel coating) for the anodic and cathodic electrode contingents, which are operable to efficient deliver ISF close to the working and counter/reference electrodes of the electrochemical sensor assemblies of the anodic and cathodic electrode contingents, as shown in FIGS. 1A and 1C. The working electrodes can include a biocatalytic reagent layer that can be optimized for imparting the sensitivity needed for detecting low (micromolar) glucose concentrations in the extracted ISF and high specificity in the presence of common interfering electroactive species.

An example of the non-invasive electrochemical sensor device for glucose monitoring includes a non-invasive wearable continuous glucose monitoring device for pain-free diabetes management. A continuous chemical monitoring device can be obtained by selecting a hydrogel layer that allows fast transport of all the extracted chemical analyte to the sensor surface. The device can be fabricated on user-friendly substrates, e.g., like temporary tattoo paper/stretchable elastomeric membrane, and thus causes least levels of intrusion to the wearer. The device relies on extraction of glucose from the ISF to the skin surface by passing a low current through the human skin followed by detection of the extracted glucose using a highly selective amperometric sensor. The device uses low current, which at least minimizes skin irritation. In some implementations, for example, the current density can be further lowered by incorporating skin permeation enhancers within the system.

An example of the protocol for continuous non-invasive glucose sensor includes applying of the device to the target skin location, such as, deltoid followed by turning ON the device. Upon activating the device, the reverse iontophoretic process is activated for a few minutes (<5 min) to extract ISF followed by deactivating the reverse iontophoretic process and activating the detection process to detect the extracted chemical analyte, for example, glucose. The iontophoretic and detection processes are repeated every 20-30 minutes using the worn device during a fixed period of time (24 hours to 1 week) to continuously monitor glucose levels. A similar process is also employed to detect other chemicals.

In one exemplary embodiment, a skin-worn temporary-tattoo based non-invasive glucose monitoring platform coupling an amperometric biosensor with a reverse iontophoresis operation as shown in FIG. 1A. The exemplary glucose monitoring platform includes body-compliant wearable electrochemical devices based on temporary tattoos that combine highly favorable substrate-skin elasticity with an attractive electrochemical performance. In some implementations, the skin-worn tattoo-based glucose detection device.

During operation, a mild current is passed between the Ag/AgCl iontophoretic electrodes through the wearer's skin to extract glucose molecules present in the ISF to the surface of the skin, as depicted in the illustration of FIG. 1C. The time and magnitude of the current passed can be further lowered by incorporating skin permeation enhancers within the hydrogel. Subsequently the extracted glucose is detected using a sensitive amperometric glucose sensor.

The wearable non-invasive sensor for detecting glucose has been utilized in example implementations that included applying it to human subjects to detect glucose spikes occurring due to food consumption. Such exemplary testing has been carried out at a fixed time after the meal consumption using the sensor in single-use 'place-detect-dispose' mode. The response obtained with said single-use glucose sensor has also been correlated with that obtained from a commercial blood glucose meter.

Exemplary implementations of the disclosed non-invasive iontophoretic-electrochemical sensing device were performed for in vitro optimization of the sensor sensitivity and selectivity, and in non-invasive glucose monitoring in human subjects, which was validated by simultaneous blood finger stick measurements using a commercial glucose meter. For example, the specificity of the exemplary wearable iontophoretic-electrochemical GOx sensor was validated by applying it simultaneously with an enzyme-free sensor (no GOx control) on human subjects. In some implementations, other enzymes, such as glucose dehydronates (GDH) can be used in the non-invasive biosensor disclosed in this patent document. Reverse iontophoresis prior to detection was demonstrated by analyzing the sensor response with and without active extraction of glucose ISF towards the sensor surface. The exemplary on-body implementations reveal that the exemplary iontophoretic-biosensing platform is capable of non-invasive glucose monitoring in real-life situations. For example, attractive features of the disclosed skin-worn sensor technology also highlight its potential for on-body monitoring of other target chemicals present in the interstitial fluid.

Exemplary reagents and instrumentation used in the exemplary implementations included the following. Glucose oxidase (GOx) from *Aspergillus niger*, Type X-S (EC 1.1.3.4), chitosan, bovine serum albumin (BSA), sodium phosphate monobasic (NaH2PO4), sodium phosphate dibasic (Na2HPO4), D(+)-glucose, L(+)-ascorbic acid, uric acid, acetaminophen and agarose were obtained from Sigma-Aldrich (St. Louis, Mo.). Acetic acid was obtained from EMD Chemicals Inc. (Gibbstown, N.J.). All reagents were used without further purification. Electrochemical characterizations were performed at room temperature using a CH Instruments electrochemical analyzer (model 1232A, Austin, Tex.) and PGSTAT 101 from Metrohm Autolab (Netherlands).

An exemplary fabrication process of the exemplary glucose sensor platform was implemented, followed by modification and transfer processes. For the exemplary implementations, sensor patterns were designed in AutoCAD (Autodesk, San Rafael, Calif.) and outsourced for fabrication on stainless steel through-hole 12 in.×12 in. framed stencils (Metal Etch Services, San Marcos, Calif.). Papilio temporary transfer tattoo base paper was purchased from HPS LLC (Rhome, Tex.). A sequence of the Prussian blue conductive carbon (C2070424P2, Gwent Group, Pontypool, UK), silver/silver chloride (Ag/AgCl) ink (4001, Engineered Conductive Materials, LLC, Delaware, Ohio), and insulator (Dupont 5036, Wilmington, Del.) inks were patterned on the substrate employing an MPM-SPM semiautomatic screen printer (Speedline Technologies, Franklin, Mass.). As illustrated in FIG. 1A, the iontophoretic-electrochemical sensor design includes a pair of reverse iontophoresis electrodes (Ag/AgCl ink), a pseudo reference/counter (Ag/AgCl ink) and working electrodes (Prussian Blue ink). A transparent insulator was screen printed over the surface of the electrode pattern to confine the electrode and contact areas. The Ag/AgCl ink was cured at 130° C. for 3 min, while the Prussian Blue ink was cured at 80° C. for 10 min in a convection oven.

Following the printing of the exemplary electrode transducers, the working electrode was functionalized with the reagent layer. The enzyme GOx solution (e.g., 34 mg/mL containing 10 mg/mL BSA stabilizer) was mixed with chitosan solution (0.5 wt % in 0.1 M acetic acid) in 1:1 v/v ratio. Subsequently, a 2 µL droplet of the above solution was casted on the electrode and dried under ambient conditions.

Exemplary in vitro characterizations were performed using a 0.1 M phosphate buffer (pH 7.0) solution containing 133 mM NaCl. The operating potential for the exemplary non-invasive wearable glucose sensor was selected by using cyclic voltammetry. The amperometric response was recorded after 1 min incubation in the sample solution, using a potential step to −0.1 V (vs Ag/AgCl) for 60 s. The sensor specificity was examined in the presence of relevant electroactive constituents, namely, 10 µM each of ascorbic acid, uric acid and acetaminophen.

Exemplary on-body glucose monitoring characterizations were performed using the exemplary iontophoretic, non-invasive wearable glucose sensor device. A continuous chemical monitoring device can be obtained by selecting a hydrogel layer that allows fast transport of all the extracted chemical analyte to the sensor surface. An agarose hydrogel, covering all the electrodes, was applied to the iontophoretic glucose sensor. For example, the hydrogel was prepared by heating a continuously stirred agarose solution (4% w/v) in 0.1 M phosphate buffer (pH 7) at 120° C. for 15 min. The solution was then cooled down to 60° C. and 100 µL of the solution was casted on the sensor area to form a uniform hydrogel layer covering all the three electrodes of both the anodic and cathodic contingents. The epidermal biosensor evaluation was performed in strict compliance with a protocol approved by the institutional review board (IRB) at the University of California, San Diego. A total of 7 consenting healthy volunteers (e.g., 4 males and 3 females between the ages of 20 and 40), with no prior medical history of heart conditions, diabetes, or chronic skeletomuscular pain, were recruited for participation in the study. The subjects were requested to arrive at the lab in fasting state. The epidermal studies comprised of transferring the iontophoretic glucose sensor to the skin followed by applying a constant current of 0.2 mA/cm$^2$ between the two reverse-iontophoresis electrodes for 10 min to extract ISF to the surface of the skin and finally recording the amperometric glucose response at an applied potential of −0.1 V (vs Ag/AgCl) for 5 min. The reverse-iontophoresis/detection cycle was performed first in the fasting state followed by consumption of a carbohydrate-rich meal. Thereafter, each subject was requested to wait for 5 min before a similar reverse-iontophoresis/detection cycle was repeated to measure the post-meal sensor response. The exemplary procedure is shown schematically in FIG. 1C. The crucial role of reverse iontophoresis was examined by analyzing the response obtained from two exemplary glucose biosensors (applied simultaneously to subjects) with and without reverse iontophoresis. The selectivity of the on-body sensor to glucose was evaluated using two exemplary sensors, one containing the GOx enzyme while the other devoid of it, applied simultaneously on the subjects' deltoid. For each human trial, simultaneous finger stick blood glucose measurements were performed using commercial glucose strips (e.g., Accu-Chek Aviva Plus®) to establish the correlation between the response of the exemplary iontophoretic glucose sensor device and that obtained from the commercial glucose meter.

The disclosed iontophoretic-biosensing device includes a different electrode pattern that includes the iontophoretic electrodes, e.g., as compared to 3-electrode designs. The glucose sensor of the of the exemplary iontophoretic-biosensing device shown in FIG. 1A includes the anodic and cathodic contingents, in which each contingent includes: an Ag/AgCl electrode that operates as a counter/reference electrode; a printable Prussian-Blue transducer (e.g., which was selected in this exemplary embodiment in view of its high selectivity towards hydrogen peroxide, the detectable product of the GOx enzymatic reaction); and an additional Ag/AgCl reverse iontophoretic electrode which encompassed the working and the counter/reference electrodes for efficient extraction of ISF close to the working and counter/reference electrodes. During the reverse iontophoresis operation, glucose is extracted at the cathodic contingent, and the working electrode of the cathodic contingent (e.g., modified with the GOx enzyme) can operate to selectively detect glucose. In other implementations where the analyte include a negative charge, e.g., such as lactate, the analyte is extracted at the anodic contingent, and the working electrode of the anodic contingent can be modified with the agent (e.g., catalyst, such as lactate oxidase (LOx enzyme) in the case of lactate) to selectively detect the analyte. In the exemplary implementations performed for glucose detection, chitosan was utilized as a polymeric matrix for immobilizing the enzyme on the transducer surface. However, in some implementations, a different biocompatible polymer other than chitosan can be used. While performing reverse iontophoresis, care should be taken to ensure proper contact between the skin and the sensor for efficient glucose extraction and to avoid skin irritation. For example, this can satisfied by evenly coating a layer of biocompatible agarose gel on each contingent to cover all the electrodes. The resulting glucose sensor can be easily applied to the skin, adhering and conforming to the the contours of the epidermis, similar to a typical rub-on temporary tattoo, e.g., as shown in FIG. 1B.

Exemplary Results of In Vitro Implementations

The glucose level in the ISF is in the same concentration range as that in the blood. However, the concentration of the ISF glucose extracted via reverse iontophoresis is approximately two orders lower than that of the corresponding ISF glucose level. Keeping this in view the response of the exemplary glucose tattoo sensor was evaluated over the 0-100 µM glucose concentration range, shown in FIG. 2A. These well-defined chronoamperometric responses to 10 µM glucose additions (a-1) revealed that the sensors responded linearly and favorably in this range, and could thus be utilized for detecting relevant ISF glucose levels extracted during on-body applications. Specificity of a sensor is of utmost importance for avoiding false alarms. Hence, the effect of physiologically relevant concentrations of common co-existing interfering electroactive species on the sensor response was examined. The exemplary results, displayed in FIG. 2B, highlight the high specificity of the sensor towards glucose (FIG. 2B, plot 'a') in presence of ascorbic acid, uric acid and acetaminophen (FIG. 2B, plot 'b'-'d'). Overall, the high sensitivity and selectivity demonstrated in FIGS. 2A and 2B reflect the coupling of the specific biocatalytic reaction with the low-potential amperometric transduction at the exemplary Prussian-Blue transducer, e.g., as compared to the high detection potential utilized in GlucoWatch® that could lead to compromised selectivity.

Figure 2A:
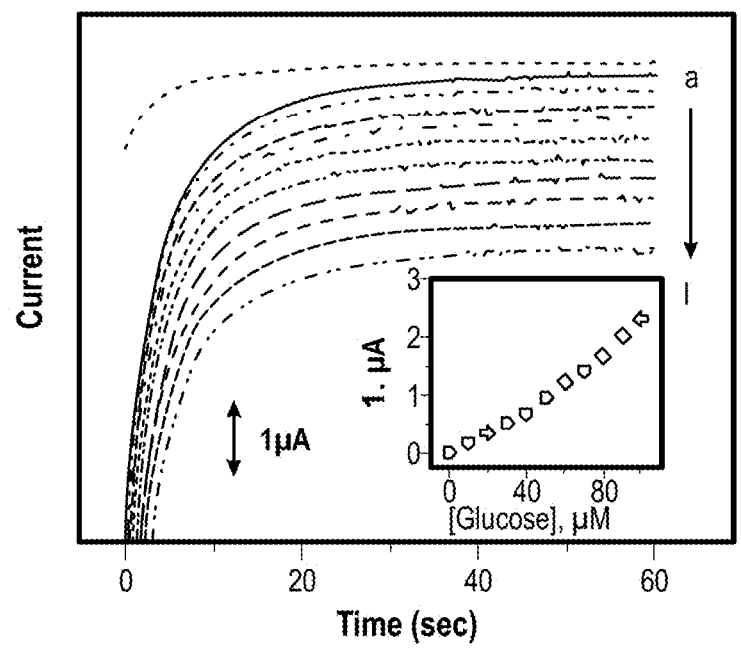
FIG. 2A shows a data plot showing exemplary chronoamperometric response data of an exemplary wearable electrochemical sensor to increasing glucose concentrations, from 0 μM (dash) to 100 μM (plot '1') in buffer in 10 μM increments.
Figure 2B:
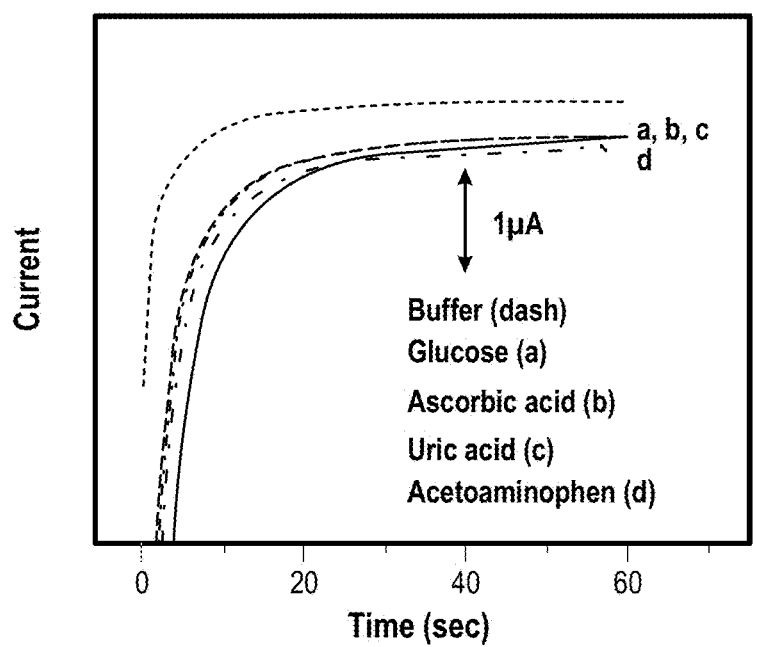
FIG. 2B shows a data plot depicting exemplary interference data in the presence of 50 μM glucose (plot 'a'), followed by subsequent 10 μM additions of ascorbic acid (plot 'b'), uric acid (plot 'c') and acetaminophen (plot 'd').

FIG. 2A shows a data plot showing exemplary chronoamperometric response data of an exemplary glucose sensor to increasing glucose concentrations, from 0 µM (dash) to 100 µM (plot '1') in buffer in 10 µM increments. FIG. 2B shows a data plot depicting exemplary interference data in the presence of 50 µM glucose (plot 'a'), followed by subsequent 10 µM additions of ascorbic acid (plot 'b'), uric acid (plot 'c') and acetaminophen (plot 'd'). In these plots, the exemplary conditions included: potential step to −0.1 V (vs Ag/AgCl); medium of phosphate-buffer with 133 mM NaCl (pH 7).

Exemplary Results of On-Body Implementations

Figure 5:
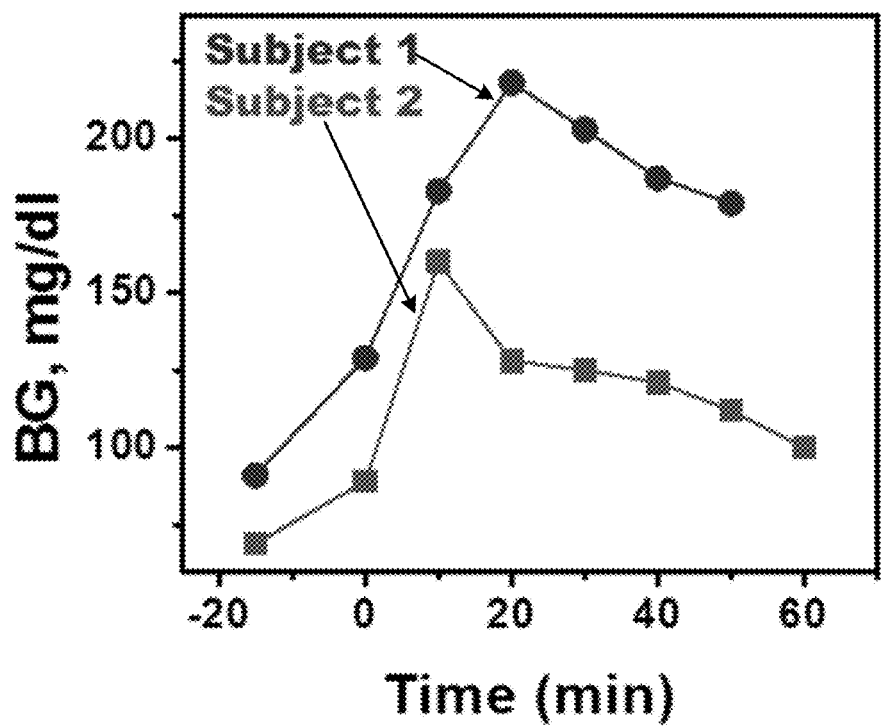
FIG. 5 shows a data plot depicting exemplary blood glucose levels measured for two subjects, in which the subjects finished consuming food at time T=0 min.

After demonstrating in vitro the ability of the analyte sensors to selectively measure micromolar glucose levels, on-body detection of ISF glucose levels was examined in human subjects under real-life scenarios with the system worn over the skin. Meal consumption triggers a rapid rise in blood glucose levels that may lead to detrimental effects on diabetic patients. Hence, the present technology provides the ability of the non-invasive tattoo-based sensor to monitor such sudden glycemic spikes. In the exemplary implementations, the first task was to identify the most appropriate time to perform the post-meal glucose sensing. Post-meal blood glucose levels of two subjects (1 male and 1 female) were thus measured at 10 min intervals over a 1 hour period following carbohydrate-rich meal (shown in FIG. 5). Based on these findings and literature data indicating approximately 15-20 min lag time between ISF and blood glucose levels, a 5 min waiting period (followed by 10 min of IP extraction) was considered for the post-meal glucose sensing on 7 human subjects. None of the subjects reported perceptible discomfort during these on-body studies. Only a mild tingling feeling at the skin under the iontophoresis electrodes was experienced by few subjects for less than 10 s at the beginning of the test.

Figure 3:
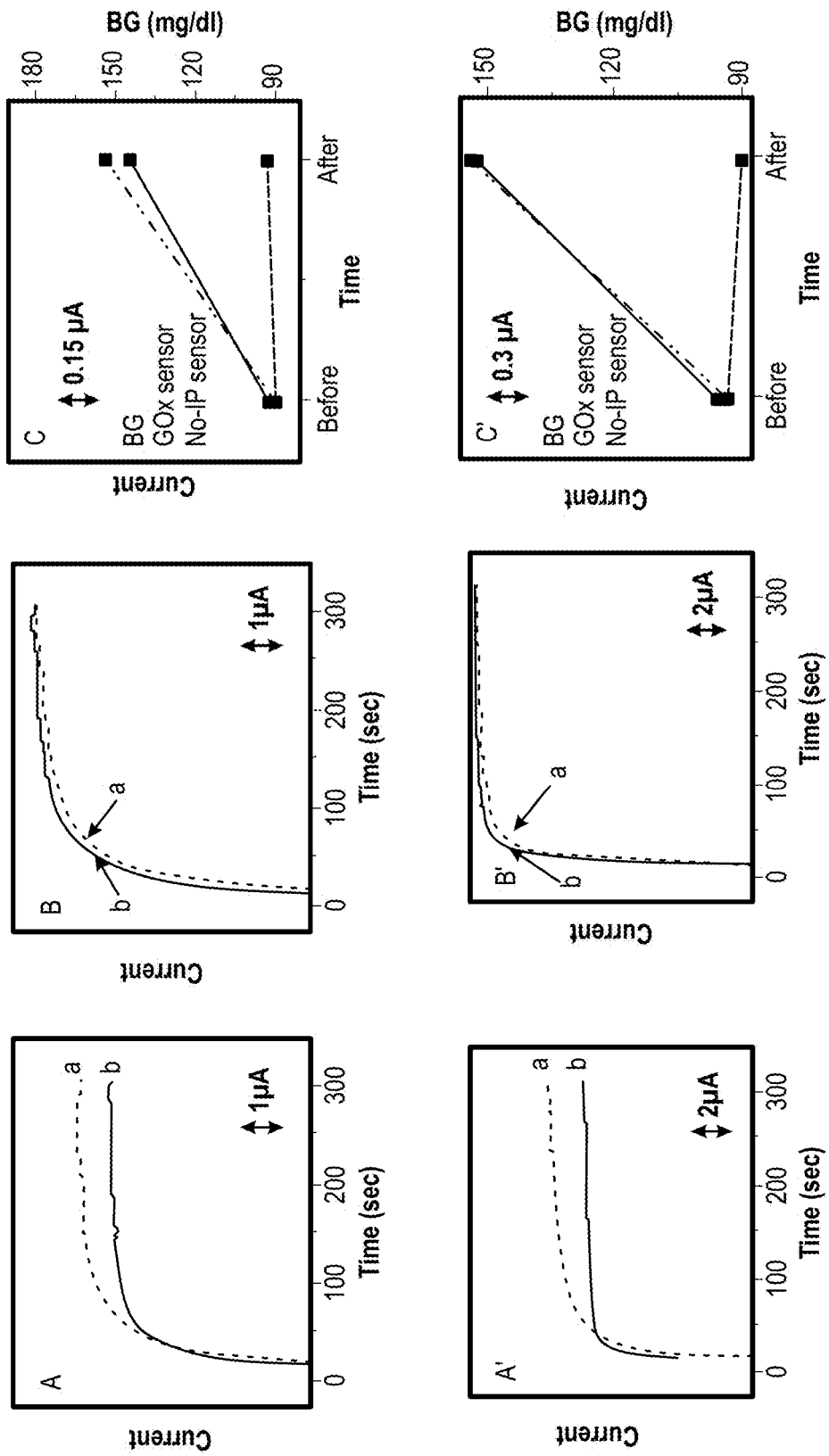
FIG. 3 shows exemplary amperogram data plots obtained for non-invasive glucose detection obtained from two human subjects, wearing simultaneously an exemplary wearable electrochemical sensor for glucose detection (A, A') with and (B, B') without the IP operation; and exemplary data plots (C,C') showing the correlation between data obtained from exemplary biosensors, with and without the IP procedure, and that obtained using a blood glucose (BG) meter.

Two example control experiments were carried out to corroborate the validity of the reverse iontophoresis-based glucose sensing system: (1) detection of passively diffused ISF glucose by a GOx-modified sensor (No-IP sensor), and (2) use of an unmodified (enzyme-free) sensor under active reverse-iontophoretic extraction of ISF (No-GOx sensor). Subjects were selected randomly to participate in each set of control experiments. For each subject the control sensor was applied adjacent to a glucose sensor on the deltoid with a spatial gap of approximately 1.5 cm. The response of the control sensor was recorded in tandem with the glucose sensor. FIG. 3 displays exemplary data obtained from two subjects simultaneously adorning the glucose sensor and the No-IP sensor.

FIG. 3 shows exemplary amperogram data plots obtained for non-invasive glucose detection obtained from two human subjects, wearing simultaneously an exemplary glucose tattoo sensor (A, A') with and (B, B') without the IP operation; and exemplary data plots (C,C') showing the correlation between data obtained from tattoo biosensors, with and without the IP procedure, and that obtained using a blood glucose (BG) meter. Exemplary conditions included: potential step to −0.1 V (vs Ag/AgCl).

As shown in FIG. 3, the data plot displays exemplary data obtained from two exemplary subjects simultaneously adorning the glucose tattoo sensor and the No-IP sensor. It can be clearly noted that the respective glucose tattoo sensor display a distinct increment in the post-meal current response (FIG. 3 A, A' plot b) as compared to the fasting state (FIG. 3 A, A' plots a). In contrast, for example, the respective No-IP sensors show minimal change in the current response before and after the meal (FIG. 3 B, B' plots; a vs b). This exemplary study underpins the importance of active reverse iontophoretic extraction of ISF glucose for performing non-invasive glucose detection. Simultaneous blood glucose measurements using a commercial Accu-Chek Aviva Plus® glucose meter and comparison with the response obtained from the tattoo sensors reveal the correlation between the non-invasive tattoo sensor and the blood glucose measurements.

Figure 4:
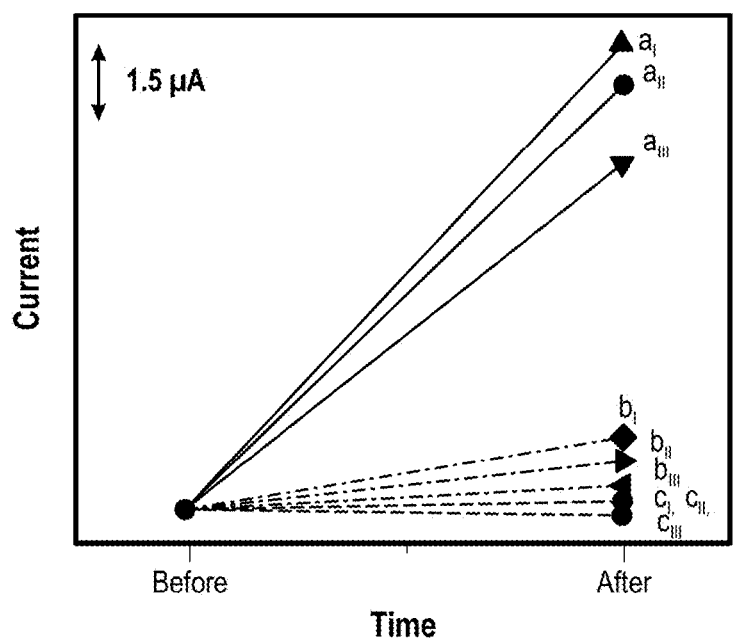
FIG. 4 shows a data plot showing the combined exemplary data obtained from exemplary wearable glucose sensors (plots '$a_i$', '$a_{ii}$' and '$a_{iii}$,'), No-GOx sensors (plots '$b_i$', '$b_{ii}$' and '$b_{iii}$') and No-IP sensors (plots '$c_i$', '$c_{ii}$' and '$c_{iii}$') before and after meal consumption.

Additional control experiments were carried out in the exemplary implementations for other subjects wearing the glucose tattoo sensor along with a No-GOx sensor. In this set of exemplary studies, the response from glucose tattoo sensors was also significantly higher compared to that of the enzyme-free sensors, highlighting the specificity of the sensor to detect the glucose substrate in presence of potential interfering species. FIG. 4 shows a data plot showing the combined exemplary data obtained from glucose tattoo sensors (plots '$a_i$', '$a_{ii}$' and '$a_{iii}$'), No-GOx sensors (plots '$b_i$', '$b_{ii}$' and '$b_{iii}$') and No-IP sensors (plots '$c_i$', '$c_{ii}$' and '$c_{iii}$') before and after meal consumption. Exemplary conditions for data acquisition were those as in FIG. 3.

As shown in FIG. 4, the data plot displays exemplary a collection of amperometric signals recorded with the glucose sensors (plots '$a_i$', '$a_{ii}$' and '$a_{iii}$'), No-GOx sensors (plots '$b_i$', '$b_{ii}$' and '$b_{iii}$') and the No-IP sensors (plots '$c_i$', '$c_{ii}$' and '$c_{iii}$') for different human subjects. These data clearly illustrate the ability of the tattoo sensors to detect spikes in the glucose level occurring due to food consumption. Another control experiment of the exemplary implementations was performed to identify the variation in the sensor response in absence of glucose spike. During this exemplary control experiment, a glucose tattoo sensor and a No-GOx sensor were applied simultaneously to a human subject. It was noted that both the blood glucose level as well as the response from the two sensors remained fairly stable, thus underscoring the sensor's ability to specifically detect blood glucose spikes.

In some embodiments, the disclosed iontophoretic-biosensor devices include an integrated electronic backbone for powering the sensor, and signal processing and wireless communication units on the flexible wearable sensor platform, capable of collecting continuous data from the diabetes patient, and performing large-scale glucose monitoring across diverse patient populations. The exemplary iontophoretic-biosensing platform can be readily used for the non-invasive monitoring of other chemical markers present in the interstitial fluid, and for transcutaneous drug delivery.

Figure 6A:
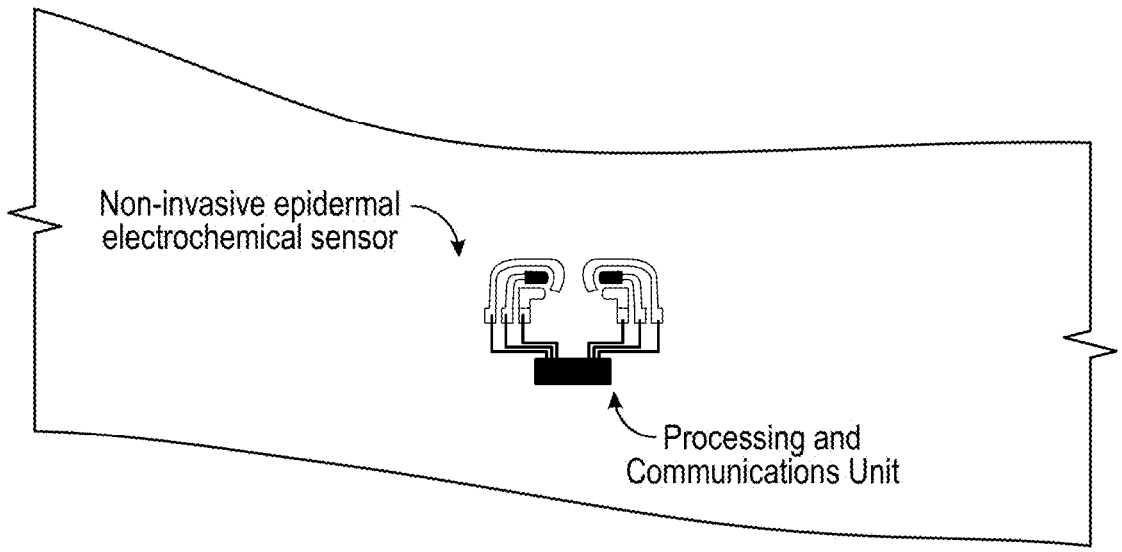
FIG. 6A shows a diagram of an exemplary non-invasive glucose sensing device of the disclosed technology including a non-invasive epidermal electrochemical sensor and integrated processing and communications unit.
Figure 6B:
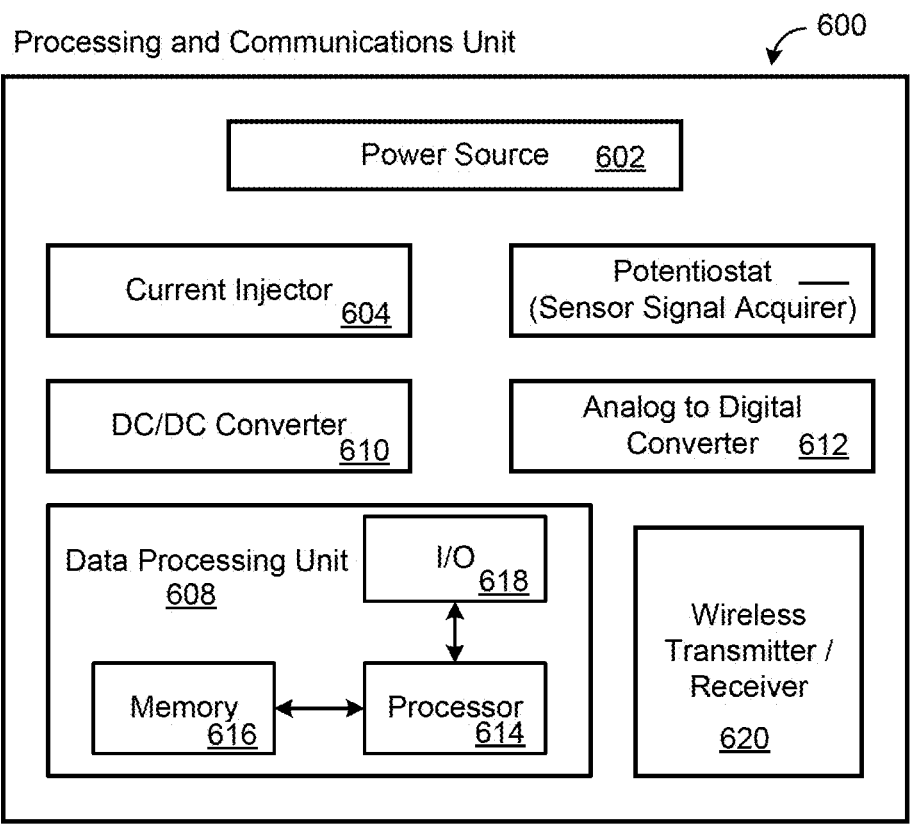
FIG. 6B shows a block diagram of an exemplary integrated processing and communications unit.

FIG. 6A shows a diagram of an exemplary non-invasive electrochemical sensor of the disclosed technology including a non-invasive epidermal iontophoretic electrode assembly and electrochemical sensor electrode assembly with an integrated processing and communications unit 600. FIG. 6B shows a block diagram of an exemplary integrated processing and communications unit 600. As shown in FIG. 6B, the processing and communications unit 600 can include a power source 602 (e.g., a battery), a current injector 604, a potentiostat (sensor signal acquirer) 606, a data processing unit 608 capable of signal processing and communications (e.g., to external devices), and DC/DC and/or analog-to-digital converters and/or signal conditioning circuits 610, 612. The data processing unit can include a processor to process data and a memory in communication with the processor to store data. For example, the processor can include a central processing unit (CPU) 614 or a microcontroller unit (MCU). For example, the memory 616 can include and store processor-executable code, which when executed by the processor, configures the data processing unit to perform various operations, e.g., such as receiving information, commands, and/or data, processing information and data, and transmitting or providing information/data to another entity or to a user. In some implementations, the data processing unit can be implemented by a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The data processing unit can include an input/output unit (I/O) 618 that can be connected to an external interface, source of data storage, or display device. For example, various types of wired or wireless interfaces compatible with typical data communication standards can be used in communications of the data processing unit via the wireless transmitter/receiver unit 620, e.g., including, but not limited to, Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of an external device. For example, an external display device can be configured to be in data communication with the data processing unit, e.g., via the I/O, which can include a visual display device, an audio display device, and/or sensory device, e.g., which can include a smartphone, tablet, and/or wearable technology device, among others.

In some embodiments, for example, the electronic system can be contained in a housing that electrically connects to the sensor device via electrical contact pads on the substrate of the sensor device that are interconnected to the electrodes of the sensor device. In such embodiments, the housed electronic system can be a portable device that attaches and detaches from the device, and be stored on the user to be readily available for the user's next test, e.g., such as in a user's pocket, purse, etc. The sensor device can make electrical contact with the portable device via a number of connections including pressure contacts, magnetic contacts, soldering contacts, etc. The housed electronic system can be in wired or wireless connection with a user's mobile communication or computing device, e.g., such as a smartphone, tablet, wearable computing device such as smartglasses, smartwatch, etc., and/or laptop or desktop computer. The exemplary housed electronic system can supply power, operate, and retrieve the acquired physiological-related electrical signals from the sensor device.

Tattoo—or Patch-Based Wearable Electrochemical Biosensor Device

In some implementations, the disclosed technology can be implemented as a skin-worn tattoo- or patch based wearable electrochemical biosensor device for non-invasive analyte monitoring, including glucose and alcohol. Exemplary implementations using an exemplary flexible tattoo- or patch-based glucose biosensor device of the present technology can include in vitro characterization of the tattoo sensors that showed their ability to detect micromolar levels of glucose in the presence of common interfering chemical species; and including on-body evaluation of the tattoo-based iontophoretic-biosensing platform that showed the ability to detect the rise in the glucose level after a meal in a non-invasive fashion. The disclosed tattoo iontophoretic-biosensing platform can be utilized for everyday use in diabetes management. The present technology demonstrates a non-invasive highly selective pain-free continuous glucose monitoring platform. The exemplary wear-and-forget device can be easily worn by a person to autonomously monitor glycemic levels, e.g., thereby avoiding the need for active patient involvement. The wearable device also has immense potential for the health conscious consumers who wish to avoid glucose spikes and the subsequent initiation of the body's fat storage process due to high-glycemic food consumption.

Fabrication of Glucose Sensor Patch

A tattoo-based or patch-based glucose sensor is fabricated on a flexible 25 μm thick polyimide, polyester or polyterephthalate sheets using a screen printer. The substrate is not limited to these materials, and other flexible plastic, textile or elastomeric membranes can also be used. The fabrication comprises of printing a sequence of Ag/AgCl ink and Prussian Blue conductive carbon ink on the flexible substrates using custom-designed stencils. The magnetic contact pads (used for attaching a custom-built flexible PCB electronics for wireless communication) are realized by attaching commercially-obtained conductive and magnetic metal alloy foil by using conductive glue.

Figure 7:
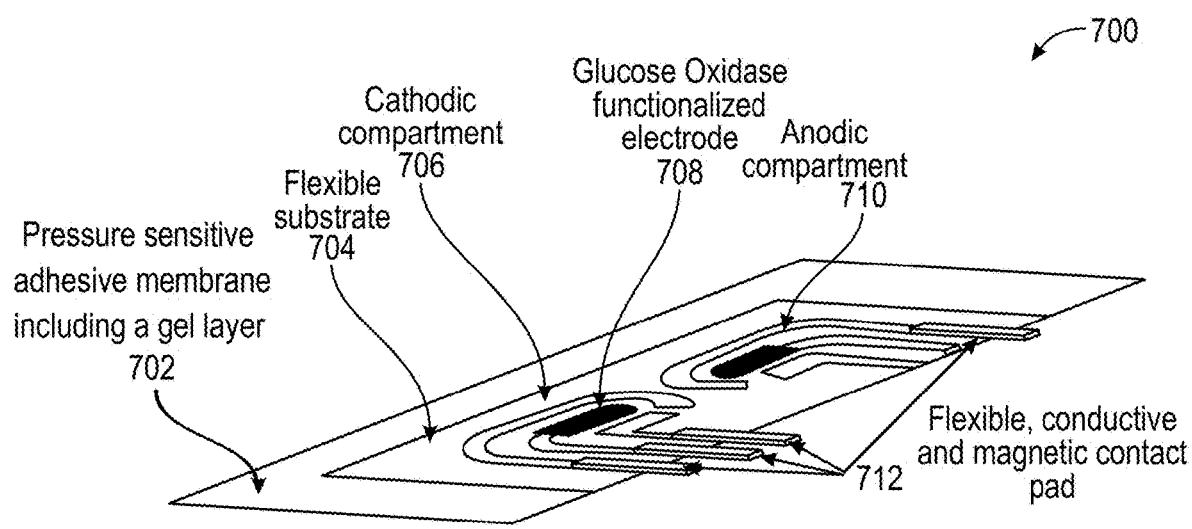
FIG. 7 is a schematic of an exemplary tattoo- or patch-based electrochemical biosensor device with different components of magnetic contacts.

FIG. 7 is a schematic of an exemplary tattoo- or patch-based electrochemical biosensor device 700 with different components of magnetic contacts. The tattoo- or patch-based electrochemical biosensor device 700 includes a pressure sensitive adhesive membrane 702 and a flexible substrate 704. A cathodic compartment 706, a glucose oxidase functionalized electrode 708, an anodic compartment 710, and flexible, conductive, and magnetic contact pads 712 are disposed over the flexible substrate 704. The working electrode is functionalized with the reagent layer. The enzyme GOx solution (40 mg/mL containing 10 mg/mL BSA stabilizer) is mixed with chitosan solution (0.5 wt % in 1 M acetic acid) in 1:1 v/v ratio. Subsequently, a 2 µL droplet of the above solution is casted on the electrode and dried under ambient conditions. Next, 100 µL of 4 wt % agarose gel in 0.1M phosphate buffer is coated onto the sensor. Finally, the flexible glucose sensor patch is applied to medical grade pressure sensitive adhesive membrane 702. A wide range of commercial urethane, textile based adhesive membranes can be used for this purpose.

Applying the Glucose Sensor Patch on the Body

Figure 8A:
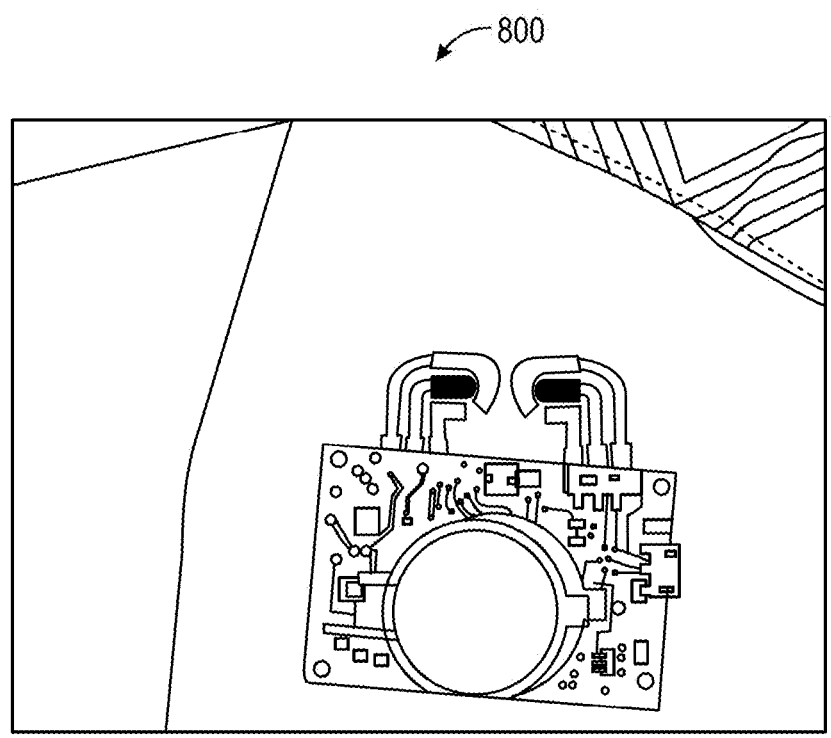
FIGS. 8A and 8B are photos an exemplary glucose sensor patch device and exemplary flexible PCB electronics.
Figure 8B:
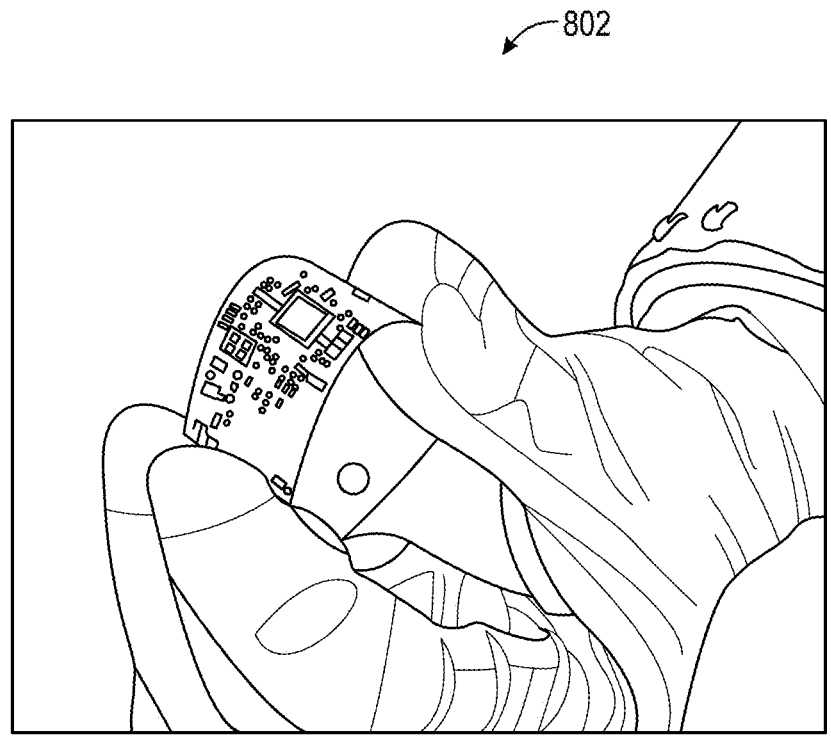

The tattoo- or patch-based glucose sensor can be applied to a region of the body, such as the deltoid region. A flexible PCB electronics board is attached to the wearable patch via magnetic attraction between the magnetic contacts pads of the PCB board and that of the glucose patch. FIGS. 8A and 8B are photos of an exemplary glucose sensor patch device 800 and exemplary flexible PCB electronics 802. The flexible PCB electronics 802 provide an effective means to inject current into the body for the reverse iontophoresis process.

On-Body Studies

Figure 9:
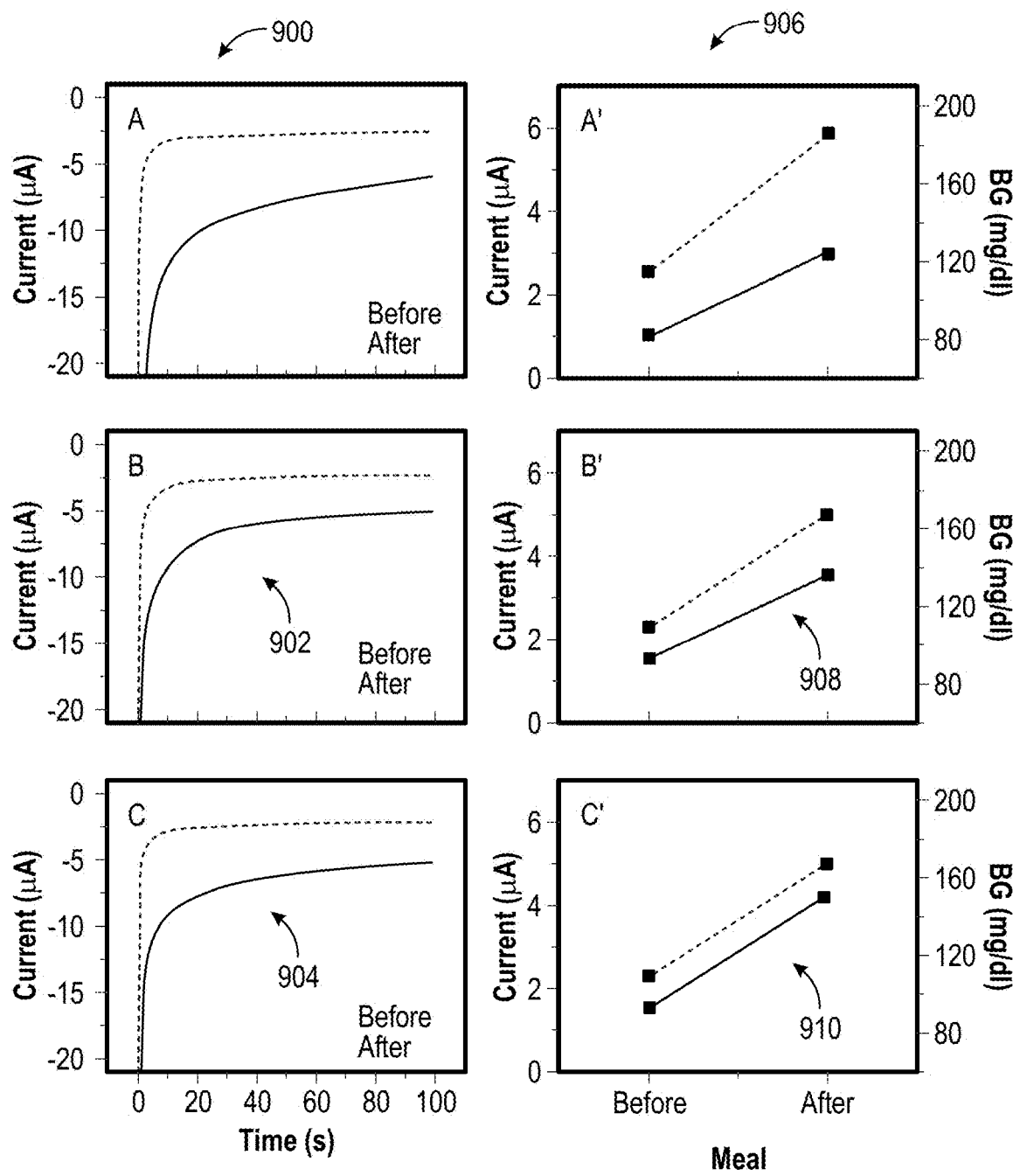
FIG. 9 shows exemplary results for three different subjects obtained by the disclosed glucose sensor patch device in conjugation with the wireless electronic board.

The extraction of glucose from the skin interstitial fluid greatly depends on the contact between the sensor patch and the skin. Conformal contact between the skin and the sensor leads to efficient glucose extraction, thus reducing the duration of reverse iontophoresis and possibility of skin burns. By employing a highly flexible thin polyimide sheet as a substrate for fabricating the glucose sensor along with a skin-conforming medical-grade pressure sensitive adhesive, the reverse iontophoresis duration was reduced to 5 min followed by 3 min of amperometric detection of the extracted glucose as compared to the glucose tattoo sensor platform, that required 10 min of reverse iontophoresis and 5 min of detection. Thus, by using the patch platform, the frequency of glucose detection can be increased while reducing the possibility of skin irritation. FIG. 9 shows exemplary results for three different subjects obtained by the disclosed glucose sensor patch device in conjugation with the wireless electronic board. The glucose for each subject was measured in the fasting state and after having breakfast. Specifically, FIG. 9 shows amperometric response of glucose sensor patch recorded for three subjects before and after breakfast A (900), B (902), C (904) and correlation of glucose levels measured by a commercial blood glucose meter (blue plots) with that measured by the glucose sensor patch (black plots) for the three subjects A' (906), B' (908), C' (910).

Figure 10:
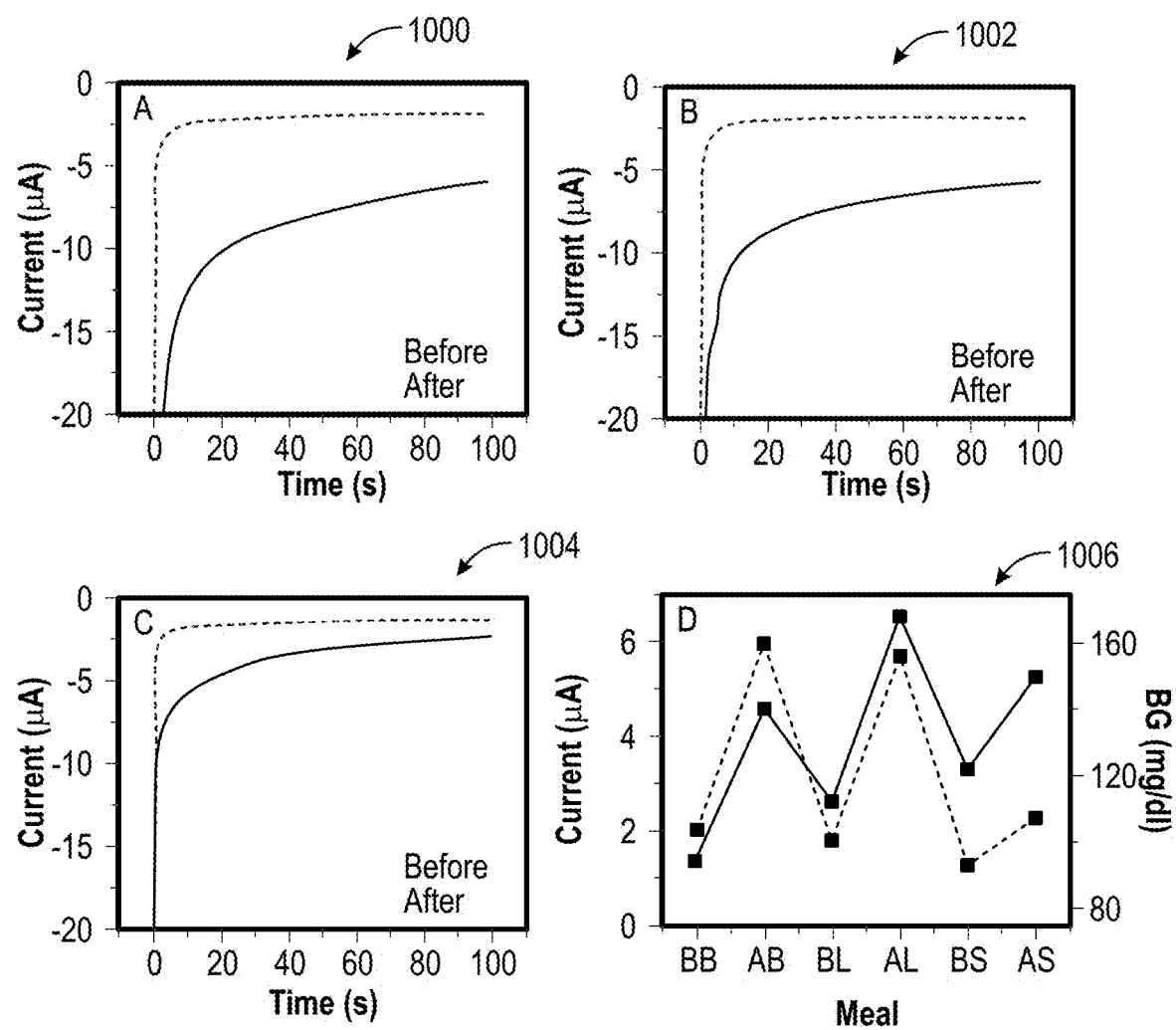
FIG. 10 shows exemplary data from a separate study where the disclosed glucose sensor patch device recorded the glucose spikes occurring after a subject consumed breakfast, lunch and snacks.

FIG. 10 shows exemplary data from a separate study where the disclosed glucose sensor patch device recorded the glucose spikes occurring after a subject consumed breakfast, lunch and snacks. For each meal, a new patch was applied. Specifically, FIG. 10 shows glucose spikes occurring after consumption of A (1000) breakfast, B (1002) lunch and C (1004) snacks as recorded by glucose sensor patches. D (1006) Correlation between glucose levels obtained from a commercial blood glucose meter (blue plot) with that recoded by glucose sensor patches (black plot). In plot D (1006), the horizontal axis shows BB: before breakfast; AB: after breakfast; BL: before lunch; AL: after lunch; BS: before snacks and AS: after snacks.

Tattoo-Based Transdermal Alcohol Sensor

Blood alcohol content (BAC) is most commonly used as an indicator of alcohol intoxication. However, blood sample is nominally obtained by invasive means, which gives people pain during sample collection. To overcome this issue, disclosed is a novel solution to monitor BAC non-invasively in real-time using a wearable tattoo-based biosensor named 'AlcoTatt'. Based on a correlation between alcohol concentration in sweat and blood, the disclosed skin-worn electrochemical biosensor measures transdermal alcohol content (TAC) in induced sweat via iontophoresis to estimate BAC, with the measured data wirelessly transmitted to laptop or mobile device for real-time analysis. The on body performance of 'AlcoTatt' prototype is demonstrated on human subjects with ingestion of alcohol drinks showing high sensitivity and specificity towards ethanol in sweat. The present document supports the application of a skin-worn tattoo-based wearable electrochemical biosensor for the non-invasive alcohol monitoring.

Alcohol consumption leads to harmful consequences such as traffic accidents and degenerated health care. Therefore, accurate measurement of alcohol consumption is important for preventing alcoholism and alcohol abuse and the effectiveness of their treatment. BAC is most commonly used as an indicator of alcohol intoxication. Blood samples are conventionally obtained by invasively pricking a fingers or earlobe, which is a painful process that demands user compliance. The disclosed technology provides for an alternative way to measure BAC in a non-invasive, real-time manner.

The disclosed wearable electrochemical sensors can detect metabolites and electrolytes in a non-invasive way using sweat and interstitial fluid. These sensors can be integrated directly on flexible temporary tattoo substrates for epidermal sensing applications. Such body-compliant printable electrochemical sensors provide elasticity characteristic of temporary tattoos along with resistance to mechanical stress and compatibility with the non-planarity of the epidermis. Expanding this attractive skin-worn platform towards non-invasive alcohol detection in sweat benefits wearers comfort and compliance as well as enables continuous real-time alcohol monitoring, which can be useful for monitoring clinical treatment status, individuals who are asked to maintain abstinence of alcohol. Also, the device can be used to verify drinking events, prevent driving under the influence, charging with driving under influence and track recidivism.

Breathalyzers are the most commonly used device to indirectly estimate BAC by measuring breath alcohol concentration (BrAC). The breathalyzer instruments calculate BAC by following Henry's law, which has difficulties in achieving high accuracy because it can be easily affected by humidity, temperature and individuals. BAC also can be estimated by measuring transdermal alcohol concentration (TAC), because the person's perspiration can contain traces of alcohol when the person consumes alcohol. The Giner TAS V is the wearable prototype to measure TAC by detecting the local ethanol vapor concentration over the skin. However, it showed time delay in peak TAS signal compared with BAC estimated by breathalyzer varying from 30 min to 2 hours. The disclosed tattoo-based alcohol sensor can monitor BAC non-invasively in real-time is highly desired. A correlation between ethanol concentration in blood and sweat during alcohol consumption, with a ratio of 0.81 can be utilized by the disclosed tattoo-based alcohol sensor. The disclosed tattoo-based alcohol sensor is wearable and thus not bulky to carry and does not require replacement of electrodes between the iontophoresis and amperometric detection steps.

Specifically, the disclosed wearable tattoo-based alcohol biosensor can be used to monitor BAC non-invasively in real-time. The disclosed wearable tattoo biosensor provides several distinct advantages and innovations for practical applications as below. It represents the first example of integration of iontophoretic and amperometric-detection system, obviating the need for replacement of electrodes between iontophoresis and detection. The electrodes are fabricated by screen-printing on a wearable tattoo platform, which is easy to fabricate, wear, and remove as well as cost-effective for mass-production. Finally, flexible wireless electronics has been incorporated with tattoo electrodes, which enables real-time non-invasive measurements and data transmission to lap-top/mobile device via Bluetooth communication. The flexible skin-worn board offers resistance to mechanical stress from movement of wearer along with compatibility with the non-planarity of the epidermis. As described in this document, the on-body demonstrations reveal that the tattoo-based iontophoretic-biosensing platform holds considerable promise for non-invasive alcohol monitoring in real-life situations.

Figure 11:
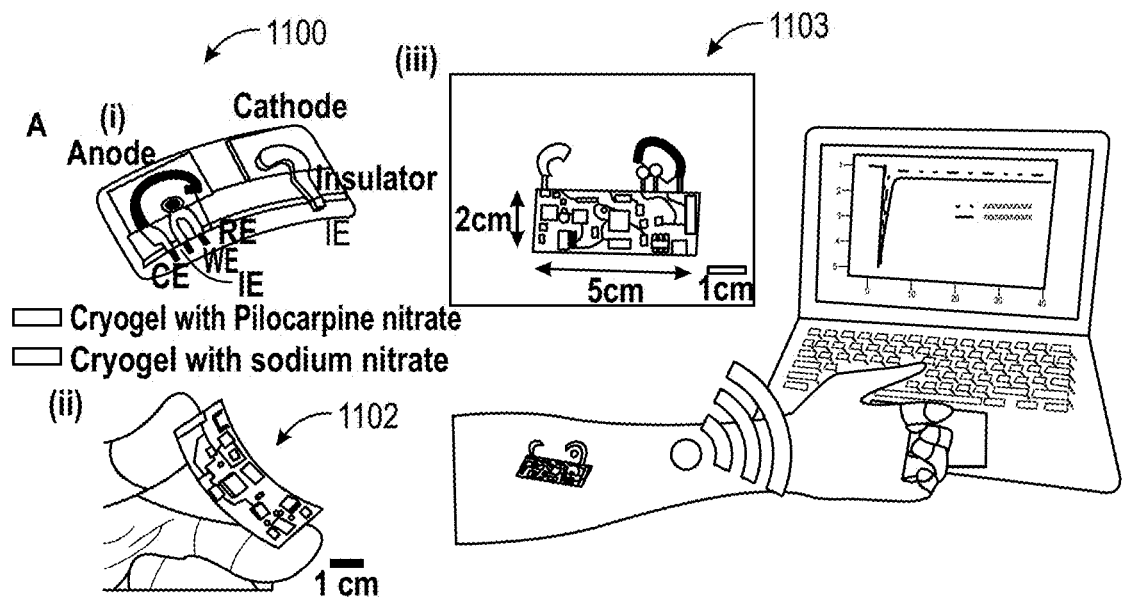
FIG. 11 shows an exemplary tattoo-based transdermal alcohol sensor devices and systems.
Figure 11:
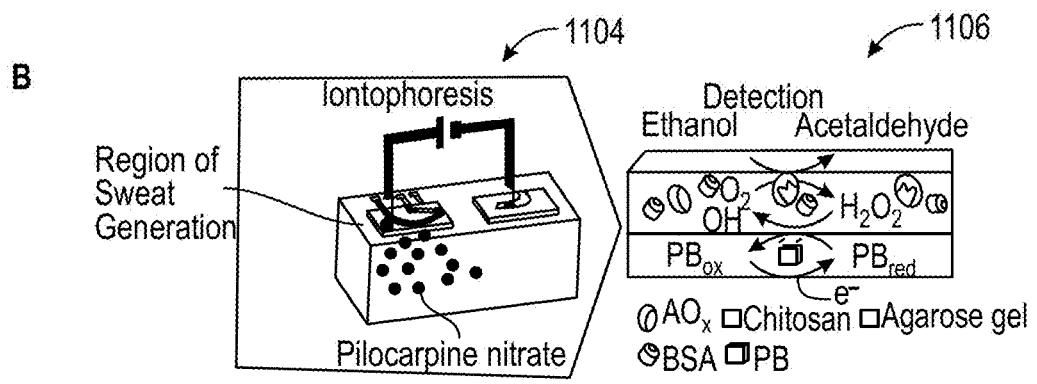
Figure 11:
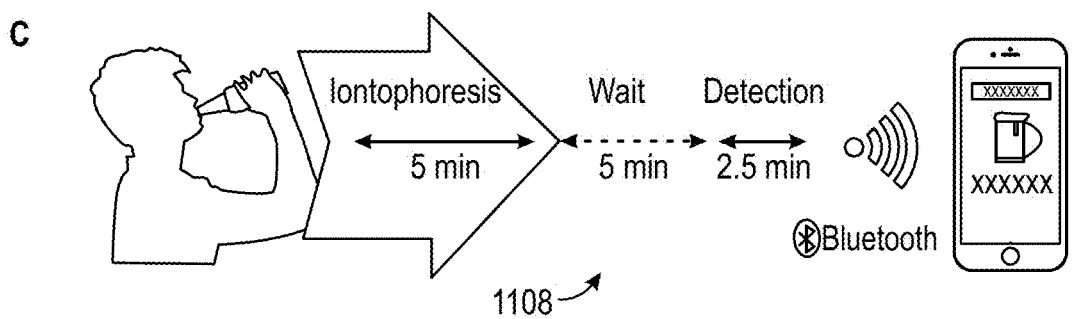

FIG. 11 shows an exemplary tattoo-based transdermal alcohol sensor devices and systems. For example, part (A)(i) is a schematic diagram of iontophoretic-sensing tattoo electrode displaying iontophoretic electrodes (anode and cathode) and sensing three electrodes (working, reference and counter electrodes) (1100). Part (A)(ii) is a photograph of flexible wireless electronics (1102). Part (A)(iii) is a photograph of Alcohol iontophoretic sensing tattoo device with integrated flexible electronics applied to a human subject (1103). Part (B) is a schematic diagram of constituents in an exemplary iontophoretic system (1104) and exemplary enzymatic reaction and chemical modification for ethanol sensing on working electrode (1106). Part (C) shows exemplary schematic procedures of on-body study of alcohol sensing (1108).

An exemplary procedure to monitor alcohol level in sweat using the tattoo-based transdermal alcohol sensor device includes iontophoresis and amperometric detection processes. Iontophoresis is performed to induce sweat occurrence by delivering pilocarpine as illustrated in FIG. 11, part (B) (1104). Enzymetric reaction of alcohol oxidase and modification of working electrode on Prussian Blue (PB) transducer are shown in FIG. 11, part (B) (1106). In FIG. 11, part (A)(i) (1100), the tattoo electrodes include iontophoretic electrodes ("IE" anode and cathode) and sensing electrodes (CE, WE, and RE: counter, working and reference). For wireless monitoring, the tattoo electrodes can be integrated with flexible electronics.

As shown in FIG. 11, part (C) (1108), the level of alcohol in sweat can be monitored under consumption of alcohol beverage by performing ionotophoresis (5 minutes), waiting (about 5 minutes), and amperometric detection by integrated flexible electronics (about 2.5 minutes) and data can be transmitted wirelessly to a mobile device or lap-top via Bluetooth communication, for example, in real-time. Other wireless communications protocols can also be used.

Fabrication, Chemical Modification, and Transfer Process of Tattoo Sensor

Patterns for printing the sensor were designed in AutoCAD (Autodesk, San Rafael, Calif.) and stainless steel plates (12×12 inch.$^2$) were etched to fabricate stencils (Metal Etch Services, San Marcos, Calif.). Temporary transfer tattoo paper kits were obtained from HPS Papilio (Rhome, Tex.). A sequence of the silver/silver chloride (Ag/AgCl) ink (E2141 Ercon Inc., Wareham, Mass.) and prussian blue conductive carbon (Gwent Group, UK) were screen-printed on the substrate by using an MPM-SPM semi-automatic screen printer (Speedline Technologies, Franklin, Mass.). As illustrated in FIG. 11, the tattoo sensor design includes iontophoresis, pseudo reference, and counter electrodes patterned from Ag/AgCl ink, and the working electrode patterned from Prussian blue ink. A transparent insulator was screen printed over the surface of the electrode pattern to confine the electrode and contact areas. Each printed layer was cured in oven after printing. The Ag/AgCl ink was cured at 90° C. for 10 min, while the prussian blue ink was cured at 80° C. for 10 min in an oven.

In order to obtain ethanol transducer, the working electrode was then functionalized with the enzymatic layer (BSA, chitosan, and AOx enzyme). The AOx enzyme, BSA stabilizer and chitosan solution (0.5 wt % in acetic acid solution) was mixed together in an 8:1:1 v/v ratio. Afterward, a 4 µL droplet of the mixed solution was casted on the electrode. After air-drying, the electrode was covered with a 2 µL chitosan solution. Then, the electrode was dried under ambient conditions. The agarose hydrogel was prepared by heating a continuously stirred agarose solution (4% w/v) in 0.1 M potassium phosphate buffer (pH 7.0) until agarose is completely dissolved. Dissolved agarose hydrogel is then casted on the working electrode. Then prepared PVA cryogels (2.0×1.5 cm$^2$) were soaked in 1% pilocapine nitrate and 1% sodium nitrate and then covered on anode and cathode compartments, respectively. The PVA cryogels were made as following procedure by freezing and thawing sequences of PVA solution. First, 5.0% v/v PVA solution was prepared in deionized water by heating the solution to 120° C. and then cooled to room temperature. After the mixture is cooled, it was placed in the ice bath and pH was adjusted to pH 1 by adding 5 M hydrochloric acid. Subsequently, the cross-linker glutaraldehyde was added to make a final concentration 0.5% w/v. The final mixture was then stirred for 1 minute and poured onto the petri dish to set in −20° C. freezer overnight. The cured PVA cryogel was patterned by paper cutter to control size of applying iontotophoresis.

Evaluation of Sensor Performance in Buffer Medium

The electrochemical performance of the alcohol tattoo biosensor was first tested in 0.1M phosphate buffer (pH 7.0) medium. Chronoamperometric response was measured by stepping the potential to −0.2V (vs. Ag/AgCl) for 60 s after 1 min incubation. The calibration curve was obtained with 3 mM increments of ethanol concentrations up to 36 mM in buffer solution. Selectivity was examined by response of 10 mM ethanol in the presence of relevant electroactive species: 0.2 mM glucose, 10 mM lactate, 84 µM creatine, 10 µM ascorbic acid, and 60 µM uric acid.

Evaluate the On-Body Performance of Wearable Tattoo Alcohol Biosensor

The epidermal evaluation on human subjects was conducted in strict compliance following a protocol approved by the institutional review board (IRB) at the University of California, San Diego. Total nine healthy volunteers were recruited for on-body evaluation of the developed sensor under taking alcohol beverages. First, tattoo biosensor was transferred on subject's arm and a set of ethanol detection in sweat is followed to get a current response at BAC 0.00% ('before drinking'). Experimental time frame for on-body experiments is illustrated in FIG. 1C. The set of ethanol detection consists of iontophoresis and amperometry. During iontophoresis process, a constant current of 0.6 mA (0.2 mA/cm$^2$) was applied through PVA cryogel between the two iontophoresis electrode (anode and cathode) for 5 min to deliver pilocarpine chemical towards skin to induce sweat. After iontophoresis, 5 min of resting was required to give time to generate sweat. Finally, amperometric response of ethanol in sweat was recorded at applied potential of −0.2 V (vs Ag/AgCl) for 150 sec, corresponding to the current response at BAC 0.00%. The subject was asked to take an alcoholic beverage (12 oz. of beer or 5 oz. of table wine) and waited for 10 min to let alcohol diffuse in blood stream. One set of iontophoresis/detection cycle was followed to check the response of ethanol in sweat. Along with on-body experiments taking alcohol beverages, three different types of control experiments (without drinking, without enzyme modification, without iontophoresis) were performed. The sensing response towards sweat ethanol was confirmed by testing without drinking alcoholic beverages.

Furthermore, additional on-body experiments are followed to verify correlation between BAC and current response from our tattoo sensor with serial consumption of wine drinks. As described in previous paragraph, same experimental procedure was conducted by repeating two sets of drink and measurement. Before drinking (when BAC is 0.00%), current response was recorded. Then, after $1^{st}$ drinking, current response was obtained and followed by $2^{nd}$ drinking and measurement. Each set of measurement cycle is accompanied with simultaneous measurement of BAC using commercial breathalyzer (Alcovisor Mars breathalyzer) to validate our sensor performance in comparison with commercial alcohol sensor.

Design and Fabrication of Wireless Flexible Printed Circuit Board

This work introduces a complete flexible wearable device for non-invasive monitoring of alcohol (FIG. 1). The system includes a tattoo-based iontophoresis alcohol monitoring system, as well as a flexible wireless electronic system that transmits the alcohol level information through a Bluetooth low energy (BLE) link (FIGS. 1, A and B). A BLE-enabled printed circuit board has been designed to implement a prototype for the iontophoresis alcohol biosensor system. The circuit employs a Texas Instrument (TI) CC2541 BLE System-on-Chip for communication and processing. A Texas Instrument LM334, current source, applies 0.6 mA current between cathode and anode electrodes. A Texas Instrument LMP91000 (analog front end for chemical sensing) was used as the amperometric monitoring system for the alcohol sensor. A current of 600 uA is applied between the anode and cathode electrodes for 5 minutes. Afterwards, the CC2541 microcontroller disconnects the current source and activates the amperometric chip to measure the amperometric current for a potential cell of −0.2 V after 5 min delay. Then, the sensor information is transmitted in a 2-byte format to a Bluetooth 4.0-enabled reciever. A graphical interface has been developed using Python script language to demonstrate measurement results on a desktop or laptop. A Johanson Technology 2.45 GHz chip antenna (2450AT42A100) and impedance matched balun (2450BM15A0002) were employed for wireless transmission. Two 396/397 watch batteries (2×1.55 V, 33 mAh each) in series were utilized as a power source, regulated for the electronics via a TPS61220 boost converter and an LM4120 low-dropout voltage regulator.

Assembly and Characterization of Integrated Wireless Tattoo-Based Alcohol Sensor The first prototype of the fabricated flexible printed circuit board assembly, shown in FIG. 1A, measured 2 cm×5 cm. In the flexible PCB design, the holes were selectively plated inside so that the surface copper stays at 0.5 oz RA cu with no plated copper on top. That is in effort to minimize the possibility of cracking the traces while mishandling or bending the flex. Unlike the usual process, in which Polyimide cover layer is used for insulation, due to the complexity of the soldermask openings, LPI is employed to get a good registration. Then, Polyimide cover layer provides extra support for the surface copper when bending.

Rationale for Iontophoretic-Biosensing System of Tattoo-Based Alcohol Sensor

Each pair of alcohol tattoo sensor consists of iontophoretic electrode (anode and cathode) and amperometric sensing electrode (WE, RE, and CE) in anode compartment. Due to integration of both systems in one platform, specific electrode design was required. The iontophoretic electrodes are responsible for generating sweat by delivery of pilocarpine drug and thus positioned in the middle of sensing electrode component. Iontophoresis electrodes were covered with cryogel soaked with pilocarpine nitrate and sodium nitrate on anode and cathode, respectively, to deliver the chemicals though skin by applying constant current. The cryogel has large porous structure and biocompatible material offering effective sweat generation without any skin irritation and burning in our preliminary study. For amperometric sensing of alcohol in sweat, screen-printed Prussian-Blue transducer was utilized due to its high selectivity towards hydrogen peroxide, which is product of enzymatic reaction between alcohol oxidase (AOx) and alcohol. AOx was immobilized on working electrode with BSA, chitosan and then covered with agarose gel containing PBS ($K^+$) to provide enough electrolytes to run electrochemistry, especially potassium ion which is crucial ion to keep electron shuttling activity of Prussian-Blue.

Determination of Alcohol with Tattoo Sensor in Buffer Medium

Figure 12:
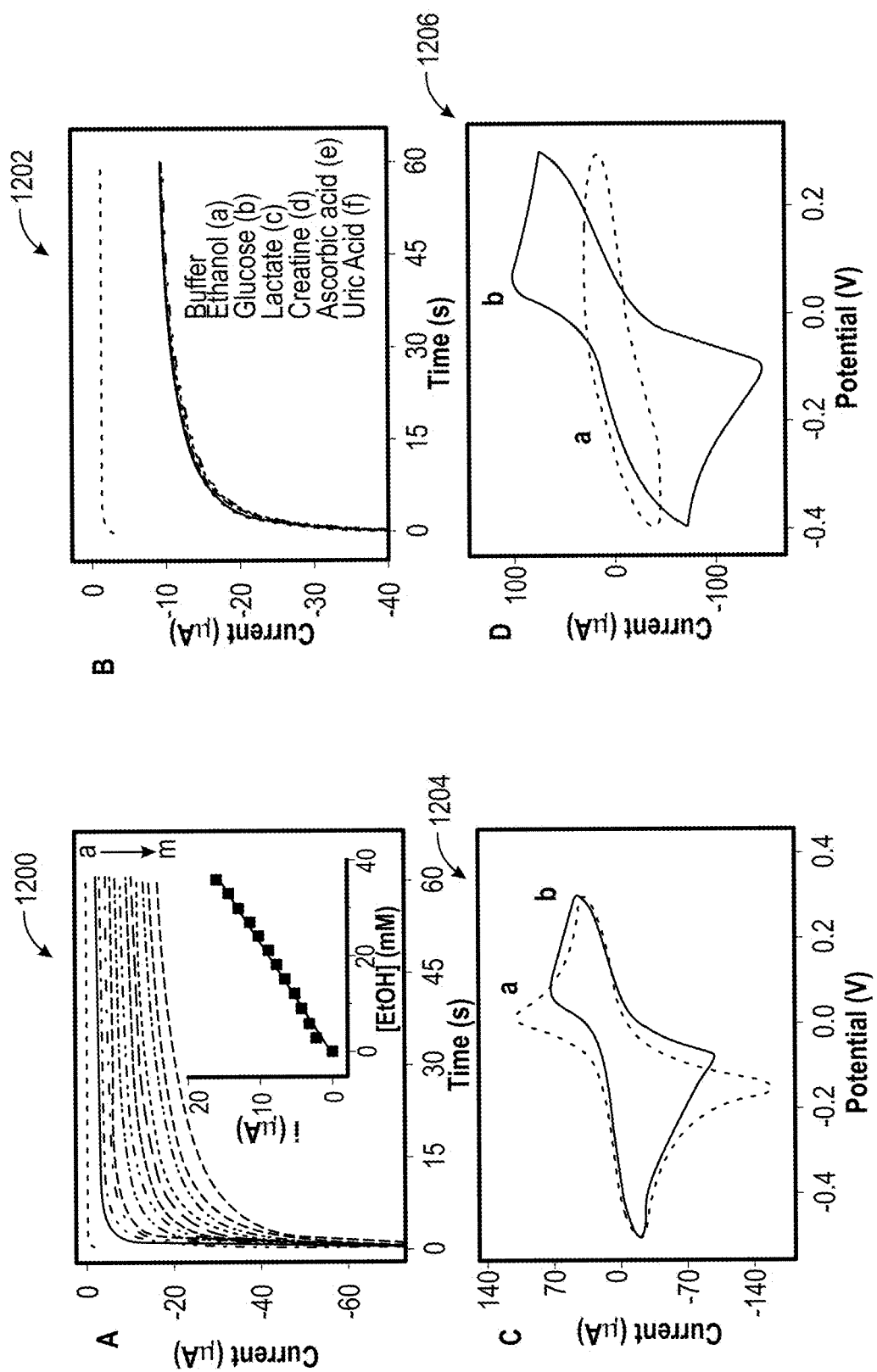
FIG. 12 shows exemplary results obtained using the disclosed non-invasive biosensor device implemented as a tattoo- or patch-based alcohol sensor.

First of all, the electrochemical performance of the alcohol biosensor was validated in buffer medium over a dynamic concentration range of 0-36 mM ethanol, which is physiological level in sweat. FIG. 12, part A displays well-defined chronoampemetric response to 3 mM increment (b-m) in buffer solution (1200). The resulting linear calibration plot is shown in the inset of FIG. 12, part A (slope, 0.441 µA/mM; correlation coefficient, $R^2$=0.992). Note that human sweat contains various physiological relevant interferents (glucose, uric acid, lactate, ascorbic acid, and creatine), selectivity towards ethanol should be tested for on-body operation and the result is shown in FIG. 12, part B (1202). High sensitivity and selectivity toward ethanol are demonstrated in FIG. 12 and these are attributed by efficient chemical modification of alcohol oxidase on Prussian blue working electrode and high selectivity of Prussian blue transducer towards hydrogen peroxide (product of enzymatic reaction) at low operational potential.

FIG. 12 shows exemplary results obtained using the disclosed non-invasive biosensor device implemented as a tattoo- or patch-based alcohol sensor. Specifically, FIG. 12 shows in part (A), chronoamperometric response of the tattoo-based alcohol sensor to increasing ethanol concentrations from 0 mM(a) to 36 mM(m) in buffer in 3 mM increments (1200). FIG. 12 shows in part (B), interference study in the presence of 10 mM ethanol (plot "a"), followed by subsequent additions of 0.2 mM glucose (plot "b"), 10 mM lactate (plot "c"), 84 µM creatine (plot "d"), 10 µM ascorbic acid (plot "e"), and 60 µM uric acid (plot "e". Potential step to −0.2 V (vs Ag/AgCl). Medium, phosphate-buffer (pH 7) (1202). FIG. 12 shows in part (C), cyclic voltammogram of the tattoo-based alcohol sensor in buffer solution (pH 7) and 1% pilocarpine dissolved buffer solution (pH 7) (1204). FIG. 12 shows in part (D), cyclic voltammogram of the tattoo-based bare prussian blue (PB) electrode and 2% agarose gel modified PB electrode in 1% pilocarpine solution (dissolved in DI water) (1206).

On-Body Alcohol Monitoring on Human Subject

After evaluation of the tattoo sensor performance in vitro, we tested on-body operation of alcohol tattoo sensor with human subjects. First, detection ability of the alcohol tattoo sensor is confirmed under consumption of alcoholic beverage. FIG. 13 A shows on-body results obtained by three different subjects with alcohol ingestion following the protocol described in experimental approach section (1300, 1302, 1304). Amperometric responses were compared between before and after drinking alcohols, showing distinct current signal increment caused by spike of alcohol level in sweat along with its level in blood over all three subjects. As described, second amperometric response (after drinking) was measured after 20 min of alcohol consumption and BAC is measured at the same time with amperometric measurement. Even though three subjects were asked to take same amount of alcohols, the BAC values and current responses are different among subjects after the given time of period, implying each subject has different digestion rate of alcohol. None of the subjects reported perceptible discomfort during these on-body measurements. Three control experiments (no drinking, no enzyme modification, and no iontophoresis) were performed to verify false alarm from on-body results obtained under alcohol consumption. None of control experiments showed current difference. In detail, the data from control experiment without enzyme modification clearly demonstrates high specificity of alcohol tattoo sensor toward alcohol in sweat. It can be clearly noted from control experiment without drinking (FIG. 13B (1306, 1308, 1310)), that the current response, shown in FIG. 13A (1300, 1302, 1304), is caused by alcohol consumption and performing iontophoresis process doesn't affect any amperometric current signal, even though remained amount of pilocarpine nitrate has changed due to delivery of pilocarpine. The last control experiments in the absence of iontophoresis also showed no current differences although BAC was spiked up to 0.0018% from alcohol ingestion. It implies that current responses shown in FIG. 13A (1300, 1302, 1304) are from alcohol in generated sweat by iontophoresis not from other source/environment.

Figure 13A:
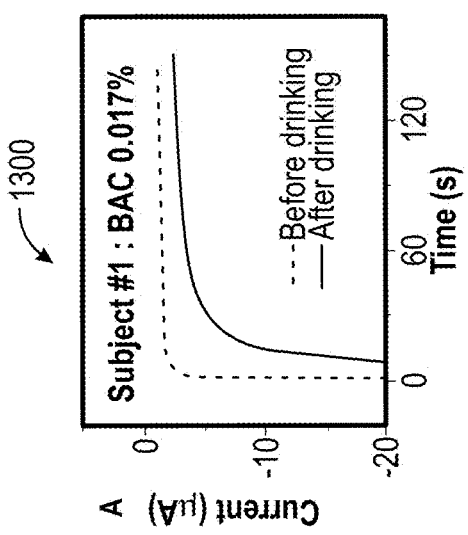
FIGS. 13A-B represent amperograms obtained using the disclosed noninvasive alcohol sensing from human subjects wearing the disclosed alcohol tattoo sensor.
Figure 13A:
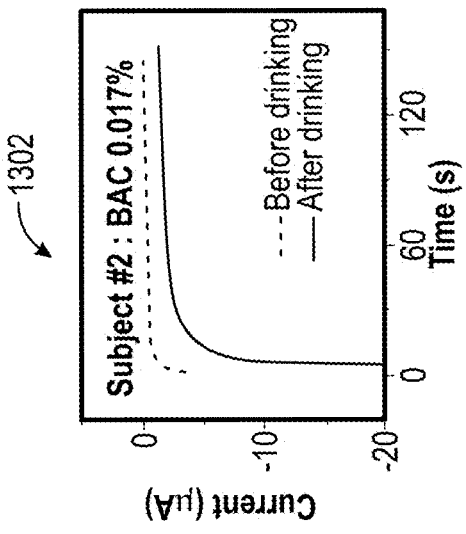
Figure 13A:
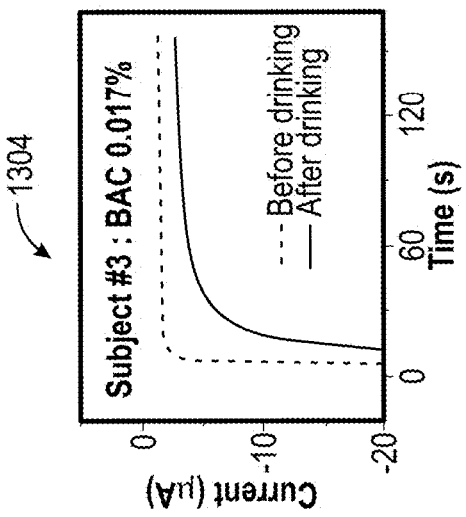
Figure 13B:
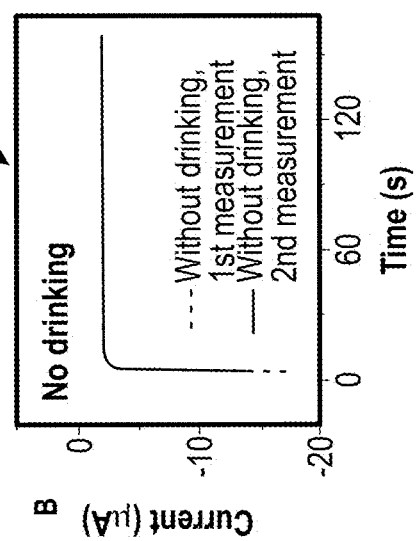
Figure 13B:
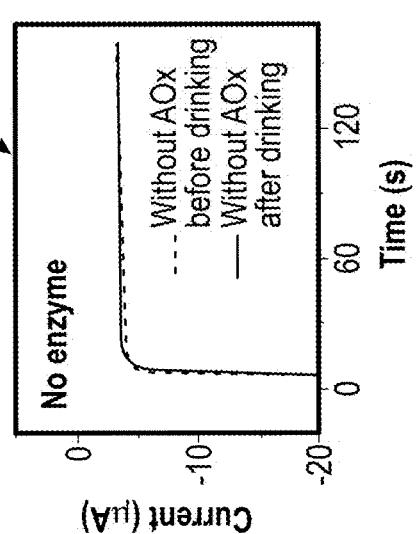
Figure 13B:
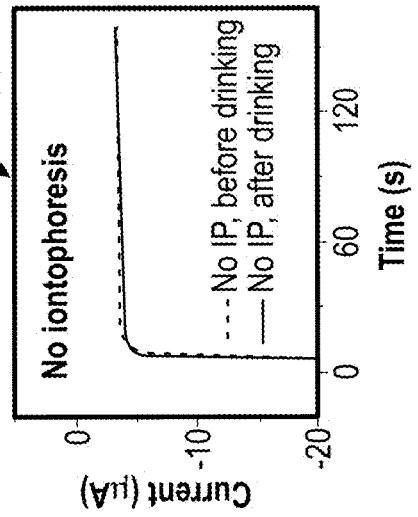

Specifically, FIGS. 13A-B represents amperograms obtained using the disclosed noninvasive alcohol sensing from human subjects wearing the disclosed alcohol tattoo sensor. Specifically, FIG. 13 (A) shows experiments with consumption of 12 oz. of beer measured before and after drinking alcohol beverage from three subjects (1300, 1302, and 1304). FIG. 13 (B) shows control experiments without drinking (left 1306), without enzyme immobilization (middle 1308), and without iontophoresis (right 1310). Blood alcohol level is obtained by a breathalyzer. In FIG. 13, data were collected under potential step to −0.2 V (vs Ag/AgCl).

Figure 13C:
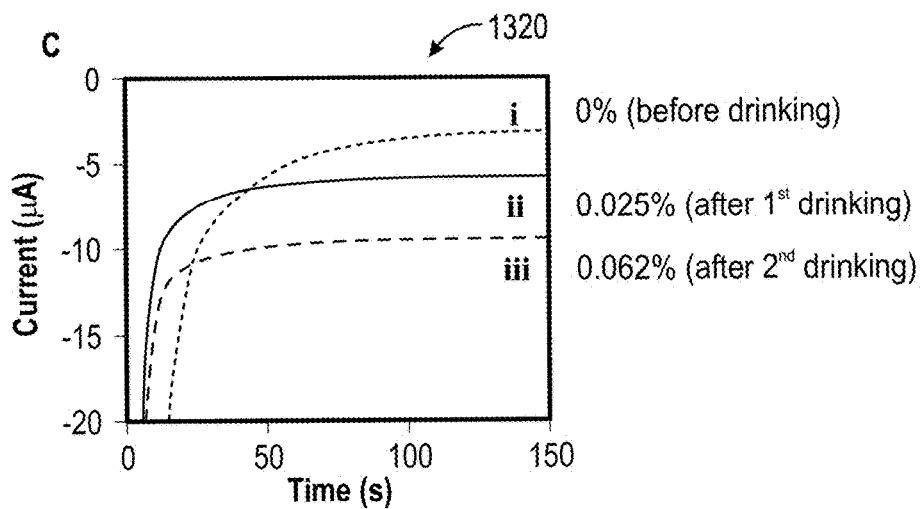
FIG. 13C shows exemplary Amperograms obtained for noninvasive alcohol detection obtained from human subjects wearing the alcohol tattoo sensor showing correlation between BAC level and current response from tattoo biosensor measured before (i, BAC: 0%) and after drinking 5 oz. of wine (ii, BAC: 0.0025%)) and 10 oz. of wine (iii, BAC: 0.0062%)).
Figure 13D:
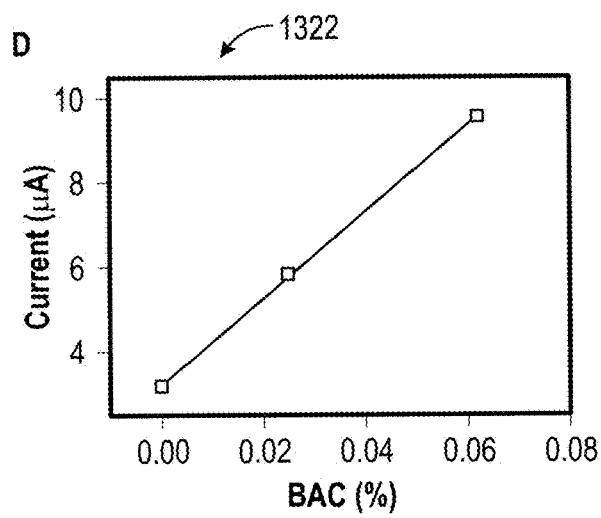
FIG. 13D shows resulting linear plot between current response and BAC level.

Next, additional on-body experiments are performed to evaluate correlation between BAC (obtained from breathalyzer) and current response from our alcohol tattoo sensor with serial ingestion of alcohol drinks. As illustrated in FIG. 13C, first current response was obtained corresponds to BAC 0.00% (before drinking) and followed by two sets of drinking and measurement procedures using same electrode (1320). After $1^{st}$ alcohol consumption, BAC turned out 0.025% showing distinct current response, and BAC was increased to 0.062% after $2^{nd}$ drinking with further increased amperometric current signal. The resulting plot between BAC and current value is shown in FIG. 13D (1322). The current response displays great linearity toward BAC level (slope, 102 µA/BAC %; correlation coefficient, $R^2$=0.999). This implies that the current response is responsible for ethanol level in sweat, which is well-correlated with BAC.

Specifically, FIG. 13C shows exemplary Amperograms obtained for noninvasive alcohol detection obtained from human subjects wearing the alcohol tattoo sensor showing correlation between BAC level and current response from tattoo biosensor measured before (i, BAC: 0%) and after drinking 5 oz. of wine (ii, BAC: 0.0025%)) and 10 oz. of wine (iii, BAC: 0.0062%)). Blood alcohol level is obtained by breathalyzer. Potential step to −0.2 V (vs Ag/AgCl). FIG. 13D shows resulting linear plot between current response and BAC level.

Characterization of Integrated Flexible Wireless Tattoo-Based Alcohol Sensor

Figure 13E:
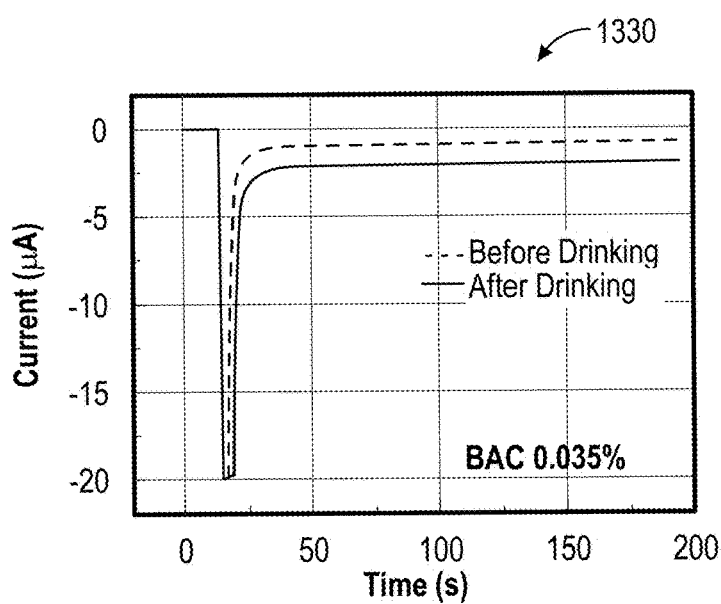
FIG. 13E shows integration of flexible wireless circuit board with alcohol tattoo sensor.

The practical use of wearable biosensors for real-time monitoring has been hindered by the lack of the development of a body-compliant wireless circuit board. For realization of wearable alcohol sensor, a flexible wireless circuitry was custom-made and integrated with our developed sensor (shown in FIG. 11, part A). Performance of the integrated wearable device was evaluated following the same protocol as previous on-body experiments. A BLE-enabled printed circuit board employed iontophoresis by applying 0.6 mA current and measured amperometry at −0.2 V for 150 seconds. The current response was sampled with a frequency of 1 Hz, and transmitted in real time via Bluetooth 4.0 to a laptop/mobile device and plotted on screen with graphical interface developed using Python. The resulting plot is shown in FIG. 13E obtained by wireless transmission showing clear current difference after consumption of alcohol beverage and the data corresponds to previous on-body results obtained from lab-scale potentiostat. This test provides the evidence for the practicality of the wireless alcohol tattoo sensor towards monitoring BAC.

Specifically, FIG. 13E shows integration of flexible wireless circuit board with alcohol tattoo sensor. Amperograms obtained by the wireless integrated alcohol tattoo sensor from human subjects measured before and after taking alcohol beverage. BAC was confirmed as 0.035% by breathalyzer. Potential step to −0.2 V (vs Ag/AgCl).

In this patent document, 'AlcoTatt', skin-worn tattoo-based wearable electrochemical biosensors are disclosed for noninvasive alcohol monitoring. Based on well-established correlation between ethanol concentration in sweat and blood, AlcoTatt measures alcohol concentration in sweat to estimate BAC, allowing non-invasive monitoring of BAC in real-time. The in vitro characterization of the tattoo sensors revealed their ability to detect alcohol in sweat covering physiological range in the presence of common interfering chemical species. On-body evaluation of the tattoo-based iontophoretic-biosensing platform further demonstrated the ability to detect the rise in the ethanol level after consumption of alcohol beverage in a noninvasive fashion. The new tattoo alcohol sensor has been coupled with flexible printed circuit board for wireless data collection in real-time. The disclosed 'AlcoTatt' allows non-invasive, passive and simple monitoring of BAC, which can be useful for checking driver's ethanol ingestion or individuals who need to keep abstinence of alcohol.

Alcohol Tattoo Sensor Designs

Figure 14:
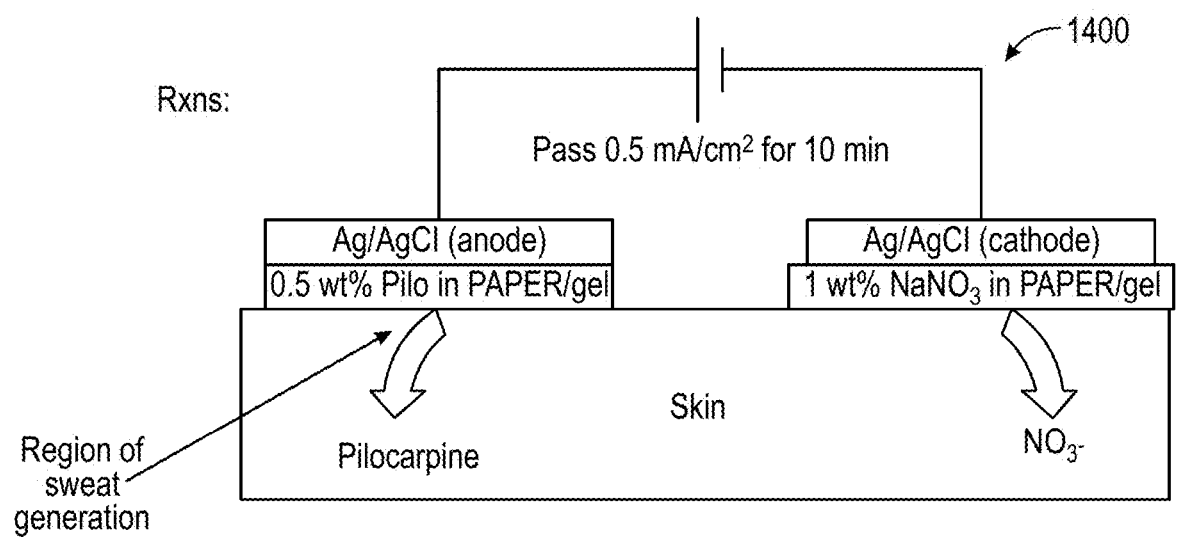
FIG. 14 shows an exemplary Pilocarpine Induced Sweat Generation using an exemplary alcohol tattoo sensor device.

The disclosed technology can be implemented as alcohol tattoo sensor devices. FIG. 14 shows an exemplary Pilocarpine Induced Sweat Generation using an exemplary alcohol tattoo sensor device 1400. In FIG. 14, the Pilocarpine Induced Sweat Generation was performed using a Pilocarpine Soaked in Filter Paper. Table 1 shows exemplary amounts of sweat generated during 10 min collection time.

TABLE 1

Amount of sweat generated during 10 min collection time

|  | Before (mg) | After (mg) | Difference |
|---|---|---|---|
| Un-stimulated | 32.94 | 33.5 | 0.56 |
| Stimulated | 31.45 | 82.55 | 51.6 |

Figure 15:
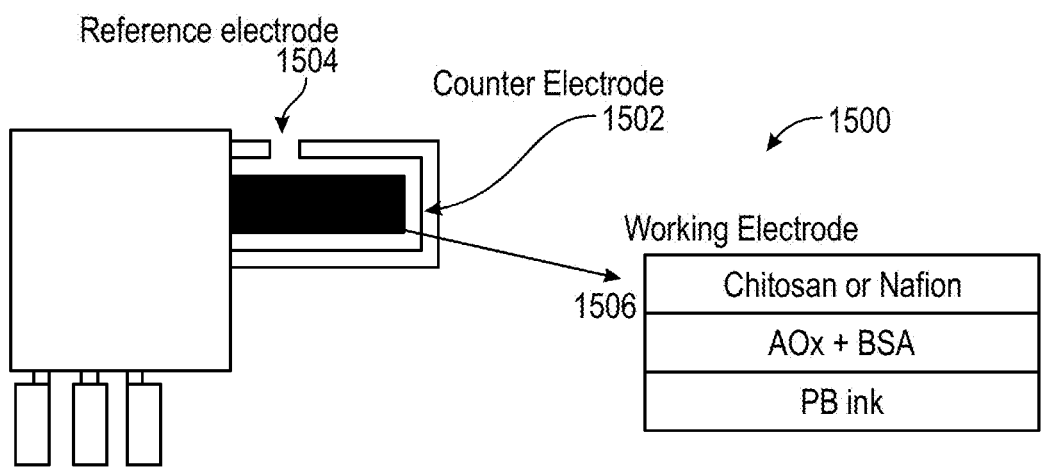
FIG. 15 shows an exemplary on-tattoo electrode.

FIG. 15 shows an exemplary on-tattoo electrode 1500. An iontophoresis electrode is used as counter electrode 1502. The on-tattoo electrode 1500 also includes a reference electrode 1504 and a working electrode 1506. When the electrode 1500 is oxidized, the color changes to black, for example. The on-tattoo was tested at −0.2V with 1 min incubation to obtain an EtOH response. The on-tattoo can be optimized in terms of potential, and enzyme amount.

Figure 16:
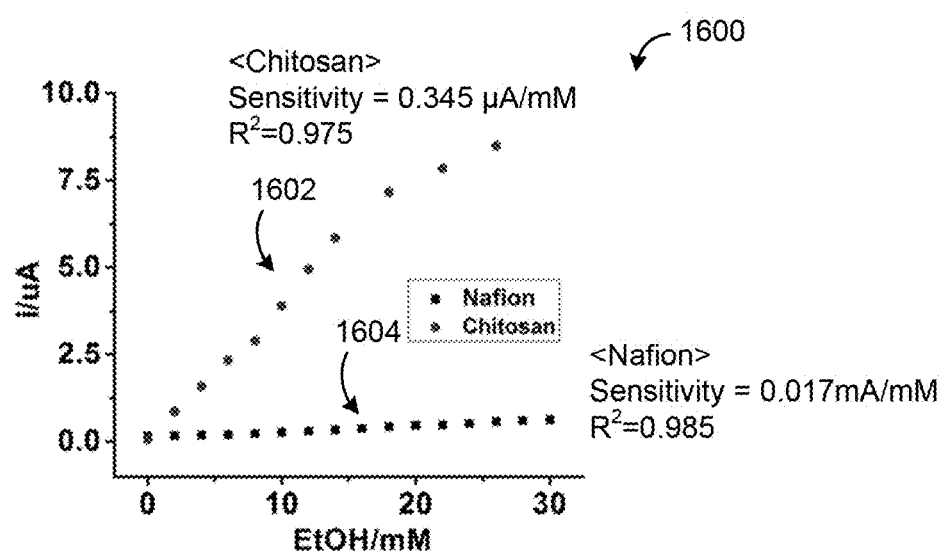
FIG. 16 shows exemplary data on alumina SPE_EtOH detection.

FIG. 16 shows exemplary data on alumina SPE_EtOH detection (1600). The data 1600 was obtained for Chitosan (1602) and Nafion (1604).

Figure 17:
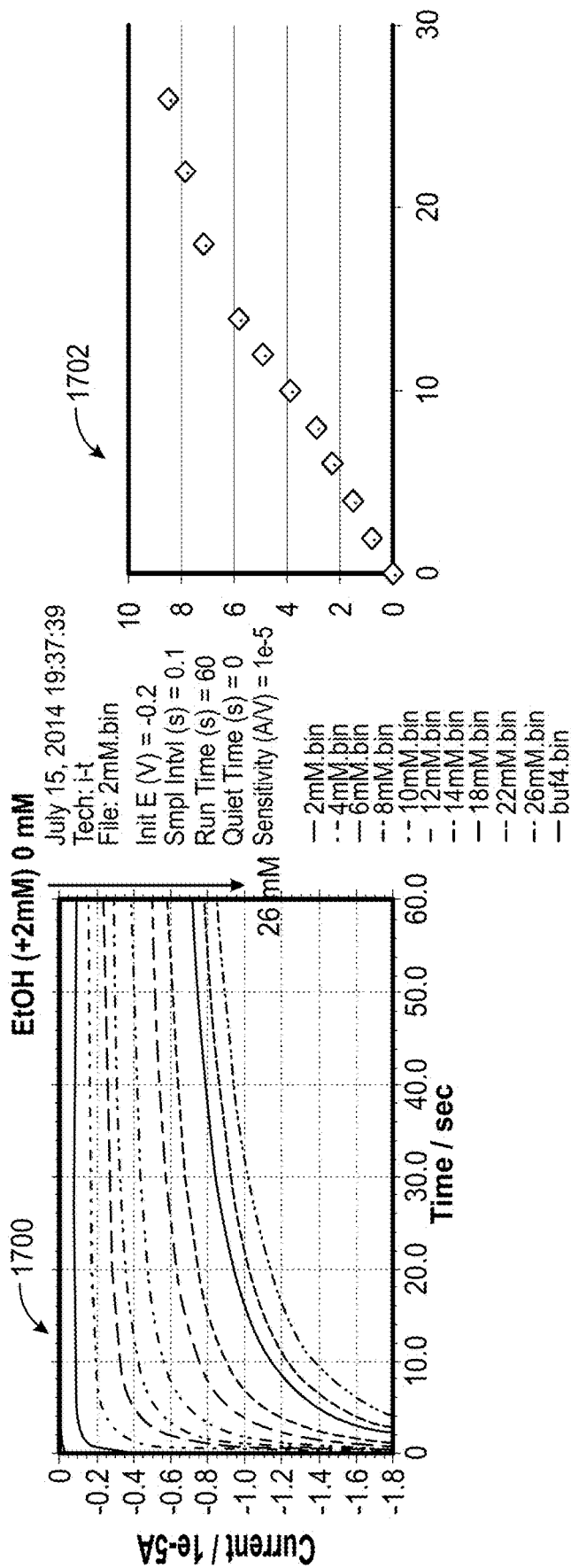
FIG. 17 shows exemplary data on EtOH detection on Alumina substrate (PG design).

FIG. 17 shows exemplary data 1700 and 1702 on EtOH detection on Alumina substrate (PG design). The data was obtained under electrode modification that includes 1 mL of (2.5 mL of (AOx 20 U/mL+BSA 10 mg/mL)+0.5 mL Chitosan 0.5% v:v). Working and counter electrodes include PB carbon material. The reference electrode includes Ag/AgCl.

Figure 18:
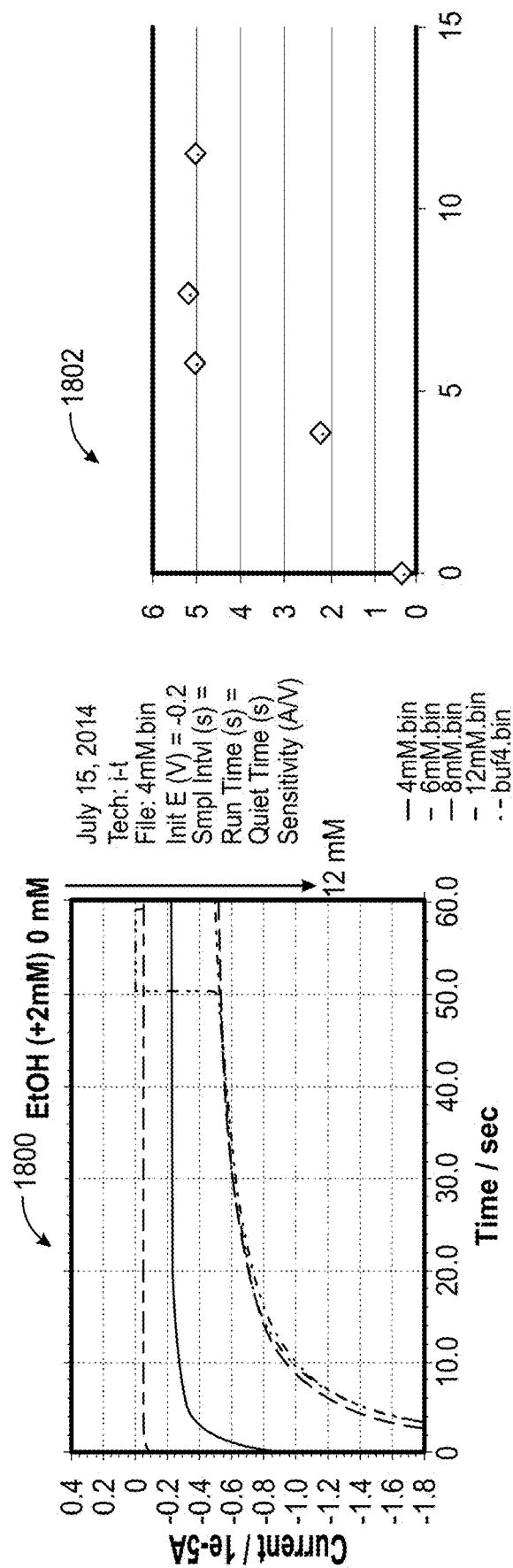
FIG. 18 shows exemplary data on EtOH detection on Tattoo paper.

FIG. 18 shows exemplary data 1800 and 1802 on EtOH detection on Tattoo paper. The working electrode includes PB carbon while the reference and counter electrodes include Ag/AgCl. At the working electrode, reduction current occurs, at the same time, silver counter electrode is easily oxidized.

Figure 19:
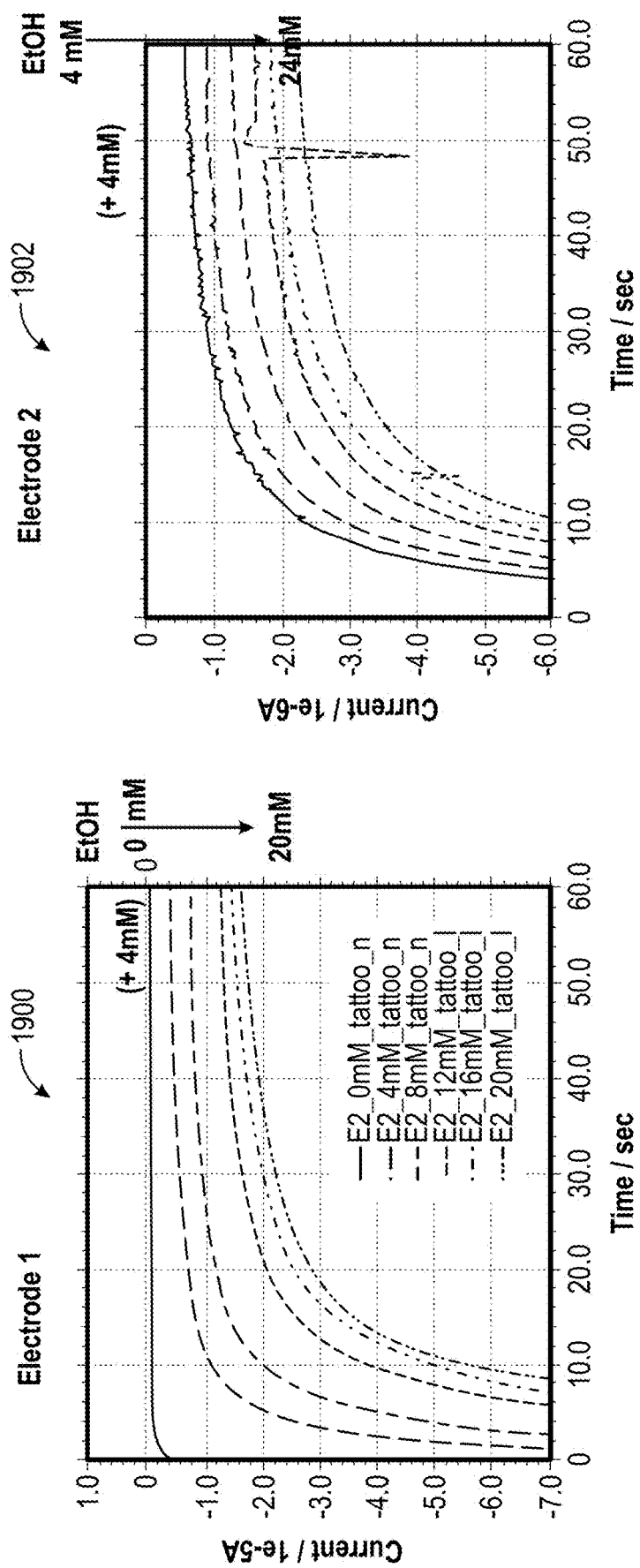
FIG. 19 shows data for exemplary EtOH detection with Std.3 design on tattoo (PG stencil).

FIG. 19 shows data for exemplary EtOH detection with Std.3 design on tattoo (PG stencil) 1900 and 1902. The working and counter electrodes were PB carbon and only the reference electrode was Ag/AgCl. The data 1900 and 1902 were obtained under the working electrode modification of 1 mL of (2.5 mL of (AOx 20 U/mL+BSA 10 mg/mL)+0.5 mL Chitosan 0.5% v:v). Troubleshooting can be performed by changing the Counter Electrode to PB carbon instead of Ag/AgCl. Consequently, the Current signal is in a better shape showing linear response to ethanol concentration.

Figure 20:
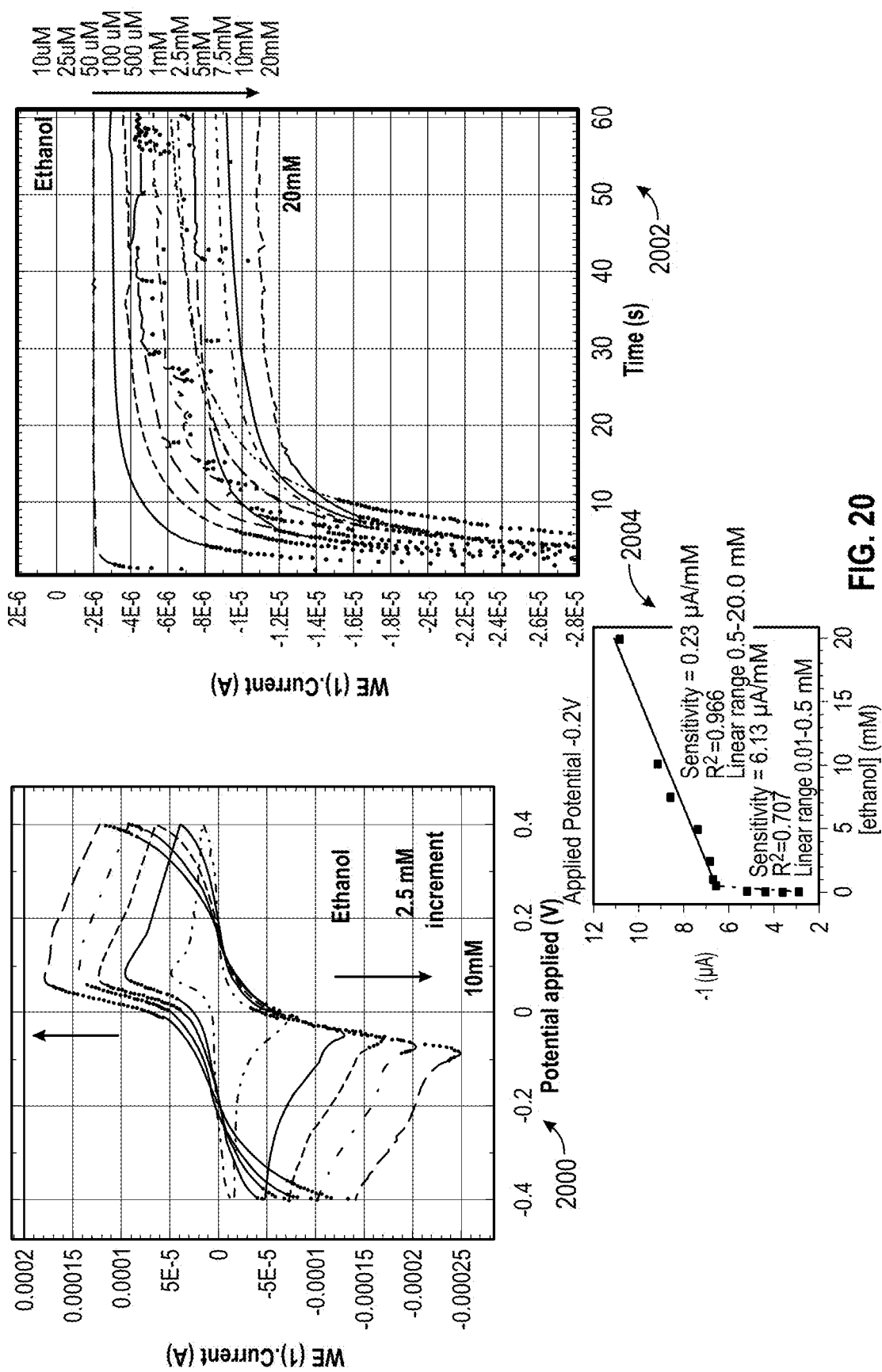
FIG. 20 shows data for exemplary EtOH detection with Std.3 design on tattoo (PG stencil).

FIG. 20 shows data 2000, 2002, and 2004 for exemplary EtOH detection with Std.3 design on tattoo (PG stencil). The working electrode and the counter electrodes were PB carbon and only the reference electrode was Ag/AgCl. The data 2000, 2002, and 2004 were obtained with working electrode modification of (Aox+BSA)+0.5% Chitosan: double-layer. For amperometry, applied potential was −0.2V. The data recording protocol included 0.1 M phosphate buffer (pH 7.4) and 50 mV/s, 2nd cycle.

The blood alcohol content (BAC) can be calculated based on the sweat ethanol concentration using Equation 1. For example, 0.01% BAC=0.04 mM EtOH in sweat and 0.08% BAC=0.35 mM EtOH in sweat.

$$BAC(gL^{-1})=0.71 \times sweat\ ethanol\ concentration\ (gL^{-1})$$
$$(r=0.9). \qquad Eq.\ 1$$

According to a DMV BAC regulation, 0.01% BAC (0.04 mM EtOH) should be detectable. To perform alcohol sensing, carbon counter can be used rather than Ag/AgCl. EtOH affects tattoo paper substrate, and the amperometric response can be unstable due to bad connection. Additional insulator layer can be printed on tattoo paper, or on PET substrate to address the issue.

Figure 21:
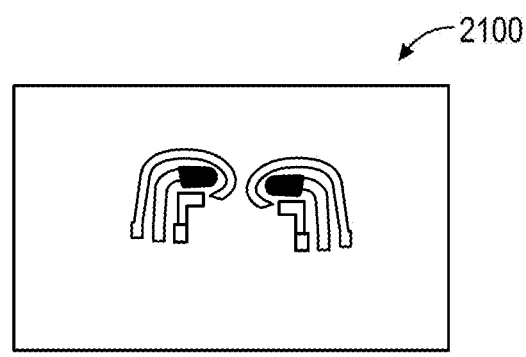
FIG. 21 shows an exemplary tattoo substrate.

FIG. 21 shows an exemplary tattoo substrate 2100. Ethanol may damage the tattoo paper layer. Troubleshooting can be performed by transferring the tattoo electrode on petri dish (or plastic substrate) and consequently the electrode is working fine.

Figure 22:
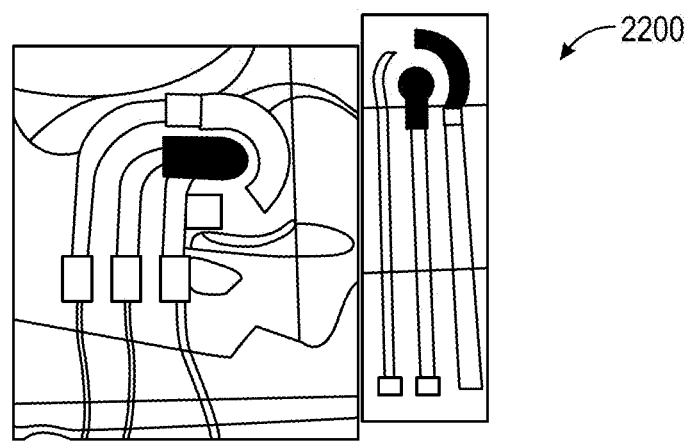
FIG. 22 shows exemplary electrode design and system for 2E and 3E systems.

FIG. 22 shows exemplary electrode design and system for 2E and 3E systems 2200. An exemplar glucose sensing tattoo device design can include 1 silver iontophoresis electrode (Big)+2E-system for Glucose detection. The ability of the 2E system to detect ethanol effectively can be affected when the reference electrode, counter electrode, or both are oxidized. When the iontophoresis electrode is used as the counter electrode, the silver counter electrode may still be oxidized because it is easily oxidized. The 3E system with Prussian Blue carbon electrode is more effective for Ethanol system because the Prussian Blue carbon electrode is not easily oxidized. Potential solutions can include (1) adding a carbon counter electrode on the glucose tattoo design; (2) adding an iontophoresis electrode (Silver) on PG stencil; or (3) making a new design for ethanol sensor.

Figure 23:
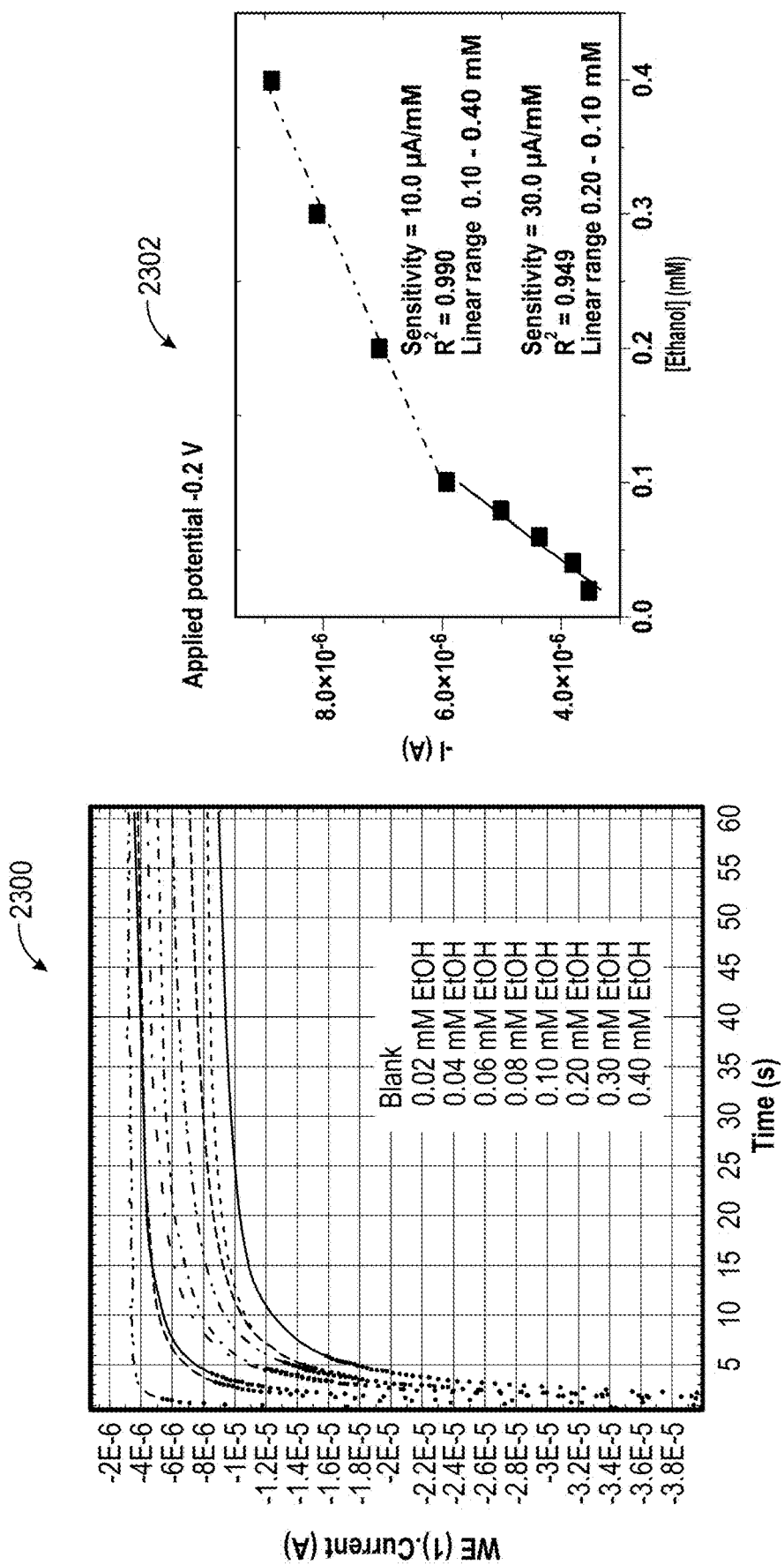
FIG. 23 shows data from an exemplary glucose tattoo electrode with 3E system (Silver counter and ref electrode.)

FIG. 23 shows data 2300 and 2302 from an exemplary glucose tattoo electrode with 3E system (Silver counter and ref electrode.) The data 2300 and 2302 were obtained under enzyme modification of Aox+BSA+Chitosan (1 layer) E=−0.2V incubation 1 min.

Figure 24:
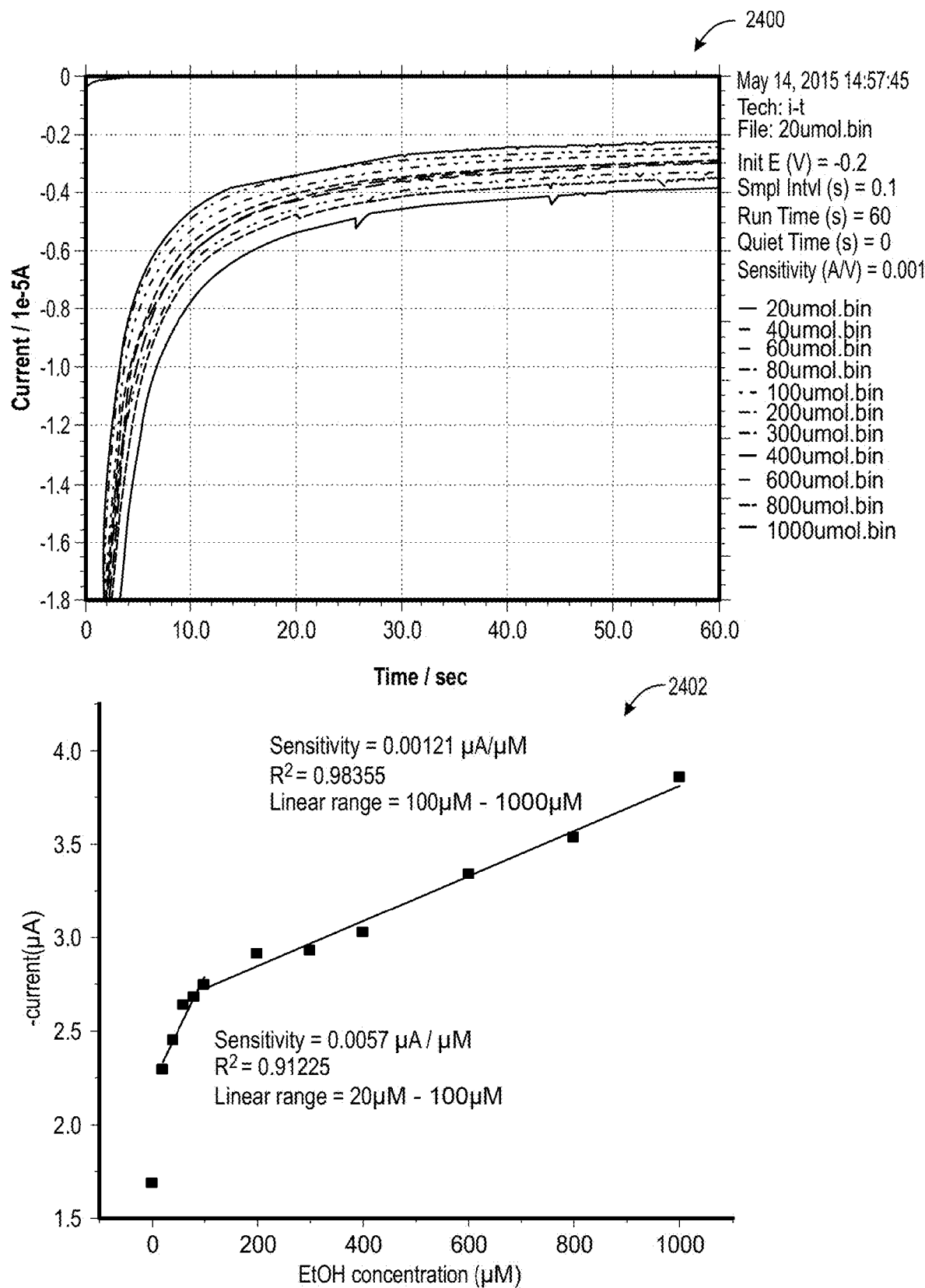
FIG. 24 shows data obtained from an exemplary PG tattoo Electrode with 3E system (Prussian Blue carbon electrode as the counter electrode).

FIG. 24 shows data 2400 and 2402 obtained from an exemplary PG tattoo Electrode with 3E system (Prussian Blue carbon electrode as the counter electrode). The data 2400 and 2402 were obtained under enzyme modification of Aox+BSA+Chitosan (1 layer) E=−0.2V incubation 1 min. FIG. 24 shows the response to 1 mM.

As shown above, using the proper tattoo design for Ethanol detection is crucial. In addition, enzyme modification can be optimized to obtain a good linear range in physiological level.

Figure 25:
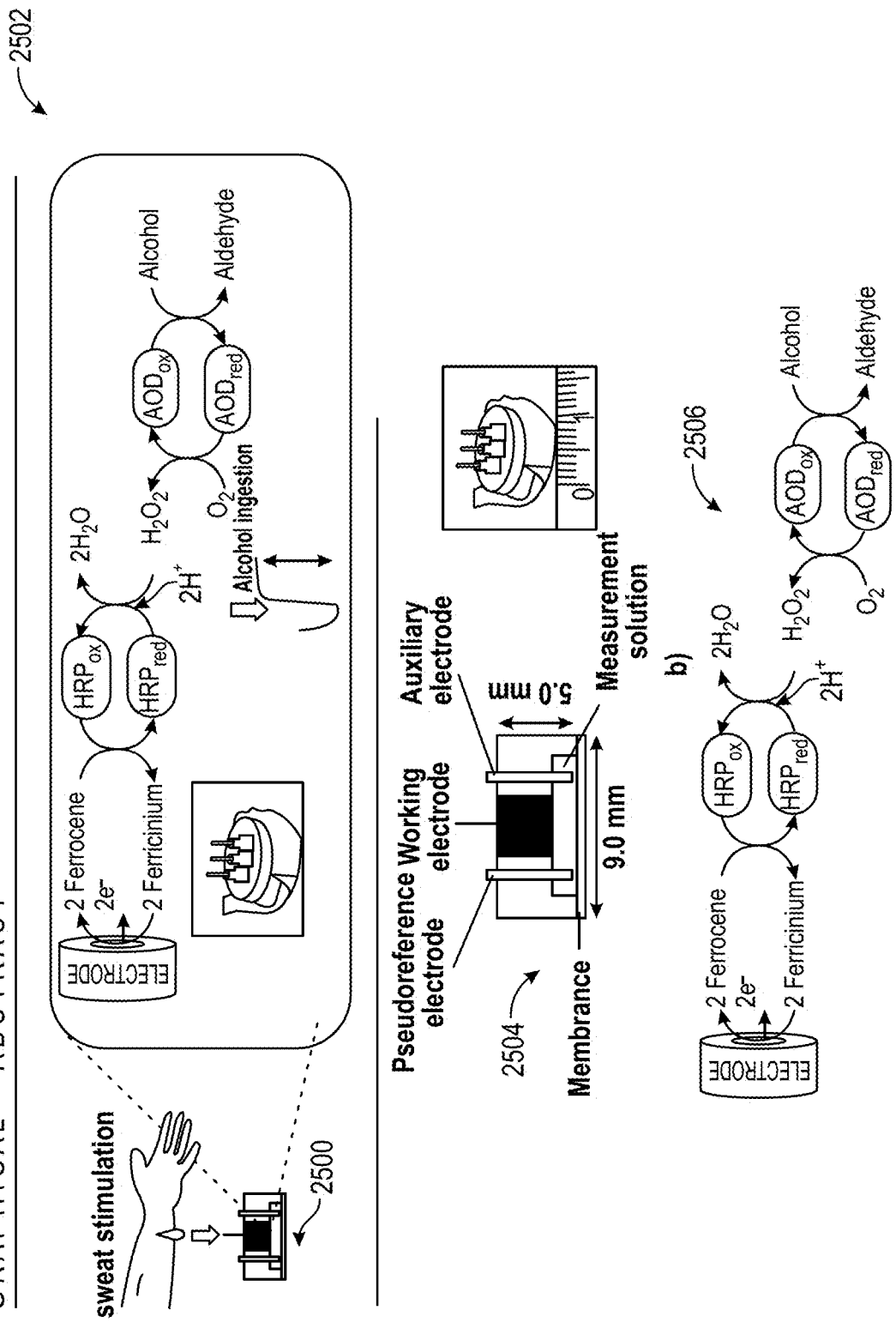
FIG. 25 shows schematic diagrams and real images displaying an exemplary biodevice and enzyme and electrode reactions involved in the response of graphite-Teflon-AOD-HRP-ferrocene.

FIG. 25 are schematic diagrams and real images displaying an exemplary biodevice (2500, 2504) and enzyme and electrode reactions involved in the response of graphite-Teflon-AOD-HRP-ferrocene (2502, 2506).

Figure 26:
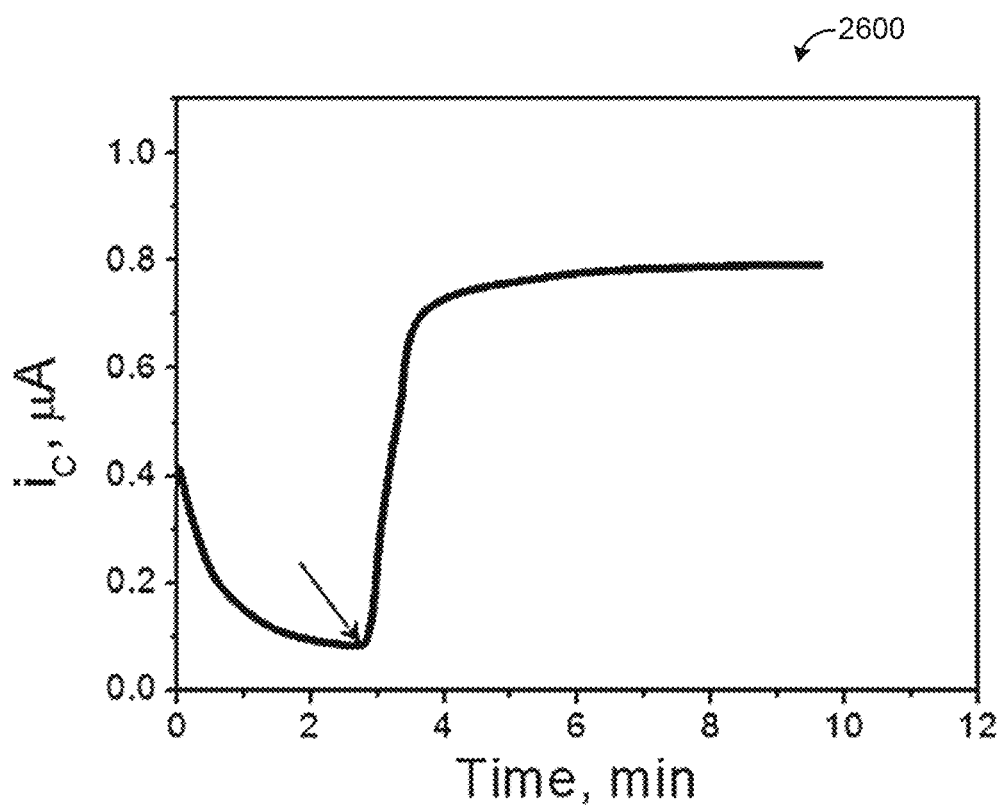
FIG. 26 shows an exemplary amperometric trace measured with an exemplary biodevice at 0.00V depicted for a $5.0 \times 10^{-4}$ molL$^{-1}$ ethanol solution.

FIG. 26 shows an exemplary amperometric trace 2600 measured with an exemplary biodevice at 0.00V depicted for a $5.0 \times 10^{-4}$ molL$^{-1}$ ethanol solution.

Figure 27:
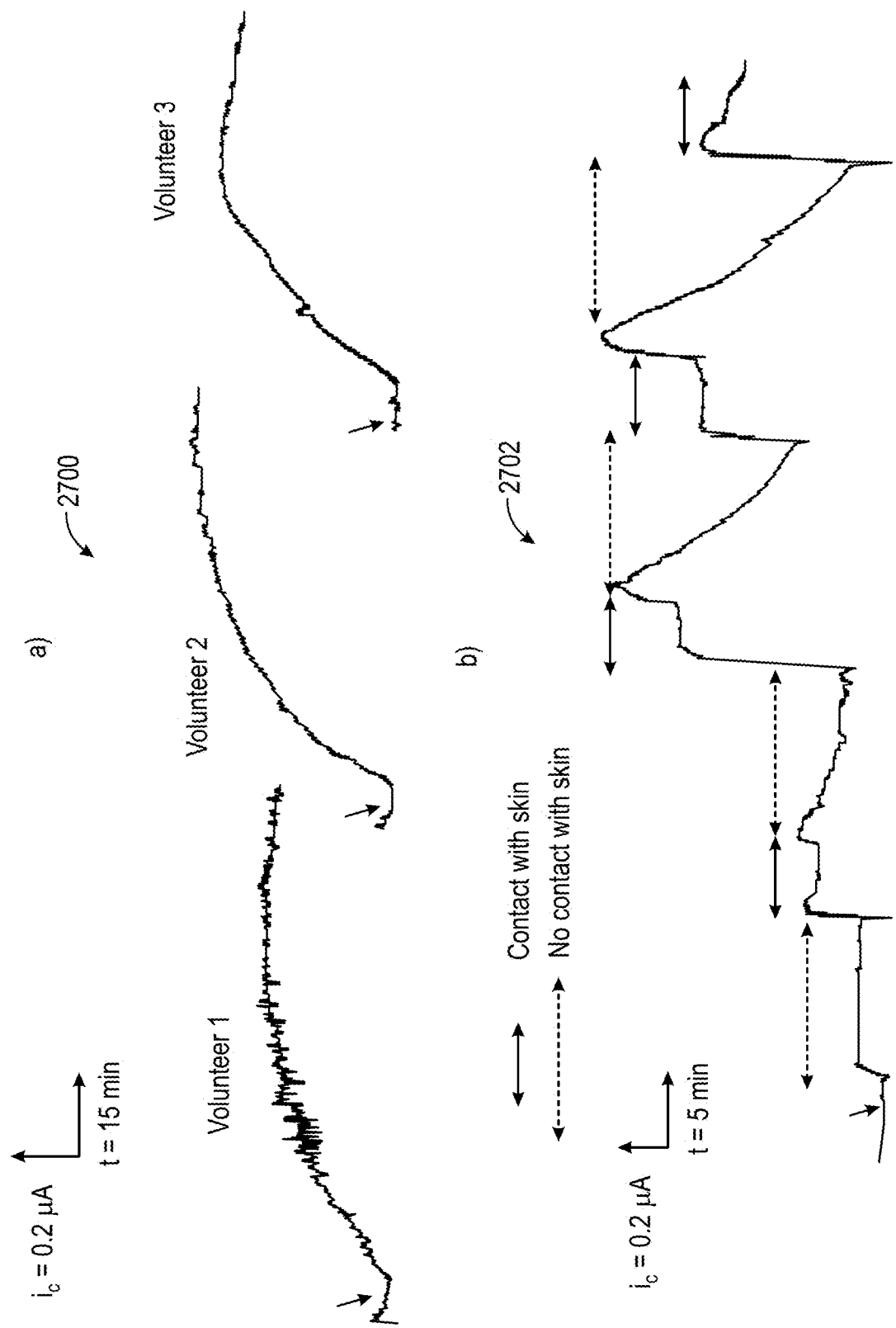
FIG. 27 show exemplary current-time recording obtained after alcohol ingestion by placing a biodevice on the skin: continuous mode recording for three different volunteers and single measurements carried out for one volunteer.

FIG. 27 show exemplary current-time recording obtained after alcohol ingestion by placing a biodevice on the skin: continuous mode recording for three different volunteers (2700) and single measurements carried out for one volunteer (2702). In FIG. 27, the $E_{app}$=0.00V.

Figure 28:
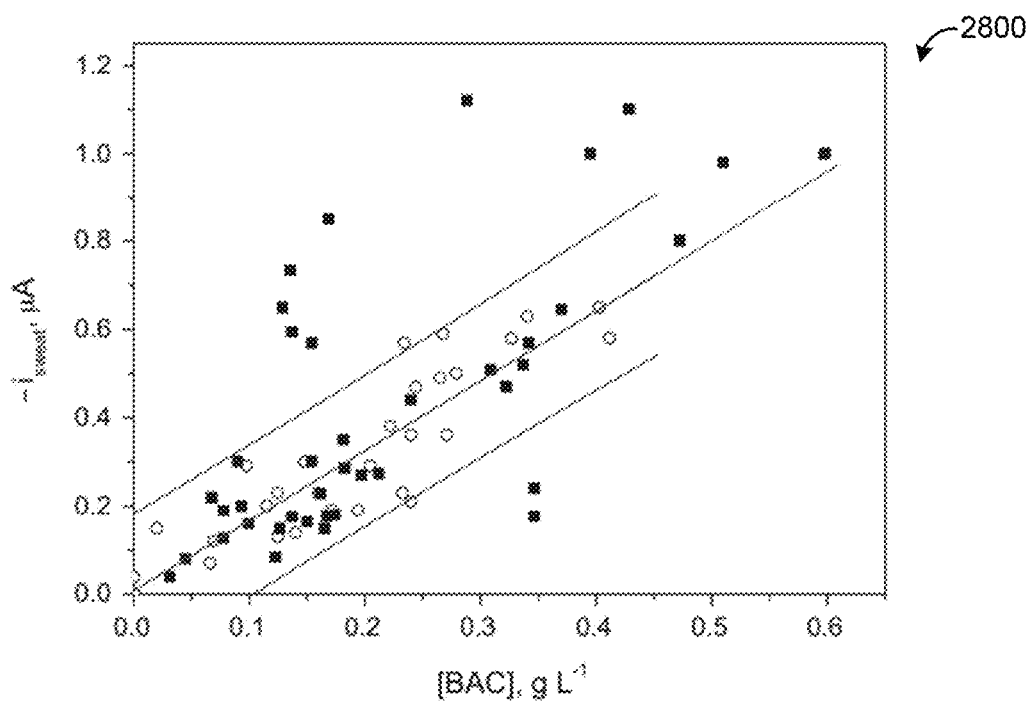
FIG. 28 shows exemplary correlation data between the cathodic current values measured with an exemplary biodevice.

FIG. 28 shows exemplary correlation data 2800 between the cathodic current values measured with an exemplary biodevice in the single measurement mode for 40 volunteers (filled square) as well as others (open circle) vs. the BAC values determined by gas chromatography. Calibrating straight line prediction intervals are shown as solid lines.

Figure 29:
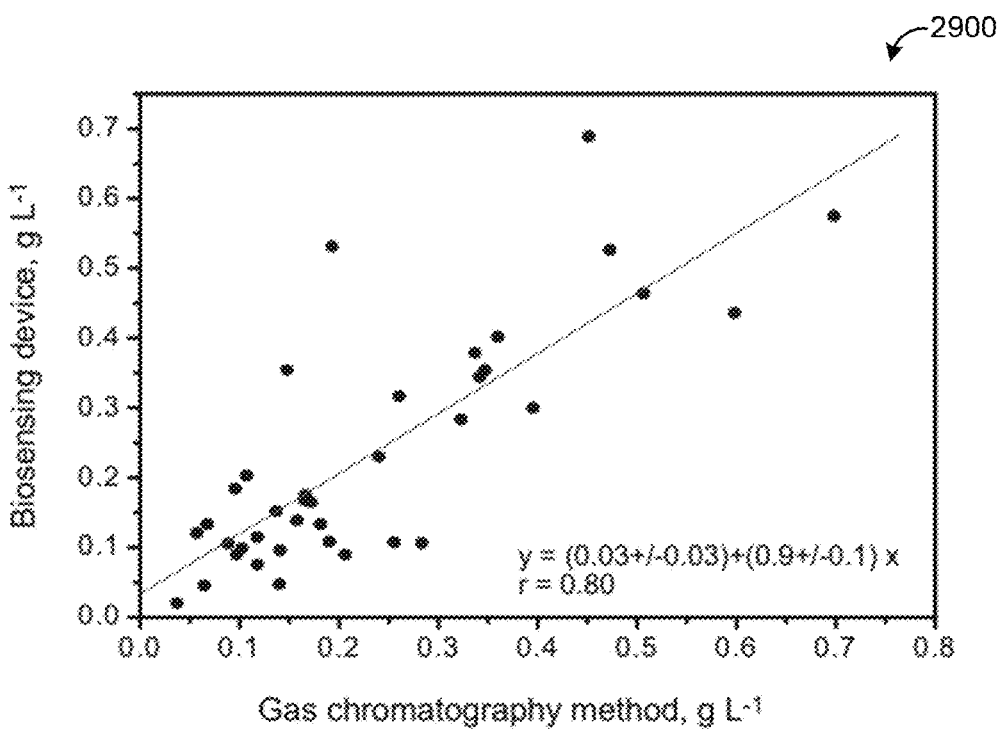
FIG. 29 shows exemplary least square straight line regression data.

FIG. 29 shows least square straight line regression data 2900 resulting by plotting the BAC values in $gL^{-1}$ obtained with the biodevice measuring in sweat and the gas chromatography reference method.

Figure 30:
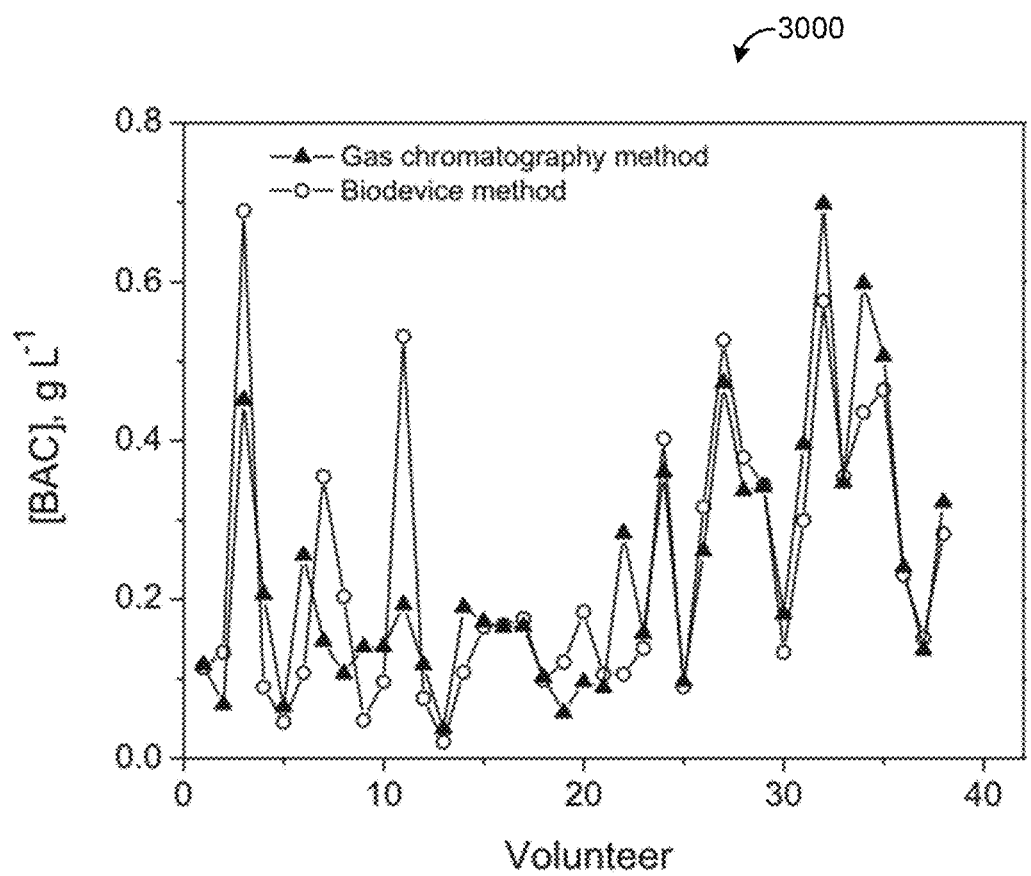
FIG. 30 shows a comparison data of the BAC values obtained with the biodevice through sweat measurements and with the gas chromatography method.

FIG. 30 shows a comparison data 3000 of the BAC values obtained with the biodevice through sweat measurements and with the gas chromatography method.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

Additional information pertaining to the disclosed technology is described below.

Wearable Electrochemical Sensors

In some implementations, the disclosed technology can be applied to wearable sensors. Sensors based on electrochemical processes can be used to detect a chemical, substance, a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

Techniques, systems, and devices are described for fabricating and implementing electrochemical biosensors and chemical sensors that are wearable on skin or a wearable item, e.g., by a procedure analogous to the transfer of a temporary tattoo.

In one aspect of the disclosed technology, a method of producing an epidermal biosensor includes forming an electrode pattern onto a coated surface of a paper-based substrate to form an electrochemical sensor, the electrode pattern including an electrically conductive material and an electrically insulative material configured in a particular design layout, and attaching an adhesive sheet on a surface of the electrochemical sensor having the electrode pattern, the adhesive sheet capable of adhering to skin or a wearable item, in which the electrochemical sensor, when attached to the skin or the wearable item, is operable to detect chemical analytes within an external environment.

Implementations of the method can optionally include one or more of the following features. For example, in some implementations of the method, the adhesive sheet can include an outer coating layer on an external surface of the adhesive sheet not in contact with the electrode pattern. For example, the outer coating layer can include polyvinyl alcohol (PVA). In some implementations, for example, the method can further include removing the outer coating layer from the adhesive sheet to enable adhesion of the electrochemical sensor to the skin or the wearable item via the adhesive sheet. Also for example, the method can further include removing the paper-based substrate from the electrochemical sensor to expose the electrode pattern to the external environment. For example, the coated surface can include a release agent material including cellulose acetate. For example, the adhesive sheet can include polydimethylsiloxane (PDMS). In some implementations of the method, the forming can include performing screen printing, aerosol deposition, or inkjet printing the electrode pattern onto the coated surface of the paper-based substrate. For example, the electrically conductive material can include a conductive ink, e.g., including, but not limited to, gold, platinum, nickel, copper, silver, and/or silver chloride. For example, the electrically insulative material can include a nonconductive ink, e.g., including, but not limited to, polyethylene terephthalate (PET), polystyrene (PS), polyester (PE), and/or polytetrafluoroethylene (PTFE). In some examples, the electrode pattern can further include an electrically semi-conductive material. For example, the electrically semi-conductive material can include a semi-conductive ink, e.g., including, but not limited to, amorphous carbon, carbon black, graphite, carbon nanotubes, and/or graphene. In some implementations of the method, for example, the electrode pattern further can include carbon fiber segments dispersed within the electrically conductive or electrically semi-conductive material.

In another aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, attaching an adhesive sheet on a surface of the electrochemical sensor having the electrode pattern, the adhesive sheet capable of adhering to skin or a wearable item and structured to include a coating layer on an external surface of the adhesive sheet, and removing the paper-based substrate from the electrochemical sensor to expose the electrode pattern, in which the electrochemical sensor, when attached to the skin or the wearable item, is operable to detect a substance present within a fluid that contact the electrode pattern coupled to the skin or the wearable item.

Implementations of the method can optionally include one or more of the following features. For example, in some implementations of the method, the electrochemical sensor can be operable to detect physiological, biological, or chemical signals from the skin. In some implementations, for example, the method can further include, when attached to the skin or the wearable item, removing the coating layer from the adhesive sheet exposing a non-adhesive surface of the adhesive sheet. For example, the coating layer can include PVA. For example, the coated surface of the paper-based substrate can include a release agent material including cellulose acetate. For example, the adhesive sheet can include PDMS. In some implementations of the method, the forming can include performing screen printing, aerosol deposition, or inkjet printing the electrode pattern onto the coated surface of the paper-based substrate. For example, the electrically conductive material can include a conductive ink, e.g., including, but not limited to, gold, platinum, nickel, copper, silver, and/or silver chloride. For example, the electrically insulative material can include a nonconductive ink, e.g., including, but not limited to, PET, PS, PE, and/or PTFE. In some examples, the electrode pattern can further include an electrically semi-conductive material. For example, the electrically semi-conductive material can include a semi-conductive ink, e.g., including, but not limited to, amorphous carbon, carbon black, graphite, carbon nanotubes, and/or graphene. In some implementations of the method, for example, the electrode pattern further can include carbon fiber segments dispersed within the electrically conductive or electrically semi-conductive material.

In another aspect, an epidermal electrochemical sensor device includes a substrate formed of a flexible electrically insulative material structured to adhere to skin or a wearable item, a first electrode formed on the substrate of an electrically conductive material, a second electrode configured on the substrate of a material that is electrically conductive and separated from the first electrode by a spacing region, the first and second electrodes capable of sustaining a redox reaction to produce an electrical signal, and a first electrode interface component and second electrode interface component formed on the substrate and electrically coupled to the first electrode and the second electrode, respectively, via electrically conductive conduit, in which, when attached to the skin or the wearable item and electrically coupled via the first and second electrode interface components to one or more electrical circuits, the device is operable to detect a substance in a local environment of the skin or the wearable item.

Implementations of the device can optionally include one or more of the following features. For example, in some implementations of the device, at least one of the first electrode or the second electrode can include an enzyme catalyst and an electroactive redox mediator, the electroactive redox mediator facilitating the transfer of electrons between the electrode and the active site of the enzyme catalyst configured to sustain a redox reaction. In some implementations, for example, the device can further include an electrically conductive underlayer on the substrate and underneath each of the first electrode and the second electrode, respectively, the underlayer providing separation of the first electrode and the second electrode.

In another aspect, a method to fabricate an epidermal electrochemical sensor device includes depositing an electrically conductive ink on an electrically insulative substrate to form two or more electrodes adjacent to and separated from one another and conduit wires connecting to each of the electrodes, the depositing including printing the ink on a first stencil placed over the substrate, the first stencil including a patterned region configured in a design of the two or more electrodes and the conduit wires to allow transfer of the ink on the substrate, and the first stencil inhibiting transfer of the ink in areas outside the patterned region; curing the electrically conductive ink; depositing an electrically insulative ink on the substrate to form an insulative layer that exposes the two or more electrodes, the depositing including printing the electrically insulative ink on a second stencil placed over the substrate, the second stencil including a printing region configured in a second design to allow transfer of the ink on the substrate, the second stencil inhibiting transfer of the ink in areas outside the printing region; and curing the electrically insulative ink.

Implementations of the method can optionally include one or more of the following features. For example, in some implementations, the method can further include depositing an adhesive layer on the insulative layer that exposes the two or more electrodes, the adhesive substrate formed of a flexible electrically insulative material structured to adhere to skin or a wearable item of a user. In some implementations, for example, the substrate can include a paper substrate. For example, the paper substrate can include an upper layer and a base paper layer, the upper layer comprising a release agent coated on the base paper layer and structured to peel off to remove the paper substrate. For example, the curing can include implementing at least one of applying heat or ultraviolet radiation to the deposited ink on the substrate. In some implementations, for example, the method can further include forming an electrically semi-conductive layer over at least one of the two or more electrodes by printing an ink of an electrically semi-conductive material on a third stencil placed over the substrate, the third stencil including a printing region configured in a first design of the at least one of the two or more electrodes, the printing region allowing transfer of the ink on the paper substrate, and the third stencil inhibiting transfer of the ink in areas outside the printing region; and curing the electrically semi-conductive ink. In some implementations, for example, the method can further include dispersing carbon fibers in the electrically conductive ink. In some implementations, for example, the method can further include depositing an ion-selective membrane to the surface of at least one of the electrodes, in which the depositing includes performing at least one of: (i) drop-casting the ion-selective membrane on the anterior surface of the electrode, (ii) screen printing the ion-selective membrane on the anterior surface of the electrode, (iii) inkjet printing the ion-selective membrane on the anterior surface of the electrode, and/or (iv) aerosol deposition of the ion-selective membrane on the anterior surface of the electrode. In some implementations, for example, the method can further include depositing a catalyst to the surface of at least one of the electrodes, in which the depositing includes performing at least one of: (i) encasing the catalyst in a porous scaffold structure formed of a conducting polymer on the surface of the electrode, (ii) covalently binding the catalyst to the surface of the electrode, (iii) entrapping the catalyst in a selectively permeable membrane coupled to the surface of the electrode, and/or (iv) electrostatically binding the catalyst to the surface of the electrode. In some implementations, for example, the method can further include depositing an electroactive redox mediator to the surface of the at least one of the electrodes including the catalyst to form an electrochemical sensing layer, in which the electroactive redox mediator facilitates the transfer of electrons between the electrode and the active site of the catalyst. In some implementations, for example, the method can further include depositing multi-walled carbon nanotubes on the surface of at least one of the two or more electrodes.

The subject matter described in this patent document can be implemented in specific ways that provide one or more of the following features. For example, the disclosed technology has wide-ranging implications in the healthcare, fitness, sport and athletics performance monitoring, beauty/skin care, dermatology, environmental, and general sensing domains. For example, the disclosed technology can be easily adapted for use in the generalized healthcare, fitness, sport, remote monitoring, wireless healthcare, personalized medicine, performance monitoring, and war-fighter monitoring domains. Also, for example, the disclosed technology can involve the substitution of test strips for metabolite and electrolyte monitoring in the perspiration, and may replace conventional screen printed electrochemical test strips in other diagnostics and environmental monitoring applications.

Advances in material and device fabrication techniques can be used body-worn electronic devices that are mated directly with the skin for the measurement of physiological parameters of the individual wearer. The disclosed technology here can enable body-worn devices to provide analysis of chemical constituents residing on the surface of the skin. This analysis can provide useful insight into the overall health and physical activities of an individual and possible exposure to chemical or biological agents and certain hazardous substances. For successful implementation of direct epidermal electrochemical devices attached to the body of a user, the devices must exhibit compatible elasticity between the device substrate and the skin.

Techniques, systems, and devices are described for fabricating and implementing electrochemical biosensors and chemical sensors that can be transferred onto the skin or wearable item, e.g., by a procedure analogous to the transfer of a temporary tattoo.

The disclosed technology can include biosensors and chemical sensors that use detection methodologies including amperometry, voltammetry, potentiometry, and/or electrochemical impedance spectroscopy for epidermal monitoring of a wearer's bodily substances such as fluids or gases or the wearer's exposure to one or more substances in the surrounding environment. The disclosed biosensors and chemical sensors can include temporary transfer electrochemical biosensors and chemical sensors that can be applied for limited or long term use on the user's skin for direct physiological and security monitoring of chemical constituents. The exemplary temporary transfer electrochemical biosensors and chemical sensors can be produced in the form of aesthetic designs similar as a skin tattoo, referred to herein as epidermal temporary transfer tattoo (T3) sensors. In some implementations, the disclosed sensors can include electrode patterns forming a complete electrochemical system, as well as include the selection of the appropriate layering and ink formulation to facilitate the required electrochemical response. Exemplary sensors of the disclosed technology can be implemented in epidermal monitoring of the wearer's environment and physiological fluids residing on the surface of the epidermis, e.g., such as perspiration. For example, the exemplary sensors can be used to measure one or more physiological parameters, e.g., including but not limited to measurements of chemical or biological substances in body fluids and provide useful insight into the real-time physical conditions or overall health of the individual wearer as well as their exposure to chemical or biological agents/hazards residing in their local environment by analyzing of the detected chemical constituents residing on the surface of the skin. For example, the exemplary sensors can be used in noninvasive on-body continuous-monitoring in healthcare, fitness, remote monitoring, and other applications.

The disclosed technology includes fabrication processes to produce the exemplary temporary transfer electrochemical biosensors and chemical sensors. For example, in some implementations, the disclosed fabrication processes includes a method to produce the exemplary T3 sensors that is compatible with the non-planar features and surface irregularities that are characteristic of the human anatomy, e.g., to provide direct chemical sensing on the skin. Exemplary approaches of this method can include the adhesion of printable, high-resolution electrode patterns onto the epidermis using T3 substrates. The exemplary T3 chemosensors are compatible with the skin and can be mated with and conform to the contours of the body. In some implementations, for example, carbon fiber-reinforced tattoo inks can be employed in the exemplary T3 sensors to provide the durability required to withstand the mechanical stresses relevant to epidermal wear. In some examples of the disclosed T3 sensors, customized artistic electrode patterns can be produced that conceal their electrochemical functionality. The sensing paradigm of the exemplary T3 sensors can be suitable for a plethora of diverse body-worn chemosensing applications where true bionic integration is a core requirement for developing 'electronic skin'.

In some implementations, the disclosed electrochemical sensors and biosensors can be printed on paper, plastic, or ceramic substrates that are either inserted into or included on the surface of a wearable item, e.g., including, but not limited to, a wristwatch, armband, chest-strap, belt, or headband for direct epidermal contact and sensing.

In one aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, and attaching an adhesive sheet on a surface of the electrochemical sensor having the electrode pattern, the adhesive sheet capable of adhering to skin or a wearable item, in which the electrochemical sensor, when attached to the skin or the wearable item, is operable to detect chemical analytes within an external environment.

In another aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, attaching an adhesive sheet on a surface of the electrochemical sensor having the electrode pattern, the adhesive sheet capable of adhering to skin or a wearable item and structured to include a coating layer on an external surface of the adhesive sheet, and removing the paper-based substrate from the electrochemical sensor to expose the electrode pattern, in which the electrochemical sensor, when attached to the skin or the wearable item, is operable to detect a substance present within a fluid that contact the electrode pattern coupled to the skin or the wearable item.

For example, the disclosed technology can be used to construct a body-worn sensor device that is either directly attached to the skin or is included as part of a body-worn article, e.g., such as clothing, a wrist band, a wrist watch, a piece of footwear, or a monitoring device. Such a body-worn sensor device can include a multi-layer material structure that has an electrochemical sensing material layer interacting with a substance to be detected, an electrode layer formed on and in electrical contact with the electrochemical sensing material layer with a printed electrode pattern to receive one or more applied electrical signals and to output one or more electrical output signals from the electrochemical sensing material layer indicating a reaction with the substance to be detected, and a base layer to provide the support to the electrochemical sensing material layer and the electrode layer. A sensor circuit may be integrated onto the base layer in some sensor designs, or may be located outside the base layer, but is electrically coupled to the electrode layer. The multi-layer material structure may be a flexible structure for attaching to skin or a body-worn object. For skin-attached applications where such a sensor is an epidermal electrochemical sensor device, the multi-layer material structure may include a removable substrate layer such as a paper substrate and a releasing agent layer over the base layer so that device can be attached to skin after removing the removable layer. Such an epidermal electrochemical sensor device can use cellulose acetate, for example, over the removable paper substrate, and an insulator layer as the base layer which can be, e.g., a silicone material such as PDMS to provide an electrically insulating component of the overall electrode pattern of the sensor device.

Examples of sensor structures, materials and fabrication of the above and other sensor devices are provided below to illustrate various aspects of the disclosed technology.

Figure 31A:
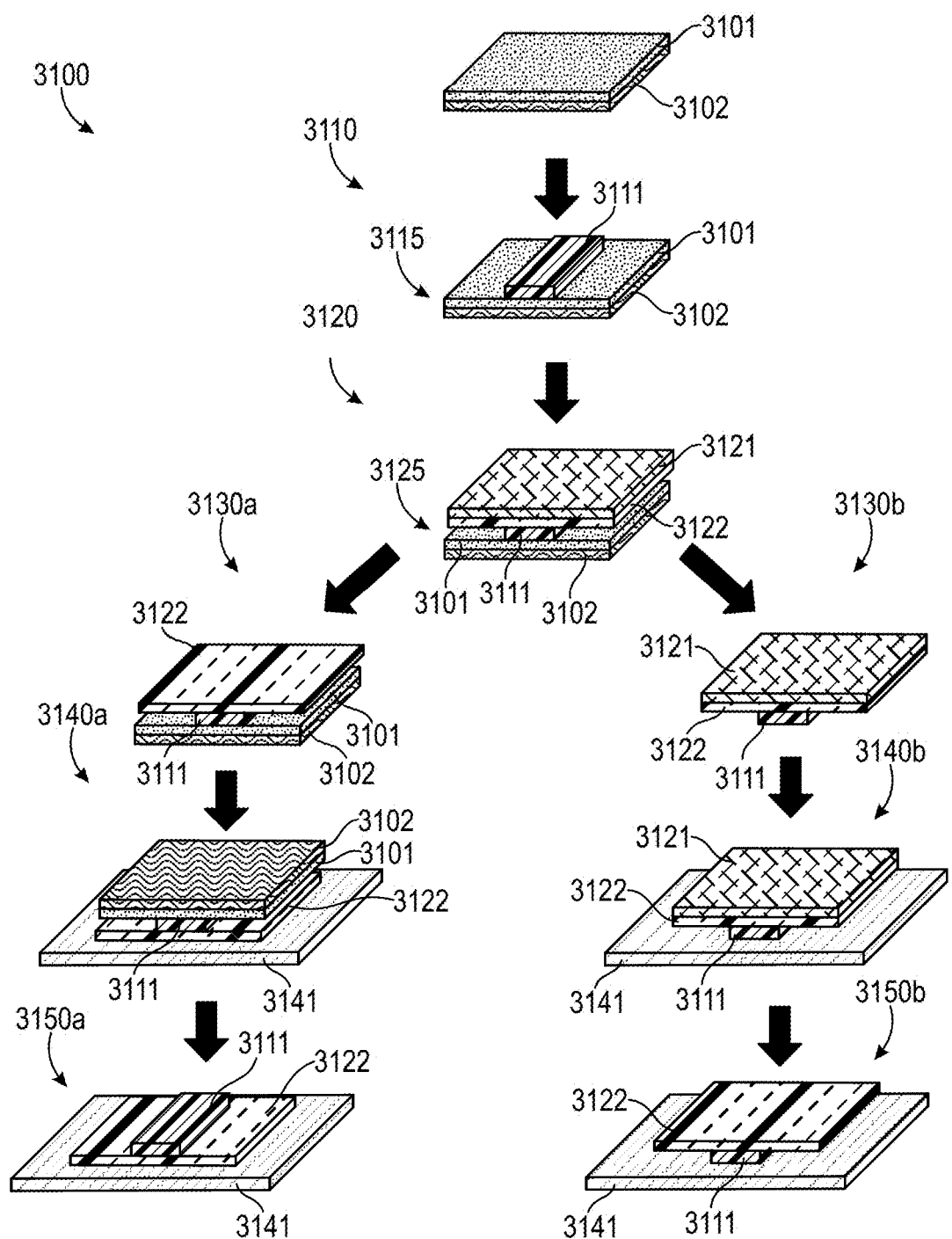
FIG. 31A shows a process diagram illustrating an exemplary fabrication method to produce epidermal electrochemical sensors of the disclosed technology, e.g., such as the exemplary T3 electrochemical sensors.

FIG. 31A shows a process diagram illustrating an exemplary fabrication method 3100 to produce epidermal electrochemical sensors of the disclosed technology, e.g., such as the exemplary T3 electrochemical sensors. The method 3100 includes a process 3110 to form electrode structures 3111 on a release agent 3101 coated on a paper-based substrate 3102 to form an electrochemical sensor component 3115. For example, the electrode structures 3111 can be patterned on the release agent 3101-coated paper substrate 3102, in which the electrode pattern includes an electrically conductive material and an electrically insulative material, and in some examples an electrically semi-conductive material, configured in a particular design layout. In some examples, the process 3110 can include screen printing the electrically conductive material (e.g., electrically conductive ink) and the electrically insulative material (e.g., electrically insulative ink), and in some examples an electrically semi-conducting ink, in the patterned design to form the electrode structures 3111.

The method 3100 includes a process 3120 to apply an adhesive sheet 3122 with a protective coating 3121 to the electrochemical sensor component 3115 to form an electrochemical sensor device 3125 capable of attaching to skin (or a wearable item) for one of sensing analytes in the external environment of the skin or fluids present on the skin.

The exemplary inks employed can include a wide variety of materials (e.g., such as graphite, gold, platinum, nickel, silver, silver chloride, polyethylene terephthalate (PET), polytetrafluoroethylene (PTFE), etc.), and their viscosity can be modified (e.g., using either binders or solvents) as needed to yield optimal results. For example, the ink can be prepared with various chemical modifications in order to impart selectivity, increase sensitivity, reduce response time, and/or further extend the stability of the amperometric, voltammetric, or potentiometric response of the electrochemical sensor device. This can include the incorporation of chemical moieties into the ink suspension (e.g., catalysts, biocatalysts, enzymes, proteins, nanoparticles, reagents, mediators, binding agents, and/or cofactors), as well as the patterning of perm-selective or ion-selective coatings/membranes to the surface of the exemplary sensor. For example, the electrically conductive ink can include, but is not limited to, gold, platinum, nickel, silver, and silver chloride inks. For example, the electrically insulative ink can include, but is not limited to, PET and PTFE inks. In some examples, the electrode structures 3111 can also include electrically semi-conductive materials including semi-conductive ink, e.g., including, but not limited to, amorphous carbon, carbon black, or graphite.

In some implementations of the method 3100, as shown in FIG. 31A, the fabricated electrochemical sensor device 3125 is prepared for epidermal monitoring of a wearer's surrounding environment. For example, the electrochemical sensor device 3125 could be used to detect volatile organic compounds, explosive remnants, and pollutants present in the air surrounding the device 3125 on the user's skin. In such cases, the method 3100 can further include a process 3130*a* to remove the protective coating 3121 from the adhesive sheet 3122 of the electrochemical sensor device 3125. Subsequently, the method 3100 then includes implementing a process 3140*a* to flip the electrochemical sensor device 3125 to be applied to skin 3141, in which the adhesive sheet 3122 is attached to the skin 3141 such that the paper based substrate 3102 is positioned away from the skin 3141. The method 3100 can then include implementing a process 3150*a* to remove the paper based substrate 3102, thereby exposing the adhered electrode structures 3111 (e.g., electrode sensor pattern) to the wearer's external environment for remote sensing. For example, the process 3150*a* can include applying water to the releasing agent 3101 to allow smooth release of the paper based substrate 3102 from the electrode structures 3111.

In some implementations of the method 3100, as shown in FIG. 31A, the fabricated electrochemical sensor device 3125 is prepared for epidermal physiological monitoring, e.g., of fluids containing biochemical analytes present on the skin. In such cases, the method 3100 can further include a process 3130b to remove the paper based substrate 3102 from the electrochemical sensor device 3125. For example, the process 3130b can include applying water to the releasing agent 3101 to allow smooth release of the paper based substrate 3102 from the electrode structures 3111. Subsequently, the method 3100 then includes implementing a process 3140b to apply the electrochemical sensor device 3125 to the skin 3141 via the attachment of the adhesive sheet 3122 to the skin 3141 such that the external surface of the electrode structures 3111 are in contact with the surface of the skin 3141. In some implementations, the method 3100 can then include implementing a process 3150b to remove the protective coating 3121 from the adhesive sheet 3122 of the electrochemical sensor device 3125.

Figure 31B:
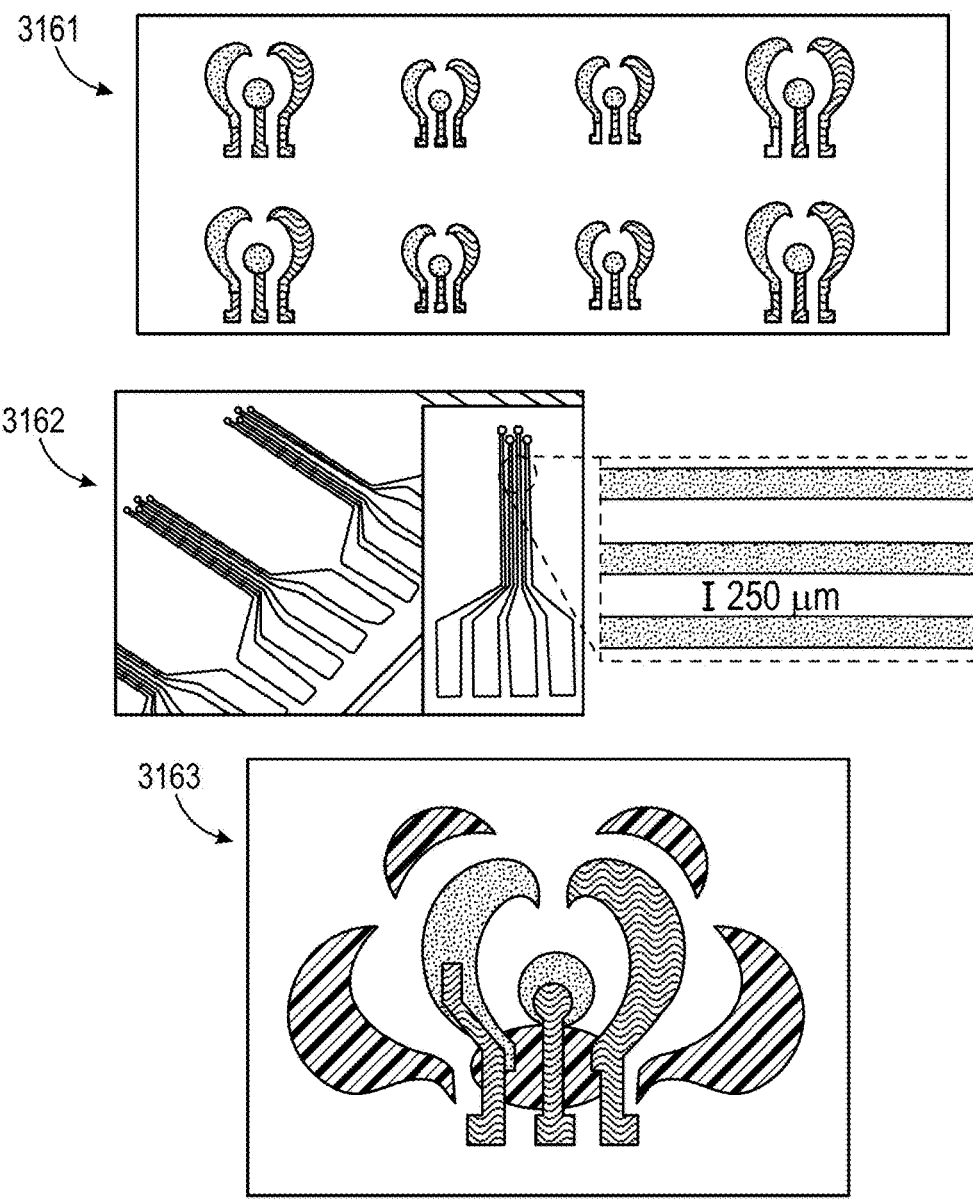
FIG. 31B shows images of exemplary T3 electrochemical sensors showing several exemplary printed designs.

FIG. 31B shows images 3161, 3162, and 3163 of exemplary T3 electrochemical sensors showing several exemplary printed designs. The image 3161 illustrates a high-quality array of three-electrode artistic electrochemical sensors possessing two varying sizes. The image 3162 illustrates an array of microelectrodes that can be used for small-sample bioanalysis, for example. The corresponding inset in the image 3162 exemplifies those well-defined patterns possessing micrometer-scale resolution can be produced with the disclosed fabrication method 3100. The image 3163 shows exemplary artistically patterned T3 electrochemical sensors that can be employed for environmental sensing of the wearer's local vicinity. The exemplary T3 electrochemical sensor depicted in the image 3163 indicates that the implementation of finely-segmented and well-dispersed carbon fibers do not compromise the quality of the thick-film fabrication process. For example, the exemplary T3 electrochemical sensors can be fabricated using the described thick film process without special arrangements to accommodate the T3 paper in the printing process.

Figure 31C:
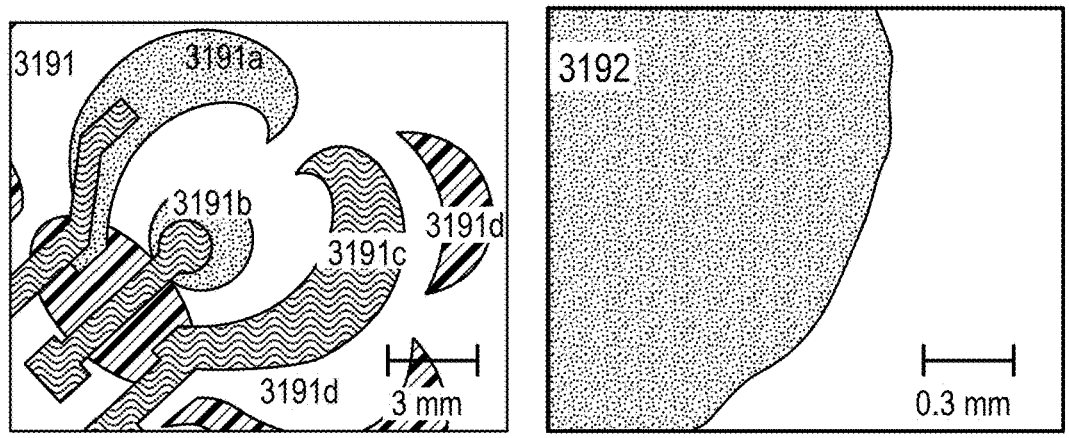
FIG. 31C shows an image of an exemplary three-electrode T3 biosensor applied to porcine skin for physiological monitoring.

FIG. 31C shows an image 3191 of an exemplary three-electrode T3 biosensor applied to porcine skin for physiological monitoring. The image 3191 displays exemplary constituents of the sensor that include an Ag/AgCl reference electrode (3191a), a carbon working electrode (3191b), a carbon counter electrode (3191c), and an insulator structure (3191d) that circumscribes the electrodes. FIG. 31C also shows an image 3192 showing a magnified view of the carbon electrodes 3191b displaying well-defined borders and rough morphology.

In one exemplary implementation of the method 3100, for example, a sheet of paper can be coated with a thick-film of cellulose acetate to impart rigidity for subsequent processing. After the cellulose acetate layer has dried and solidified, a thick-film of silicone such as polydimethylsiloxane (PDMS) can be deposited and the paper-cellulose acetate-PDMS contingent can be cured at a specific temperature to solidify the PDMS layer. Thereafter, a thick-film of warm polyvinyl alcohol (PVA) can be deposited on the surface and allowed to dry. Subsequently, the ink can be cured, e.g., at a suitable temperature. The exemplary process is then repeated, as needed, for the number of layers required. Each layer can either employ an identical ink formulation as the previous layer or a different one entirely. For example, the described fabrication technique includes integration of printing and tattoo-transfer protocols and thick-film fabrication processes to produce such advanced electrochemical sensors capable of epidermal detection of physiologically-relevant compounds as well as agents of environmental/security relevance. The exemplary technique can produce body-worn electrochemical sensors that are compliant with the skin for the realization of non-invasive extended chemical monitoring. Nearly any artistic tattoo design can be formed in the fabrication of the electrochemical sensors, e.g., allowing the sensors to be concealed in rather inconspicuous tattoo artwork, without compromising the favorable resolution and performance inherent to printable sensors.

Figure 31D:
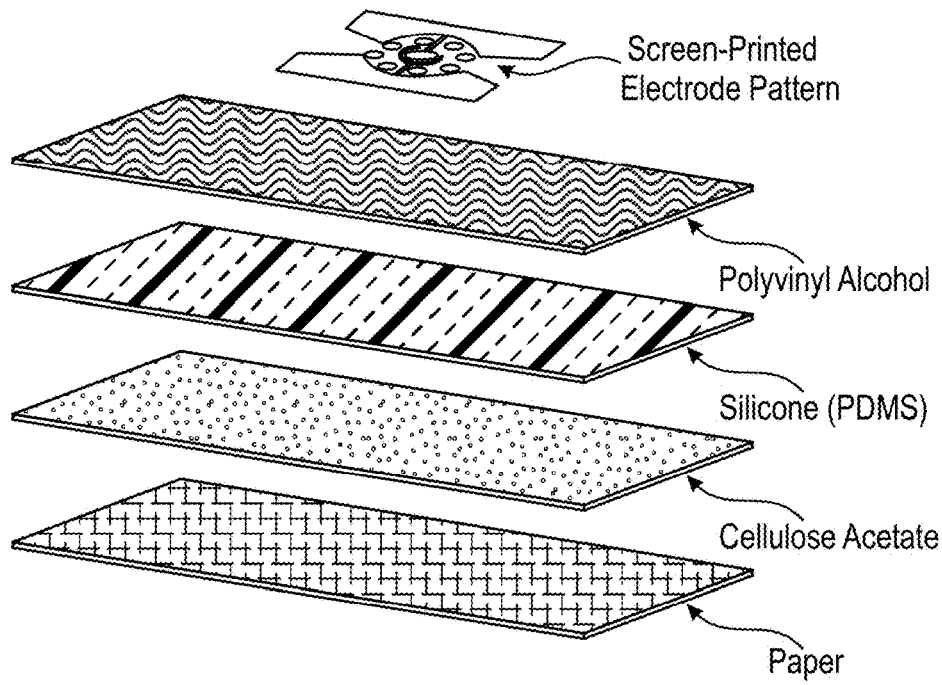
FIG. 31D shows a schematic illustration of exemplary material layers of an exemplary epidermal electrochemical sensor device.

FIG. 31D shows a schematic illustration of exemplary material layers of an exemplary epidermal electrochemical sensor device. In this example, the exemplary device includes a paper substrate and a releasing agent layer, e.g., formed of cellulose acetate, over the paper substrate. The exemplary device also includes an insulator layer, e.g., formed of a silicone material, such as PDMS, that is formed on the releasing agent layer to provide an electrically insulating component of the overall electrode pattern of the sensor device. In this example, an outer coating layer, e.g., polyvinyl alcohol (PVA), is applied on the insulator layer. The exemplary device includes an electrode pattern, e.g., which can be screen printed on the coating layer, including electrically conductive and/or electrically semi-conductive inks to form the electrodes of the sensing device in any desired pattern.

In some implementations of the method 3100, for example, carbon fiber (CF) segments can be dispersed within the tattoo ink to augment the electrode's tensile strength and provide the electrode with an interlinked conductive backbone while enhancing the electrochemical behavior, hence reflecting the inherent properties of the fiber constituents. Inclusion of such CFs in the ink materials can counteract cracking and alleviate mechanical degradation associated with routine skin-based wear. By harnessing CF-dispersed inks for mechanical reinforcement, the fabricated electrochemical sensors exhibit substantial resiliency against extreme deformation, e.g., such as repeated pinching, bending, flexing, and twisting. The resulting wearable epidermal sensing devices of the disclosed technology thus couple favorable substrate-skin elasticity along with highly attractive electrochemical performance.

Figure 31E:
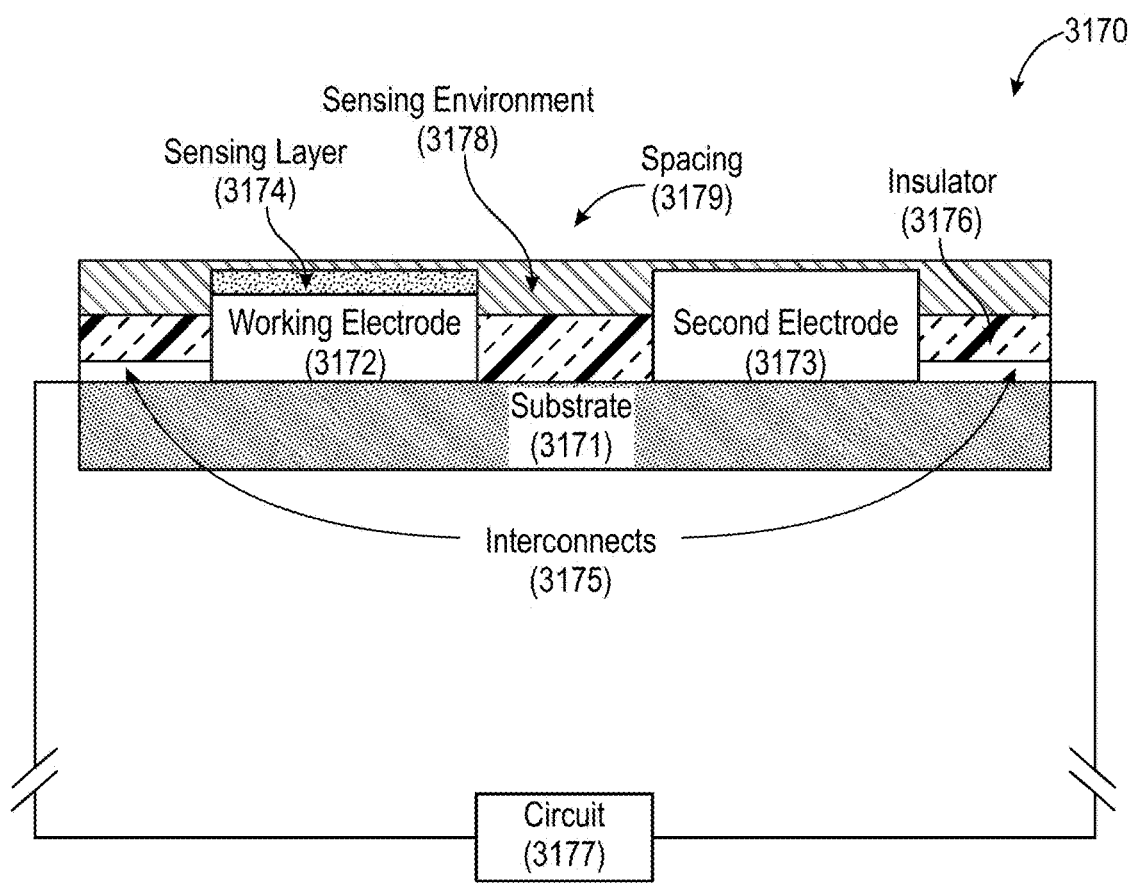
FIG. 31E shows a block diagram of an exemplary embodiment of an epidermal electrochemical sensor device capable of being worn on skin or a wearable item.

FIG. 31E shows a block diagram of an exemplary embodiment of an epidermal electrochemical sensor device 3170 capable of being worn on skin or a wearable item. The electrochemical sensor device 3170 includes a substrate 3171 of an electrically insulative material, which can be configured as a flexible substrate. The electrochemical sensor device 3170 includes a working electrode 3172 and a second electrode 3173 on the substrate 3171, in which the working electrode 3172 and the second electrode 3173 are separated from one another by a spacing region 3179. The electrochemical sensor device 3170 can include an insulator layer or structure 3176, e.g., which can provide further support for the device 3170, as well as include various artistic designs like that of a tattoo.

For example, the electrode configuration of the disclosed epidermal electrochemical sensor devices can be designed based on the type of target analyte to be sensed and the type of detection methodology, e.g., amperometry, voltammetry, potentiometry, conductometry, and/or electrochemical impedance spectroscopy, to be employed. In some examples, the epidermal electrochemical sensor device 3170 can be configured to detect charged analytes, e.g., using potentiometry or conductometry. In some examples, the epidermal electrochemical sensor device 3170 can be configured to detect self-oxidizing analytes on a bare working electrode 3172, in which the device includes a third electrode (not shown in FIG. 31E) positioned between the working electrode 3172 and second electrode 3173; and the second electrode 3173 and the third electrode can serve as a counter electrode and a reference electrode, respectively. In some embodiments, for example, the electrochemical sensor device 3170 includes an array of electrodes, e.g., such as an array of working electrodes, counter electrodes, and/or reference electrodes.

In other examples, as shown in the diagram of FIG. 31E, the working electrode 3172 includes an electrochemical sensing layer 3174 to sustain a redox reaction to produce a detectable electrical signal that can be detected using, for example, amperometry and/or voltammetry. The electrochemical sensing layer 3172 provides a reaction agent (e.g., the catalyst) that can undergo a redox reaction with a target analyte (e.g., such as a particular molecule or substance) that produces charge carriers sensed by the working electrode 3172. The electrochemical sensing layer 3172 can be structured to include a catalyst and an electroactive redox mediator. In some examples, the target analyte can be oxidized by the catalyst, releasing electrons in the process, which gives rise to an electrical current that can be measured between the working electrode 3172 and second electrode 3173. For example, the electroactive redox mediator can facilitate the transfer of electrons between the working electrode 3172 and the active site of the catalyst. The electrochemical sensing layer 3174 can be configured to the working electrode 3172 in at least one of the following configurations: (i) the catalyst dispersed within the material of the working electrode 3172; (ii) the catalyst coated as a layer on the surface of the working electrode 3172; (iii) the catalyst entrapped by an electropolymerized conducting polymer formed on the surface of the working electrode 3172; (iv) the catalyst entrapped by a selectively permeable scaffold structure, e.g., such as Nafion or chitosan, formed on the surface of the working electrode 3172; (v) the catalyst covalently bonded to the surface of the working electrode 3172; or (vi) the catalyst electrostatically anchored to the surface of the working electrode 3172. In exemplary implementations including the electroactive redox mediator, for example, the electroactive redox mediator can be configured in the electrochemical sensing layer 3174 along with the catalyst by the same exemplary configuration.

As shown in the diagram of FIG. 31E, the electrochemical sensor device 3170 includes an electrical sensor circuit 3177 electrically coupled to the electrodes via electrical interconnects 3175. For example, the sensor circuit 3177 can be configured to apply excitation waveforms and/or transduce the electrical signals generated by the electrochemical electrodes of the electrochemical sensor device 3170 upon excitation. In some examples, the sensor circuit 3177 can include a display or other interface to display the results to the wearer or other user, e.g., such as a coach, trainer, or physician. The sensor circuit 3177 can be structured to include, but not limited to, a potentiostat (e.g., to realize amperometric and voltammetric measurements) or a galvanostat (e.g., to realize potentiometric measurements). In some embodiments, for example, the electrochemical sensor device 3170 can include electrically conductive contact pads coupled to the interconnects 3175 to provide a conductive surface to electrically interface an external circuit (e.g., such as the sensor circuit 3177) to the electrodes of the electrochemical sensor device 3170.

The electrochemical sensor device 3170 can be applied to skin or a wearable item in such a way that a sensing environment 3178 can include, for example, fluids in contact with the user's skin or clothing worn by the user, or the external environment in which the user is in, e.g., including air or water. The sensing environment 3178 contains the target analyte to come into contact with the electrodes. In some examples, if the sensing environment 3178 includes a fluid, e.g., such as a body fluid like perspiration.

Exemplary implementations of the disclosed electrochemical sensor technology were performed, which included the described materials, procedures, and data.

The exemplary implementations described herein included the use of the following materials and equipment. For example, ascorbic acid (AA), uric acid (UA), 2,4-dinitrotoluene (DNT), potassium ferricyanide ($K_3Fe(CN)_6$), 2,4,6-trinitrotoluene (TNT), potassium phosphate monobasic ($KH_2PO_4$), and potassium phosphate dibasic ($K_2HPO_4$) were used without further purification or modification. Chopped carbon fibers (CFs), e.g., including having 8 μm diameter, 6.4 mm length, 93% purity, were processed to reduce the CF length to approximately 0.5 mm. The exemplary reagents were prepared in a 0.1 M phosphate buffer solution (PBS, pH 7.4). Ultrapure water (18.2 MΩ·cm) was used in the exemplary implementations, and the exemplary implementations described were performed at room temperature. For example, Ag/AgCl conductive ink carbon graphite ink and insulator ink were utilized. Laser temporary tattoo paper kits were obtained from HPS Papilio (Rhome, Tex.). For comparison, custom-fabricated carbon screen-printed electrodes (on alumina, 2 mm working electrode diameter) were employed. Cadaveric porcine skin samples were immediately refrigerated upon arrival until temporary transfer tattoos were applied. A CH Instruments (Austin, Tex.) model 660D electrochemical analyzer was employed, for example, for the voltammetric, amperometric, potentiometric, and impedometric experiments. A Keithley (Cleveland, Ohio) model 6514 system electrometer was used to characterize trace resistance, for example. An Olympus optical microscope with an integrated CCD camera was utilized, for example, to investigate the surface morphology of the printed epidermal sensors in greater detail.

Exemplary sensor patterns were designed in AutoCAD (Autodesk, San Rafael, Calif.) and outsourced for fabrication on 75 μm-thick stainless steel stencils. For example, a separate stencil pattern was created for each layer (e.g., Ag/AgCl, carbon, insulator). A semi-automatic screen printer was employed for the fabrication efforts. For example, in order to conduct electrochemical experiments, a tattoo pattern containing a circular working electrode was designed and possessed a 3 mm radius. For example, in order to increase the tensile strength of the printed electrodes and mitigate the cracking observed during typical wear, 100 mg of chopped CFs were dispersed in 30 mL of ink and homogenized thoroughly.

Exemplary fabrication methods of the disclosed technology to manufacture electrochemical biosensors and chemical sensors were employed to produce the exemplary T3 sensors for transfer onto skin (or other wearable items) in a procedure analogous to that employed to transfer of a temporary tattoo. Exemplary techniques described involved the layering of certain materials on a substrate (e.g., paper substrate), on top of which a screen-, aerosol-, or inkjet-printed sensor pattern was defined. The substrate, e.g., containing the thick-film sensor patterns, was reversed and applied to the skin using a damp water-infused cloth or sponge. The backing substrate of the exemplary fabricated sensor device was then peeled away, leaving only the functional printed sensor pattern and a water-soluble synthetic polymer binder.

For example, screen printing can be employed for the formation of thick-film electrodes intended to be used in a wide variety of electrochemical applications. For example, this technique employs an automated system that guides a squeegee across a patterned stencil to extrude a specially-formulated ink in order to transfer an identical electrode pattern onto the substrate. This technique offers an attractive combination of moderate throughput and low cost.

Exemplary implementations were performed to investigate the printing quality of the exemplary ink materials on the T3 paper substrate. The exemplary T3 sensors fabricated using the disclosed methods were applied to the epidermis of various human subjects, and exemplary implementations were performed to evaluate the exemplary T3 sensors.

FIG. 32A shows images 3201-3204 for transferring an exemplary epidermal electrochemical sensor device, e.g., such as the exemplary device shown in the images 3163 and 3190 of FIGS. 31B and 31C, on a user's skin. The image 3201 shows the exemplary electrochemical sensor device attached to the paper substrate, in which the protective film removed and the adhesive layer exposed. The image 3202 shows the exemplary electrochemical sensor device with the attached paper substrate applied to the user's skin such that the electrode patterned region is in direct contact with the epidermis. For example, the T3 paper is flipped (e.g., electrode patterned side down) and depressed on the surface of the skin. The image 3203 shows the wetting of the releasing agent layer of the exemplary electrochemical sensor device attached to the user's skin. For example, the paper substrate is gently dabbed with water until it becomes saturated. The image 3204 shows the removal of the paper substrate, e.g., leaving the printed electrode contingent in direct contact with the epidermis. For example, the paper substrate is removed from the epidermis by gradually sliding it along and off the skin surface.

FIG. 32B shows images 3205, 3206, and 3207 of several representative design permutations transferred onto the epidermis. The image 3205 shows an exemplary three-electrode electrochemical sensing contingent, and the image 3206 shows the transfer of an exemplary high-resolution sensor array onto the skin. For example, the inset image in the image 3206 shows well-defined 150 μm-wide electrode features that are easily transferred onto the epidermis, e.g., underscoring the fidelity at which the patterns are printed and transferred. The image 3207 displays a pair of exemplary artistically-inspired and fully functional three-electrode sensors possessing two different sizes. The disclosed T3 electrochemical sensors can be configured in nearly any electrode design and can be implemented without compromising the sensor functionality, e.g., such as in cases when an artistic impact is desired.

FIG. 32C shows images 3208, 3209, and 3210 that validate the structural resiliency of the exemplary T3 sensors to extreme mechanical deformations, e.g., in which various strain permutations were applied to the sensors. For example, the images 3208 and 3209 demonstrate deformation of an exemplary tattoo sensor when pinched with the forefingers or upon stretching the skin, respectively. Likewise, for example, the image 3210 illustrates a twisting operation on the exemplary sensor. As shown in the images of FIG. 32C, the application of these strain permutations exhibited minimal effect on the appearance and quality of the T3 sensor. Additional exemplary implementations on the impact of such strain permutations upon the electrochemical performance of these printable epidermal sensors were performed.

Exemplary implementations were performed for electrochemical characterization of the T3 sensing methodology aimed at comparing the disclosed sensing paradigm with conventional screen printed electrodes (SPEs) on solid alumina substrates. For example, voltammetric signatures were contrasted between the two systems, and a GORE-TEX fabric was used for the tattoo investigations in order to emulate the viscoelastic properties of the epidermis.

Figures 33A, 33B, 33C:
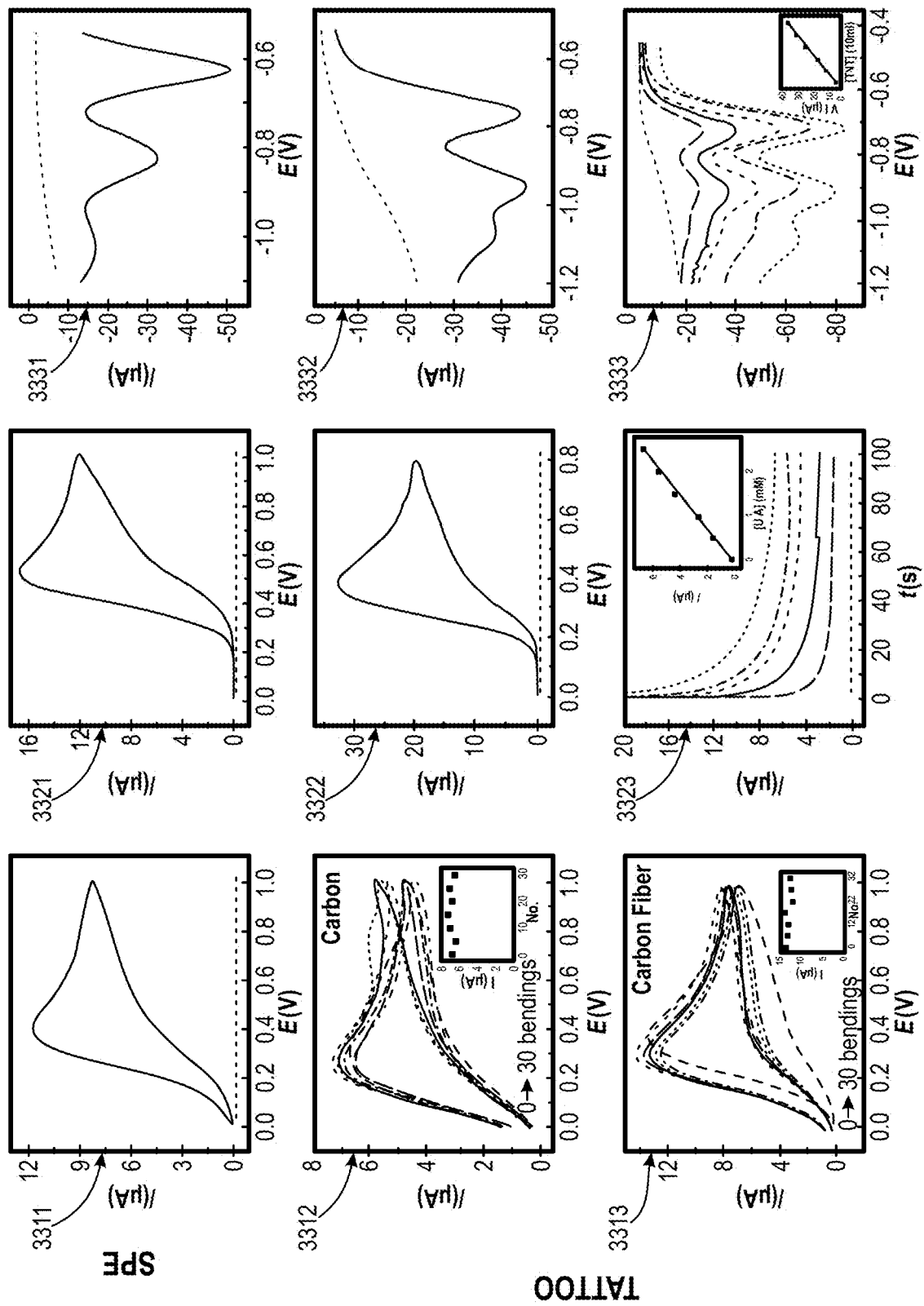
FIG. 33A shows cyclic voltammogram data plots that were obtained for 2.5 mM ascorbic acid (AA) at an exemplary SPE, at an exemplary T3 sensor on GORE-TEX, and at an exemplary CF-reinforced T3 sensor on GORE-TEX.
FIG. 33B shows cyclic voltammetric response plots that were obtained for the detection of 2.5 mM uric acid (UA) at an exemplary SPE an exemplary CF-reinforced T3 sensor on porcine skin.
FIG. 33C shows SWV plots that were obtained for the electrochemical detection of 225 μg/mL TNT at an exemplary SPE, an exemplary CF-reinforced T3 sensor on porcine skin.

FIG. 33A shows cyclic voltammogram data plots 3311, 3312, and 3313 that were obtained for 2.5 mM ascorbic acid (AA) at an exemplary SPE (shown in the plot 3311), at an exemplary T3 sensor on GORE-TEX (shown in the plot 3312), and at an exemplary CF-reinforced T3 sensor on GORE-TEX (shown in the plot 3313). The exemplary tattoo-based sensor embodied favorable electrochemical properties when compared with the conventional SPE. As an additional benefit, for example, the incorporation of CFs into the ink matrix enhanced the electrochemical response of the tattoo sensor device substantially, leading to better-defined oxidation peaks that emulated the response obtained at the conventional electrode contingent. Moreover, for example, both the unreinforced T3 electrochemical sensors and the CF-reinforced T3 electrochemical sensor exhibited resiliency against thirty repetitive 180° bending iterations, hence maintaining their favorable voltammetric behavior under extreme mechanical strain. As can be inferred from a comparison of the inset plots in the plots 3312 and 3313, both the unreinforced and CF-reinforced T3 sensors displayed only small (e.g., less than 10%) deviations from the original current response following repetitive bending operations.

FIG. 33B shows cyclic voltammetric response plots 3321 and 3322 that were obtained for the detection of 2.5 mM uric acid (UA) at an exemplary SPE (shown in the plot 3321) an exemplary CF-reinforced T3 sensor on porcine skin (shown in the plot 3322). As represented from these exemplary data, the CF-reinforced tattoo electrode exhibited improved electrochemical performance to that of the SPE. For example, the peak potential and peak current assumed more desirable values when compared with the conventional SPE. FIG. 33B also shows an amperometric response plot 3323 generated at the exemplary CF-reinforced T3 electrochemical sensor for increasing UA concentration. For example, a highly linear calibration was recorded at the skin-based electrode, corroborating its use not only as a viable alternative to SPEs but also as an advanced epidermal electrochemical sensor.

The disclosed tattoo sensing paradigm can also be extended to the identification of environmental substances including hazards and pollutants present in the vicinity of the wearer, e.g., for environmental and security monitoring. For example, the disclosed technology was extended to the detection of the common explosive 2,4,6-trinitrotoluene (TNT), in connection with square wave voltammetry (SWV). FIG. 33C shows SWV plots 3331 and 3332 that were obtained for the electrochemical detection of 225 μg/mL TNT at an exemplary SPE (shown in the plot 3331) an exemplary CF-reinforced T3 sensor on porcine skin (shown in the plot 3332). Both the plots 3331 and 3332 exemplify the well-defined TNT response, which substantiates that the exemplary T3 electrochemical sensors (even when mated with the skin) contend with the performance offered by well-established SPE sensors fabricated on solid supports. FIG. 33C also shows an SWV response plot 3333 of the exemplary epidermal sensor for increasing TNT concentrations, which is shown to be well-defined and highly linear (as shown in the inset plot).

Exemplary implementations were performed to investigate the fundamental electrical properties of an exemplary T3 sensor, e.g., which can be considered imperative in order to ascertain its utility as a viable electrochemical device for integration with epidermal electronics. For example, a resistive and complex-valued impedance profile was evaluated under the application of mechanical deformation.

Figure 34A:
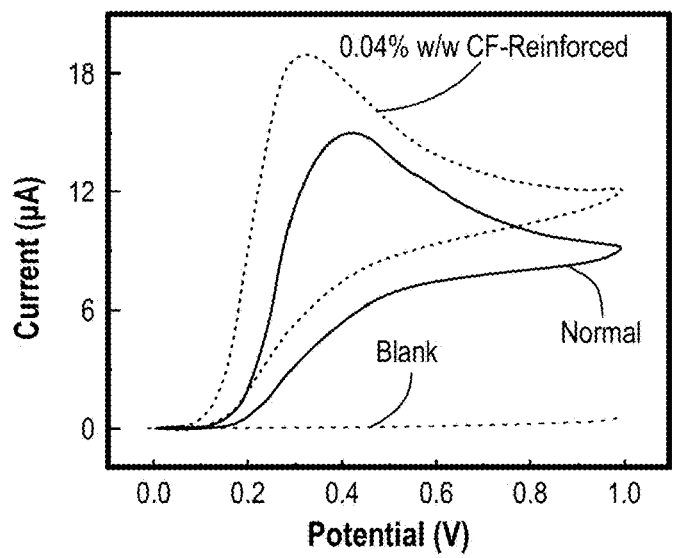
FIG. 34A shows a cyclic voltammogram plot illustrating the enhanced response generated by the dispersion of CF segments into the ink matrix, e.g., in which the scan rate was 10 mV/s.
Figure 34B:
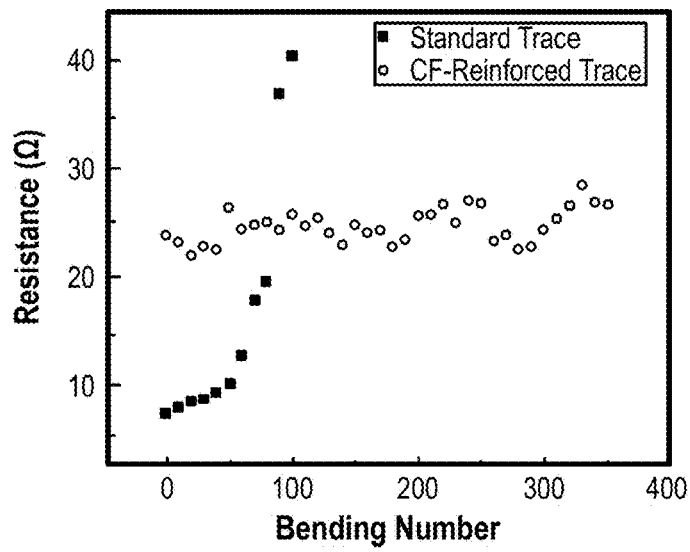
FIG. 34B shows a resistive profile plot of a normal (black squares) and carbon fiber-reinforced (red dots) 1 cm Ag/AgCl tattoo trace on porcine skin.
Figure 34C:
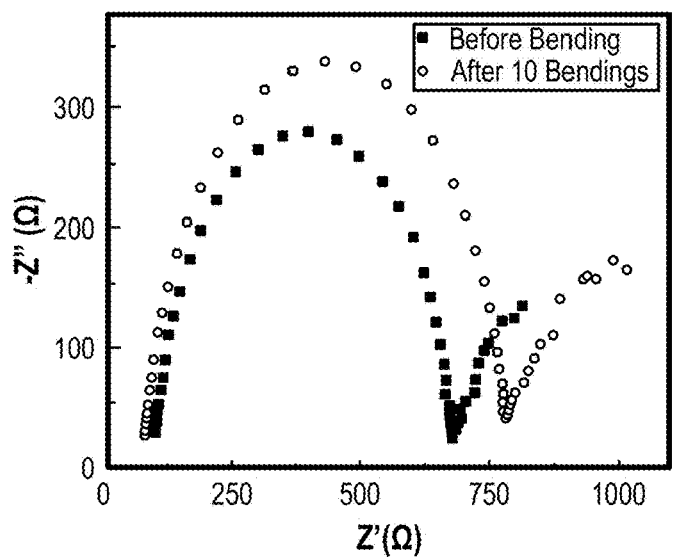
FIG. 34C shows a plot of Nyquist complex-valued impedance curves generated by an exemplary T3 sensor before bending (black squares) and after 10 bending operations (red dots) on porcine skin, e.g., in which potassium ferricyanide ($K_3Fe(CN)_6$) was employed as the redox probe.

FIG. 34A shows a cyclic voltammogram plot illustrating the enhanced response generated by the dispersion of CF segments into the ink matrix, e.g., in which the scan rate was 10 mV/s. FIG. 34B shows a resistive profile plot of a normal (black squares) and carbon fiber-reinforced (red dots) 1 cm Ag/AgCl tattoo trace on porcine skin. FIG. 34C shows a plot of Nyquist complex-valued impedance curves generated by an exemplary T3 sensor before bending (black squares) and after 10 bending operations (red dots) on porcine skin, e.g., in which potassium ferricyanide ($K_3Fe(CN)_6$) was employed as the redox probe. For example, the impedance spectrogram parameters included a frequency of 0.1 Hz-10 kHz, an applied potential of 0.4 V vs. Ag/AgCl, and an amplitude of 10 $mV_{pp}$.

The implementations included resistance measurements that were recorded via the application of multimeter probes at opposite extremities of a 1 cm Ag/AgCl trace on an exemplary GORE-TEX-based T3 sensor (including both the CF-modified and unmodified embodiments). As previously shown in the insets of the plots 3312 and 3313, respectively in FIG. 33A, both the exemplary unreinforced and CF-reinforced tattoo sensors exhibited repeatable electrochemical performance following several dozen bending iterations. However, in this example, the unreinforced/standard electrode trace increased in its intrinsic resistance until catastrophic failure occurred at the $100^{th}$ bending iteration, e.g., represented by a completely severed trace, R=∞, as shown in FIG. 34B. Conversely, for example, in this exemplary implementation, the exemplary CF-reinforced electrode, although possessing slightly elevated intrinsic resistance at the commencement of the implementation (e.g., ~25Ω), maintained its conductivity even following over 350 bending repetitions, and hence substantiating its ability to withstand highly-repetitive mechanical deformation and underscores its suitability for epidermal integration.

The exemplary implementations included an electrochemical impedance spectroscopy performed at the exemplary CF-reinforced T3 sensor (on GORE-TEX), e.g., to ascertain the frequency at which the complex impedance indicates a transition from a reaction that is controlled via mass-transfer to one that is governed by kinetics. As exemplified in FIG. 34C, this transition occurred at approximately 4 Hz and 8 Hz for this exemplary CF-reinforced T3 sensor prior to and immediately following ten bending iterations, respectively. As shown in FIG. 34C, for example, the change in the impedance profile following stretching was shown to be minimal In accordance with the Randles-Ershler formalism, a solution resistance, $R_Ω$, of ~100Ω, charge transfer resistance, $R_{ct}$, of ~580Ω, and a double-layer capacitance, $C_{dl}$, of 3.6 µF, can be interpolated from the plot.

The increased tolerance of the CF-dispersed electrodes against severe mechanical deformation should not compromise the electroanalytical performance offered by the disclosed devices. This is shown in FIG. 34A. For example, an exemplary unreinforced T3 biosensor was evaluated alongside an exemplary CF-reinforced T3 biosensor possessing a 0.04% (w/w) CF loading level in an exemplary implementation to provide the cyclic voltammetric response. As shown FIG. 34A, the electrochemical figures of merit differed slightly between the unreinforced (e.g., $E_p$=0.42 V, $i_p$=15.0 µA, and $k_s$=8.8E$^{-4}$ cm/s) and the 0.04% CF-reinforced sensor (e.g., $E_p$=0.32 V, $i_p$=19.0 µA, and $k_s$=1.1E$^{-3}$ cm/s). In this exemplary implementation, the reinforced exemplary T3 sensor exhibited more favorable electrochemical properties, as shown from the enhanced voltammetric behavior in FIG. 34A.

Exemplary implementations were performed for exemplary printed T3 sensors for environmental/security monitoring applications. For example, in order to demonstrate the ability to operate in vapor-phase environments, an exemplary CF-modified T3 sensor was applied towards the detection of increasing levels of 2,4-dinitrotoluene (DNT) vapors. As such, the exemplary tattoo-based sensor was applied to a porcine skin sample, which was subsequently inserted in a sealed 15 mL container along with 100 mg of DNT salt. The system was allowed to equilibrate for 30 min, after which a calibration (with respect to time) was performed. The exemplary calibration data showed a high degree of linearity along with rapid response time. Repeated measurements were conducted, with the exemplary resultant data demonstrating precise repeatability. For example, maximum 6.9% deviation in the current level at the reduction peak (−1.05 V vs. Ag/AgCl) was observed across six independent measurements. For example, it is noted that vapor-phase detection is traditionally not feasible using bare SPEs due to the lack of a supporting electrolytic medium. However, the exemplary T3 electrochemical sensors exhibit a noteworthy structural difference when compared with conventional SPEs. For example, a perspiration-saturated adhesive polymer layer can be employed as the structural backbone, which may behave analogously to common hydrogel layers. Thus, the exemplary implementations demonstrated that the exemplary tattoo-based device is well suited to serve as a vapor-phase environmental sensor.

Figure 35A:
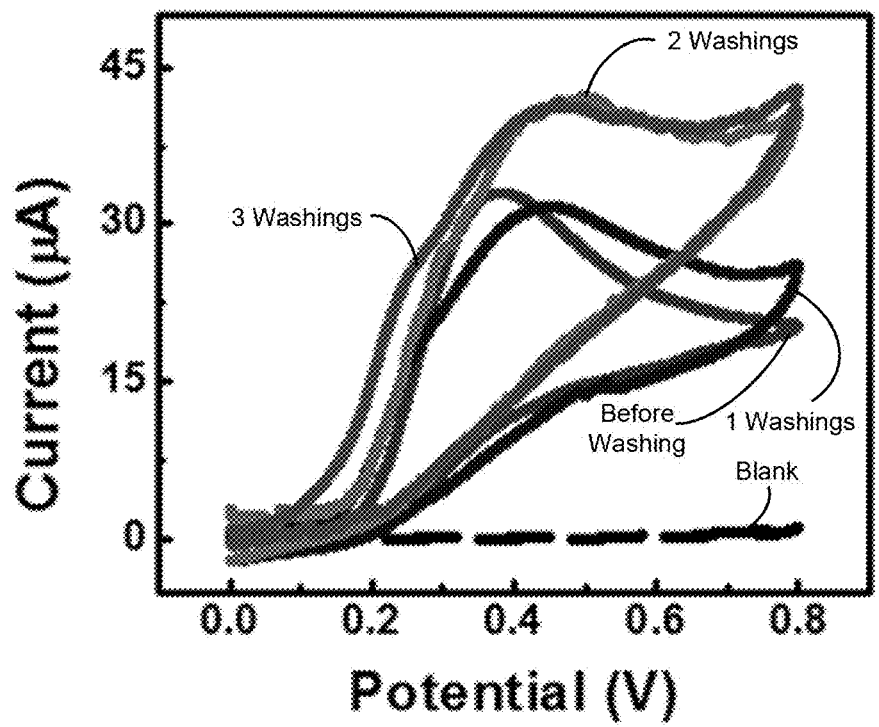
FIG. 35A shows an IV data plot showing the effect of repetitive washing cycles upon the CV waveform generated at the tattoo biosensor (on porcine skin) using 2.5 mM UA.

The subjection of conventional SPEs on rigid and flexible substrates to repeated chemical and mechanical degradation is expected to have deleterious impact on their electrochemical behavior, thus precluding them from epidermal integration. Advantageously, for example, the disclosed T3 electrochemical sensors can rectify these challenges, e.g., through the inclusion of CFs in the ink matrix as well as through their strongly-adhesive (and flexible) backbone. Exemplary implementations were performed to evaluate the exemplary T3 sensors against chemical degradation, e.g. such as subjection to repetitive washing cycles (e.g., $t_{wash}$=5 s with hand soap) to emulate hand-washing or bathing. For example, the washing involved generating a thorough lather with hand soap under a continuous stream of tap water for 5 s and subsequently drying the skin sample with a towel. FIG. 35A shows an IV data plot showing the effect of repetitive washing cycles upon the CV waveform generated at the tattoo biosensor (on porcine skin) using 2.5 mM UA. As shown in FIG. 35A, although washing did impart relatively minor degradation in the waveform, e.g., shown from the well-defined peaks corresponding to the oxidation of UA. Additionally, for example, the peak current deviated from the baseline measurement (before washing) by no more than 15% at the conclusion of the implementations. Moreover, for example, an increase in the oxidation current following washing may reflect the exposure of a larger active electrode area. The peak potential, however, remained stable throughout the course of the implementations.

Figure 35B:
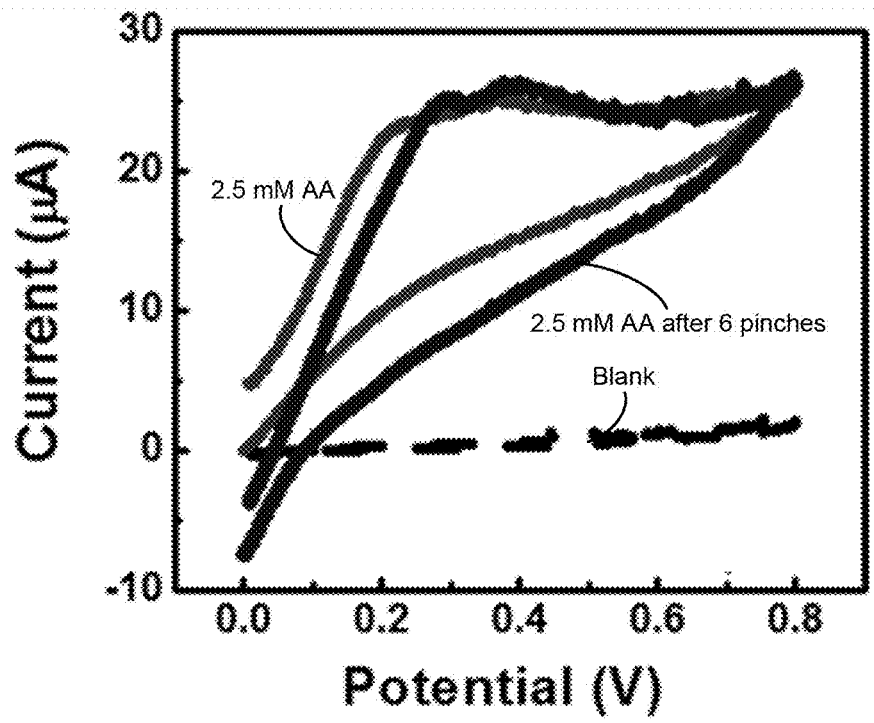
FIG. 35B shows an IV data plot displaying the response of the exemplary CF-reinforced T3 sensor to repetitive pinching operations employing 2.5 mM AA as a redox probe.

Exemplary implementations were performed to evaluate the effect of repetitive pinching of the tattoo patterned sensors. An exemplary CF-reinforced T3 sensor was applied to porcine skin and repetitively pinched for 2 s intervals, e.g., for six pinches. FIG. 35B shows an IV data plot displaying the response of the exemplary CF-reinforced T3 sensor to repetitive pinching operations employing 2.5 mM AA as a redox probe. The exemplary data indicate that repeated pinching of the sensor produced minimal degradation in the electrochemical performance. For example, both the peak current and peak potential remained stable throughout these pinching experiments, thereby demonstrating the capability of high-fidelity electro-analytical operations of the disclosed sensors under the severe demands imparted by epidermal wear.

Figure 35C:
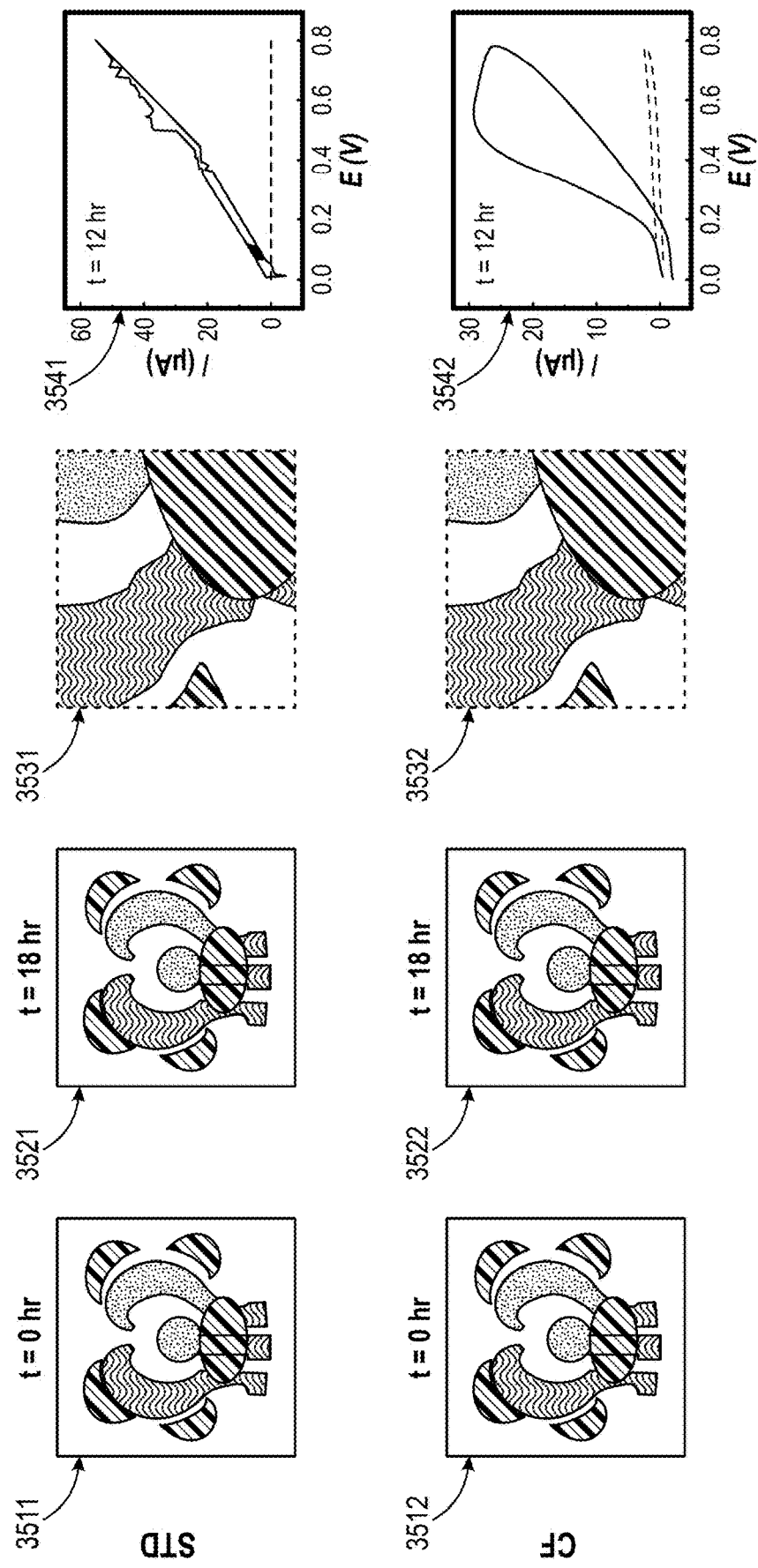
FIG. 35C shows images captured immediately following the application of the T3 sensors on skin for an exemplary T3 sensor and an exemplary CF-reinforced T3 sensor, respectively, and images captured after 18 hours of continuous epidermal wear of the exemplary T3 sensor and the exemplary CF-reinforced T3 sensor, respectively.

Exemplary implementations were performed with extended durations of routine wear of an exemplary T3 sensor. FIG. 35C shows images 3511 and 3512 captured immediately following the application of the T3 sensors on skin for an exemplary T3 sensor and an exemplary CF-reinforced T3 sensor, respectively, and images 3521 and 3522 captured after 18 hours of continuous epidermal wear of the exemplary T3 sensor and the exemplary CF-reinforced T3 sensor, respectively. A close inspection of the images 3521 and 3522 revealed some cracking (e.g., at the Ag/AgCl-insulator and carbon-insulator interfaces) for the exemplary T3 sensor without CFs, as shown in the image 3531 of FIG. 35C, and substantially no cracking or degradation for the exemplary CF-reinforced T3 sensor, as shown in the image 3532 of FIG. 35C. FIG. 35C also includes cyclic voltammogram data plots 3541 and 3542 for 0.5 mM UA at the exemplary T3 and CF-reinforced T3 sensors, respectively, following 12 hours of continuous wear of both sensors, e.g., with a scan rate of 100 mV/s. The response data recorded at the non-CF-reinforced sensor in the plot 3541 exhibited substantial distortion, e.g., as compared to the well-defined anodic UA oxidation peak visible at the exemplary CF-reinforced sensor in the plot 3541. A comparison with the voltammograms obtained from previous implementations with UA at unperturbed electrodes also corroborated that the exemplary CF-reinforced sensor is capable to yield high-fidelity electroanalytical performance over extended wear.

The disclosed technology includes techniques to the formation of biosensors and chemical sensors that exploit electrochemical detection methodologies such as amperometry, voltammetry, potentiometry, and electrochemical impedance spectroscopy. Thus, for example, exemplary techniques includes proper patterning of electrodes to form a complete electrochemical system, as well as the selection of an appropriate layering and ink formulation to facilitate the electrochemical response. The disclosed techniques can advance the field of non-invasive on-body continuous-monitoring biosensors.

For example, the majority of personal blood glucose monitors rely on disposable screen printed enzyme electrode test strips. These single-use electrode strips are mass produced by rapid and simple thick-film screen printing microfabrication techniques. Owing to its reliability and low cost, the diabetic monitoring industry has leveraged this fabrication concept for the past 30 years and has perfected the technology over this period such that analytically-precise results are now achievable, even when this fabrication methodology is migrated to the detection of other physiologically-relevant analytes such as metabolites, proteins, and DNA. The disclosed temporary transfer tattoo epidermal biosensing techniques enable the biosensor contingent to be transferred directly to the skin for the direct and non-invasive monitoring of the wearer's biochemical physiology and/or surrounding environment. For example, the exemplary biosensors can be transferred and include the ability to tolerate repeated bending and stretching operations typically associated with on-body wear, and its extended stability on the skin. For example, this paradigm can enable continuous monitoring of the wearer's biochemical physiology and/or surrounding environment, in direct contrast with state-of-the art invasive "single-shot" readings such as with blood glucose test strips for diabetics. In this manner, decreased overhead can be achieved, ultimately lowering the per-strip cost. Also for example, the biosensor pattern can be duplicated and arrayed as needed to parallelize the sensing operation, thereby yielding a substantially increased quantity of sensors per unit area.

In another aspect of the disclosed technology, techniques, systems, and devices are described for fabricating and implementing tattoo-based potentiometric ion-selective electrochemical biosensors and chemical sensors for epidermal and/or environmental monitoring on skin or a wearable item.

For example, the disclosed tattoo-based potentiometric ion-selective electrochemical biosensors and chemical sensors can include solid-contact ion-selective electrodes (ISEs) for non-invasive potentiometric monitoring of epidermal pH levels. The disclosed fabrication techniques of such devices include the use of temporary transfer tattoo paper with screen printing techniques and solid-contact polymer ISE methods. The disclosed tattoo-based potentiometric sensors exhibit rapid and sensitive response to a wide range of pH changes with no carry-over effects. These tattoo ISE sensors are capable of enduring repetitive mechanical deformation, which is a key requirement of wearable and epidermal sensors. The flexible and conformal nature of the tattoo sensors enable them to be mounted on nearly any exposed skin surface for real-time pH monitoring of the human perspiration, as illustrated from exemplary response data acquired from exemplary implementations during strenuous physical activity.

Potentiometric ISEs have witnessed widespread use in various researches, biomedical and industrial domains. Conventional ion-selective sensors include a membrane-based ion-selective electrode and a reference electrode, both of which require an internal solution to ensure a stable and sensitive response. Although these sensors have been widely used in various applications, their intrinsic design imposes inherent limitations upon specific in vivo and ex vivo applications, particularly, for example, the internal solution complicates the fabrication process and limits their miniaturization.

The disclosed technology includes highly flexible and conformal integrated potentiometric sensors, compatible with the non-planarity and irregularities of the human anatomy and capable of enduring prolonged mechanical strain, which can be successfully implemented in epidermal chemical monitoring, e.g., including pH measurements.

The disclosed wearable electrochemical sensing devices include a conformal geometry that is compliant with skin and can withstand repeated mechanical stress while minimizing intrusion in the wearer's routine. In some implementations, the disclosed wearable electrochemical sensing devices can be configured as textile-based sensors for in the field monitoring of the environment and on-body monitoring, in which the textile-based sensors conform to the wearer's anatomy while enabling unobtrusive sensing. Such wearable devices can provide detection of both physiological and environmental analytes. The design configurations of the disclosed technology enable continuous contact of detectable analytes with the sensor surface while worn a user's body (e.g., on skin or a wearable item).

Figure 36A:
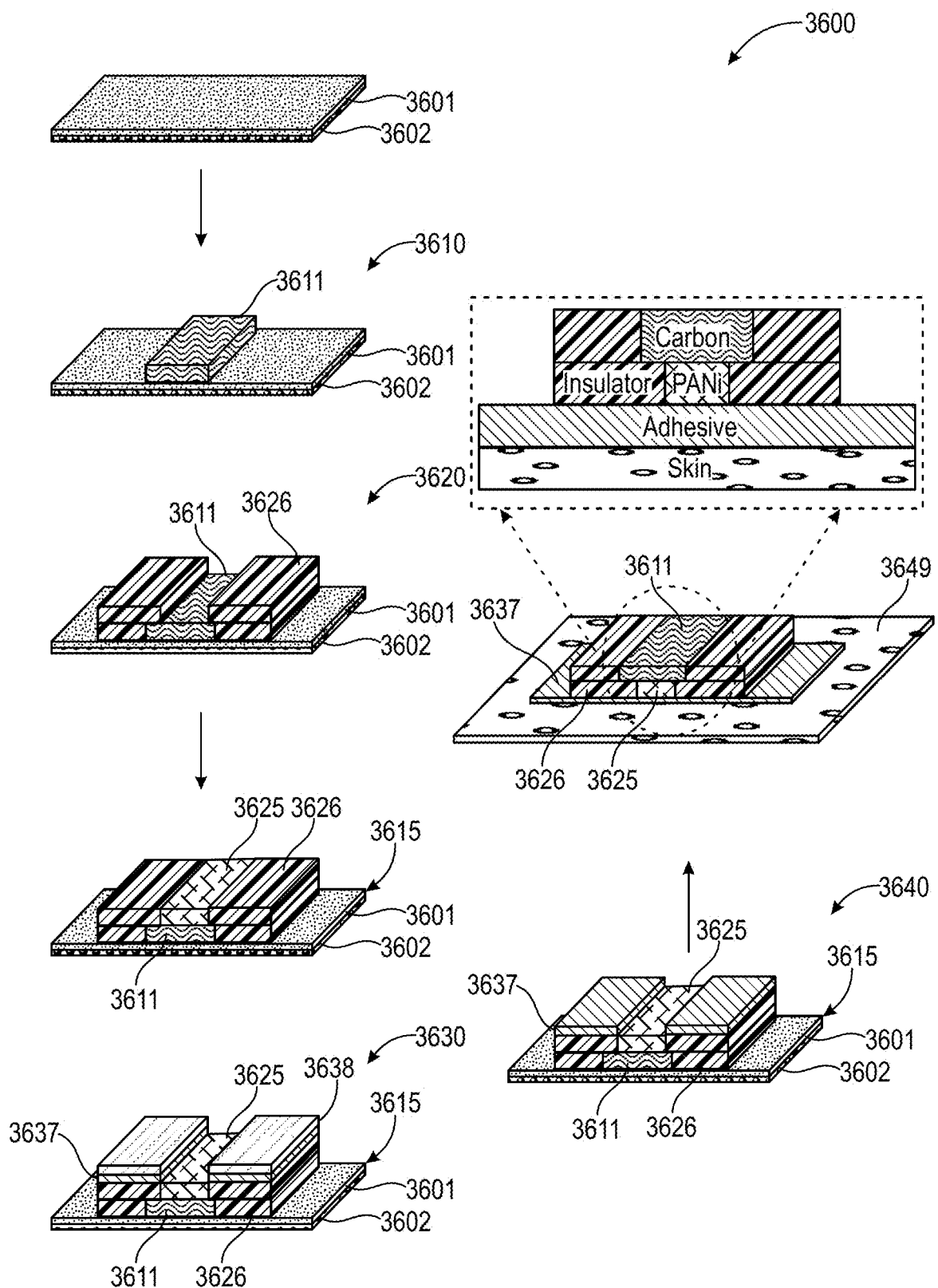
FIG. 36A shows a process diagram illustrating a fabrication method to produce epidermal electrochemical sensors with ion-selective electrodes.

In some implementations of the tattoo-based potentiometric devices, exemplary devices include polyaniline-based solid-contact ISEs and temporary transfer tattoo paper, and can be fabricated using hybrid screen printing techniques. FIG. 36A shows a process diagram illustrating a fabrication method 3600 to produce epidermal electrochemical sensors with ion-selective electrodes. The method 3600 includes a process 3610 to form electrode structures 3611, e.g., such as carbon-based material electrodes, by using thick-film screen printing on a release agent layer 3601 coated over a base paper substrate 3602. For example, the electrode structures 3611 can be patterned on the release agent 3601-coated paper substrate 3602, in which the electrode pattern is configured in a particular design layout. The method 3600 includes a process 3620 to form electrically insulative material 3626 and poly(aniline) (PANi) 3625 to form a temporary transfer tattoo solid-contact ISE sensor 3615. The method 3600 includes a process 3630 to form an adhesive sheet 3637 with a protective coating 3638 to the T3 ISE electrochemical sensor component 3615 to form a T3 ISE electrochemical sensor device 3625, which is capable of attaching to skin (or a wearable item) for one of sensing analytes in the external environment of the skin or fluids present on the skin. In some implementations of the method 3600, a process 3640 can include removing the protective sheet 3638 from the adhesive sheet 3637 of the T3 ISE electrochemical sensor device 3625 to enable transfer of the T3 ISE electrochemical sensor device 3625 on a receiving surface 3649, e.g., including skin or a wearable item An inset illustrative schematic of the applied T3 ISE electrochemical sensor device 3625 on the receiving surface 3649 (e.g., skin) shows the layers of materials of the exemplary device.

FIG. 36B shows an image of an exemplary ISE tattoo sensor including two electrodes, e.g., including an ISE and a reference electrode, and connection points that can interface with a voltmeter, for example, via electrically conductive conduits. For example, the disclosed fabrication methods allow development of the exemplary ISE tattoo sensors in a variety of designs, e.g. such as the 'smiley face' design of the exemplary ISE tattoo sensor shown in FIG. 36B. In this example, the sensor design includes one 'eye' of the smiley face acting as the pH-sensitive ISE while the other 'eye' functions as the reference electrode, e.g., thus concealing the complete sensor contingent in an artistic manner.

These exemplary 'smiley face' shaped-tattoo sensors can be readily fabricated using tattoo base paper, electrode inks, e.g., including carbon and/or Ag/AgCl, and insulator inks, in which the tattoo sensor fabrication employs a distinct stencil pattern for each layer. An adhesive sheet can later be applied to the electrode- and insulator-printed tattoo paper for subsequent transfer on various substrates. For example, poly (aniline) (PANi) exhibits pH-sensitive conductivity, e.g., demonstrated with the reversible emeraldine salt (ES)-emeraldine base (EB) transition (acid-base reaction), and can thus be used in the disclosed solid-state pH electrochemical sensors. Additionally, for example, PANi has minimal cytotoxicity and causes negligible skin irritation and sensitization. Thin films of PANi can be produced on the patterned electrodes or other structures of the disclosed devices via electropolymerization techniques with high reproducibility, and in doing so, for example, the fabrication of these exemplary PANi-based ISEs do not require surface pre-treatment. These characteristics along with the attractive performance make PANi well-suited for the disclosed biocompatible, epidermal tattoo-based potentiometric sensors.

The resulting tattoo ISE sensor devices can withstand repeated bending and stretching operations, which are of substantial relevance to wearable epidermal sensors.

Exemplary implementations of the disclosed potentiometric ion-selective electrochemical sensor technology were performed, which included the described materials, procedures, and data.

The exemplary implementations described herein included the use of the following materials and equipment. For example, potassium phosphate monobasic ($KH_2PO_4$), potassium phosphate dibasic ($K_2HPO_4$), hydrochloric acid (HCl), Nafion® 117 solution, aniline and citric acid were obtained. Aniline was further purified by double distillation prior to use. Carbon fibers (8 μm diameter, 6.4 cm length, 93% purity) were obtained and their length was reduced to ~0.5 mm (e.g., by cutting with a sharp blade), followed by thorough cleaning in acetone. The exemplary implementations were conducted at room temperature, and solutions were prepared using ultra-pure deionized water (18.2 MΩ·cm). For example, electrochemical cleaning, deposition, and potentiometric analysis were performed using a CH Instrument (Austin, Tex.) model 630C electrochemical analyzer. A Mettler Toledo (Columbus, Ohio) S20 SevenEasy glass-electrode digital pH meter was employed for pH measurements, for example. A miniaturized multimeter (Sinometer MS8216 DMM) was used for on-body measurements in the exemplary implementations.

Exemplary ISE tattoo sensor devices were designed to conceal the electrodes in a 'smiley face'. The design included one eye functioning as the pH-sensitive ISE while the other eye functioning as the reference electrode. As exemplified in FIG. 36B, the two ears of the exemplary ISE tattoo sensor device were employed as connectors for attachment to a digital multimeter. For example, design of the exemplary smiley face sensor pattern was performed in AutoCAD (Autodesk, San Rafael, Calif.) and fabricated on 75 μm thick stainless steel and mesh stencils (Metal Etch Services, San Marcos, Calif.). For example, a unique stencil pattern was used for each electrode layer (e.g., including a carbon layer, an Ag/AgCl layer, and an insulator material). For example, the conductive Ag/AgCl ink (E2414), the carbon ink (E3449), and the insulator ink (E6165) were obtained, and an exemplary transparent dielectric ink (5036) was obtained. Carbon fiber segments were dispersed within the semi-conductive carbon ink matrix to increase the tensile strength of the electrode. Printing was accomplished via an MPM SPM semi-automatic screen printer (Speedline Technologies, Franklin, Mass.). Blank temporary transfer tattoo paper and the accompanying adhesive substrate were used without further derivation.

In some implementations of the method 3600, a fabrication process can first involve the printing of the blue insulator ink, followed by the Ag/AgCl ink and the carbon ink, and finally, by another blue insulator layer. Following each routine, for example, the ink can be cured, e.g., such as at conditions including 90° C. for 15 min. Subsequently, for example, a 30 wt % KCl-doped transparent insulator can be screen printed only on the surface of the reference electrode and then cured, e.g., such as at conditions including 90° C. for 6 min. Finally, for example, a total of 6 μL of the 5% Nafion solution can be drop-casted on the Ag/AgCl reference electrode and left to dry, e.g., for an overnight duration. This exemplary fabrication process was implemented to produce an exemplary ISE tattoo sensor device used in subsequent implementations described.

In some implementations of the fabrication process, for example, prior to the electropolymerization of the aniline material, the working electrode was electrochemically cleaned by five cyclic voltammetric scans in 0.5 M HCl over the potential range of −0.3 V to 1.1 V (e.g., an external Ag/AgCl reference electrode and an external Pt wire auxiliary electrode were used in this processing step). Surface modification with PANi was performed in a 0.1 M aniline/1 M HCl solution by cyclic voltammetry from −0.2 V to 1.0 V (vs. Ag/AgCl) at 0.1 V/s. In such examples, electropolymerization was first performed for 12 cycles, then a fresh solution was dispensed on the surface, followed by additional 13 cycles. A total of 25 cycles were thus executed for the complete polymerization of the working electrode surface. During the exemplary cleaning and polymerization steps, in this example, the screen printed Ag/AgCl electrode was protected from the electrolyte solution to avoid its damage by highly acidic solutions and aniline. After air-drying the exemplary PANi film, the adhesive sheet was applied to the tattoo. For proper contact between the two electrodes and analyte solution, this adhesive sheet was excised to remove a rectangular-shaped region around the two electrodes (e.g., the two eyes). The as-prepared ISE tattoos were then ready for transfer and evaluation.

Exemplary implementations of the fabricated ISE tattoo sensor devices were examined in vitro by applying them onto hard plastic substrates prior to on-body epidermal studies. In some exemplary implementations, the tattoo ISE sensors were analyzed within the pH range of human sweat (e.g., pH 3-7, with a mean around pH 5) using standard McIlvaine's buffers. For example, since human perspiration can exhibit continuous fluctuations of pH, a practical pH sensor must encompass a rapid and near-instantaneous response to pH modulations over this range.

FIG. 37A shows a data plot of the potential-time response of an exemplary ISE tattoo sensor for decreasing pH levels and an inset plot of electrical potential versus pH, e.g., using the standard McIlvaine's buffers. The data plot of FIG. 37A displays a characteristic potential-time recording at the exemplary tattoo-based potentiometric sensor for decreasing pH levels between 7 to 3 (in one-unit decrements). This real-time recording illustrates that the disclosed ISE tattoo sensors exhibit a nearly instantaneous response to varying pH solutions, e.g., yielding 80% of their steady-state signal within the first 10 sec while a completely stabilized signal was observed within 25 sec. The resulting calibration plot (shown in the inset of FIG. 37A) displays a sub-Nernstian behavior, e.g., with a mean slope ($s_x$) of 50.1 mV/pH and a relative standard deviation (RSD) of 3.72% (n=4). The pH sensitivity (slope) and conductivity of PANi depend on orientation of the crystalline and amorphous phases of PANi. The observed sub-Nernstian response of the PANi tattoo sensors can be attributed to inferior orientation of these phases. As discussed later, mild mechanical deformations to the ISE tattoo sensor devices caused reorientation of the conducting and amorphous phases and improved the pH-sensitivity to a near-Nernst response. Batch-to-batch variations between the tattoos also exhibited a low RSD of 4.63 (n=4), hence indicating the capability of the described fabrication techniques to produce reproducible devices.

It has been observed that the pH of human perspiration fluctuates according to the respiration rate. As such, the exemplary ISE tattoo sensor devices must also exhibit minimal carry-over in order to monitor such dynamically-fluctuating pH environments. To investigate this parameter, the ISE tattoos were subjected to operation in varying pH solutions and consecutive measurements recorded without reconditioning or rinsing of the tattoo surface.

FIG. 37B shows a data plot of the potential-time response of the exemplary ISE tattoo sensors, which demonstrates the reproducibility of the sensors in response to large pH fluctuations. The data plot of FIG. 37B demonstrates the dynamic response of the exemplary tattoo ISE sensor devices to alternate and multiple exposures to solutions of different pH. The exemplary device responded rapidly and favorably to these dynamic pH changes, regaining rapidly the same potentiometric signal for a given solution pH during this continuous operation. The negligible carry-over of the exemplary tattoo-ISE response reflects the fact that the emeraldine salt (ES)-emeraldine base (EB) transition of PANi is fast and reversible. Thus, the tattoo sensors have the capability to perform effectively under continuously-varying pH milieu, viz., in situ pH measurement of human perspiration with low carry-over.

A distinctive feature of wearable sensors is their ability to endure prolonged mechanical strain, which is a key requirement of wearable and epidermal sensors. This is especially true in the sports, athletics, fitness and military domains. Exemplary implementations of the fabricated ISE tattoo sensor devices were performed to examine the influence of relevant mechanical stress upon the sensor performance prior to their integration with the epidermis.

For example, the influence of mechanical strain permutations, including repeated bending and stretching, upon the potentiometric response were examined. In some examples, the exemplary ISE tattoo sensor devices were subjected to a total of 50 bending and 40 stretching applications. For these exemplary implementations, the tattoos were transferred onto GORE-TEX as its viscoelastic behaviour mimics that of skin. In the bending implementations, the tattoo was bent to 180° and maintained at that position for 5 sec prior to release. The response of the tattoo was measured subsequent to 10 bending iterations from pH 7 to 3. The effect of stretching upon the electrochemical performance of the tattoos was analyzed. In the stretching implementations, the exemplary ISE tattoo sensor devices were stretched an additional 10% in lateral extent and maintained at that position for 5 sec followed by release and investigation of the response. In cases of stretching deformation, the response was measured at an interval of 5 consecutive stretching operations.

Figure 38A:
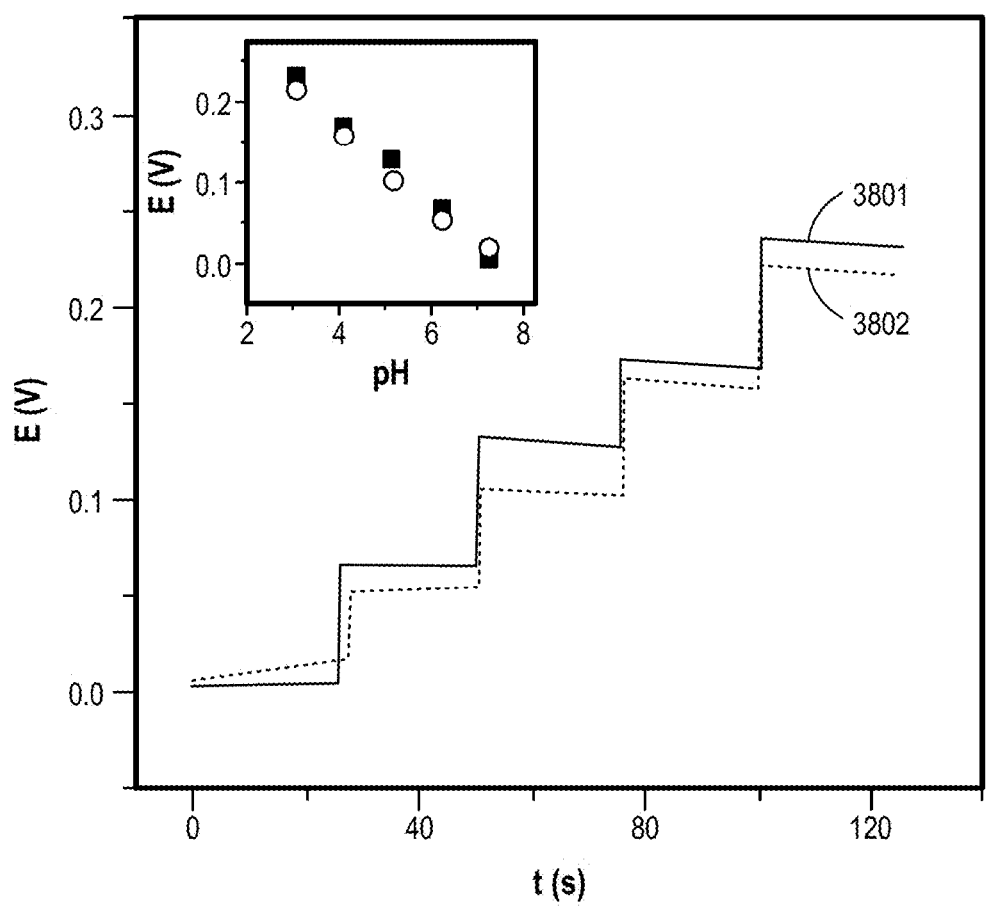
FIGS. 38A and 38B show a data plot and images representing the influence of repeated mechanical strain (e.g., bending) upon the response of an exemplary tattoo ISE device.
Figure 38B:
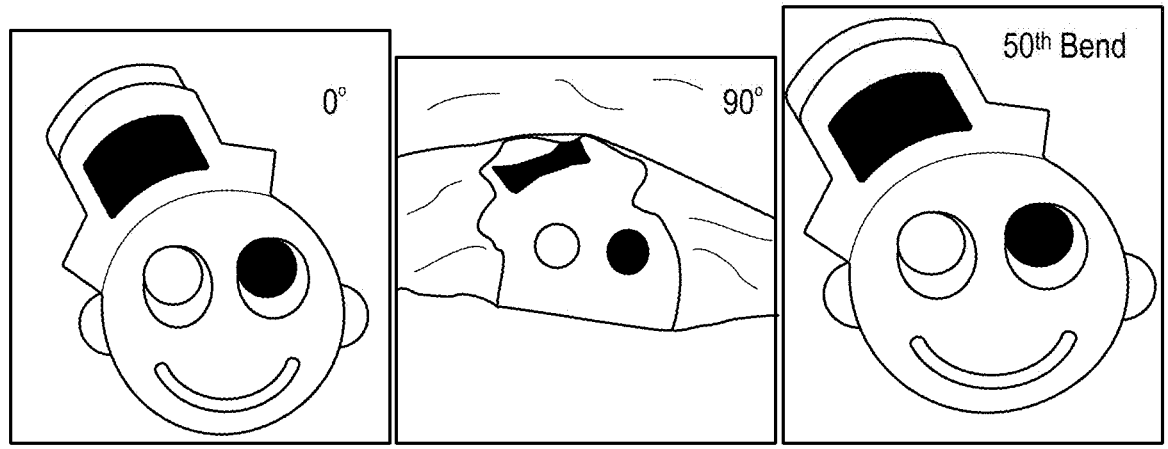

FIGS. 38A and 38B show a data plot and images representing the influence of repeated mechanical strain (e.g., bending) upon the response of an exemplary tattoo ISE device. The data plot in FIG. 38A shows the pH-responsive behavior of the exemplary ISE tattoo sensor over the 3-7 pH range prior to stretching (black waveform 3801 and black squares in the inset plot) and following the 50$^{th}$ bending on GORE-TEX (red waveform 3802 and red dots in the inset plot), e.g., one unit pH decrement per addition. The images of FIG. 38B show the exemplary tattoo ISE sensor device applied to the cubital fossa at 0° bending, 90° bending, and after the 50$^{th}$ bending.

Figure 39A:
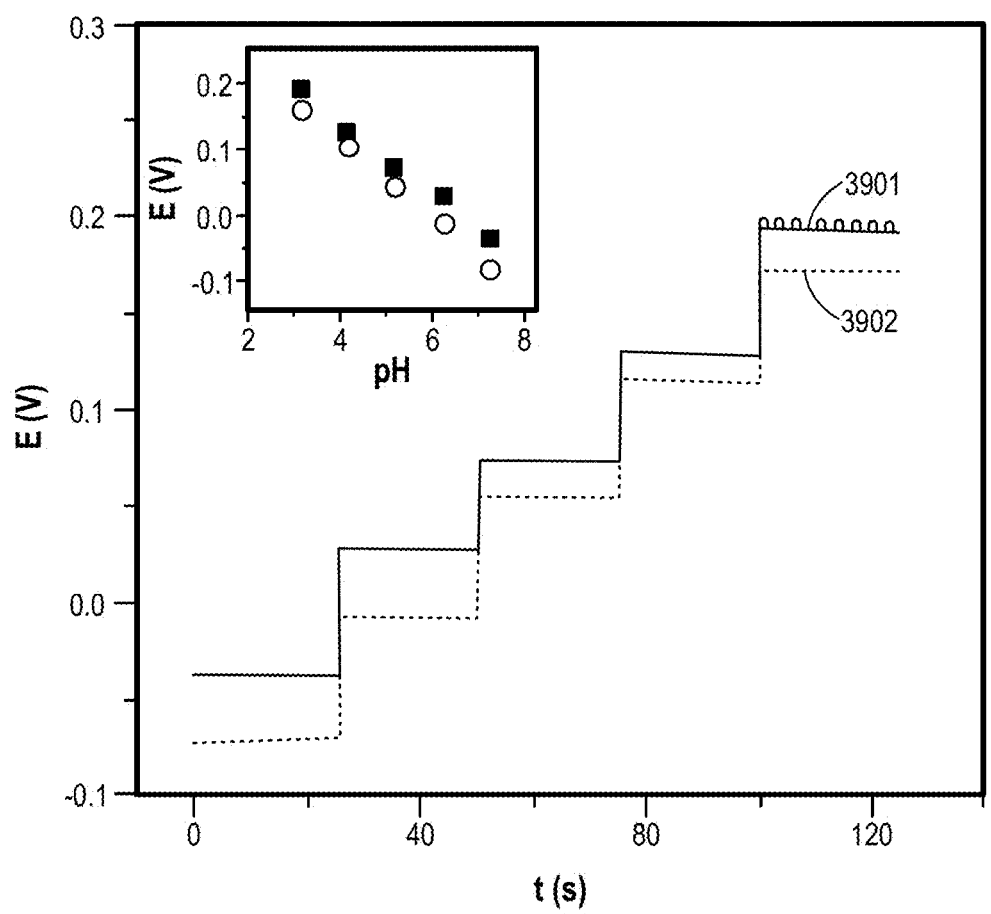
FIGS. 39A and 39B show a data plot and images representing the influence of repeated mechanical strain (e.g., stretching) upon the response of an exemplary tattoo ISE device.
Figure 39B:
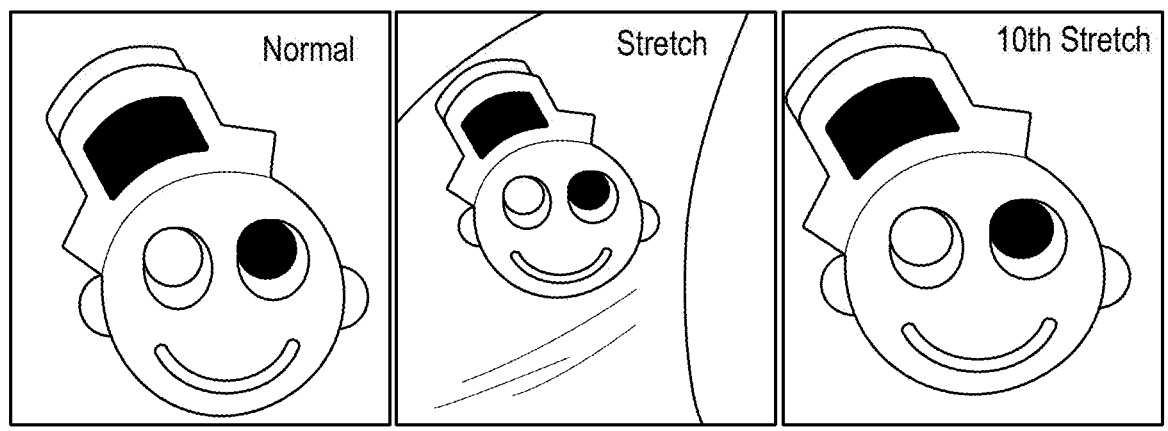

FIGS. 39A and 39B show a data plot and images representing the influence of repeated mechanical strain (e.g., stretching) upon the response of an exemplary tattoo ISE device. The data plot in FIG. 39A shows the pH-responsive behavior of the exemplary ISE tattoo sensor over the 3-7 pH range prior to stretching (black waveform 3901 and black squares in the inset plot) and following the 40$^{th}$ bending on GORE-TEX (red waveform 3902 and red dots in the inset plot), e.g., one unit pH decrement per addition. The images of FIG. 39B show the exemplary tattoo ISE sensor device applied to the forearm at normal, after the 1$^{st}$ stretch, and after the 10$^{th}$ stretch.

It is noted, for example, the deformation created during these exemplary implementations of the exemplary tattoo ISE sensor device utilized yielded a beneficial effect upon the response of the sensor. Specifically, for example, in the absence of applied deformation, the exemplary tattoo ISE sensor device yielded a sub-Nernstian response (e.g., 52.8 mV/pH), e.g., as observed with plastic substrates. The response of the exemplary tattoo ISE sensor device improved to 59.6 mV/pH within the first 10 bending iterations (as shown in the data plot of FIG. 38A). Thereafter, the response stabilized to yield a final slope of 57.5 mV/pH following the $50^{th}$ bending iteration. The RSD for the entire exemplary implementation was 5.71%. A similar trend was observed for the stretching implementations, e.g., where an initial slope of 53.0 mV/pH increased to 58.2 mV/pH following the $10^{th}$ stretching iteration and finally stabilized at 57.54 mV/pH after the $40^{th}$ stretch (as shown in the data plot of FIG. 39A). A 4.72% RSD was obtained in this exemplary case. The sensitivity enhancement observed may be attributed to uncoiling and reorientation of the crystal and amorphous phases of PANi and the subsequent improvement in its conductivity owing to mechanical deformation.

Visual analysis of the exemplary tattoo ISE sensors under bending and stretching were performed on the human skin. For the bending studies, for example, the exemplary tattoo ISE sensor device was applied to the cubital fossa and the arm was bent completely until the fingers touched the scapula acromion, thus simulating the extreme deformation expected under heavy epidermal wear (as shown in the images of FIG. 38B). In the stretching scenario, for example, the exemplary tattoo ISE sensor device was applied to the forearm and then stretched repeatedly to the maximum extent (as shown in the images of FIG. 39B). These images reveal that the potentiometric sensors are quite resilient and that their structural integrity does not easily degrade. Accordingly, the exemplary tattoo ISE sensor device are well-suited for applications involving continuous motion of the substrate, e.g., as normally experienced by the human body.

There are growing demands for ion-selective sensors in the medical, sports, athletics, and fitness fields where point-of-care devices for the monitoring of physiological conditions are required. Electrolytes (e.g., such as Na, Cl, K, and/or Mg) and pH levels of perspiration can readily yield information regarding the metabolic state of an individual as well as their respiration dynamics during a fitness routine. Thus, continuous pH analysis of human perspiration is of great importance in the areas of clinical diagnostics and sports medicine.

Exemplary implementations of the exemplary tattoo ISE sensor devices were performed to demonstrate such continuous, real-time physiological monitoring under various conditions. Exemplary tattoo ISE sensor devices were applied to different locations throughout the body (e.g., the neck, wrist and lower back) of an active, consenting volunteer (sex: male; age: 27; weight: 70 kg; height: 186 cm) while the multimeter readout unit was attached to the body using a commercially-available arm-band. For example, the multimeter leads were attached firmly to the connection points (e.g., the designed 'ears') of the exemplary tattoo ISE sensors using transparent tape. The elasticity of the tattoo substrate allows the exemplary potentiometric sensor to attach firmly to these different body locations. In these exemplary implementations, for example, the neck, wrist, and lower back areas were selected in order to vary operational conditions experienced by these sensors, as mechanical stress and local pH are expected to vary among these locations.

For example, the ISE application process and the subsequent mating of the sensor with the readout instrument required less than 5 min and was readily performed by the subject. During the experiment the subject used a stationary cycle in a gymnasium for a total of 40 min followed by a 10 min gradual cool down. The subject ingested no fluid (dehydrated state) during the entire exercise. Heart rate and cadence were maintained around 165 and 130 RPM, respectively. pH sensing of the subject's perspiration was performed by the exemplary ISE tattoo sensor devices and the data were collected at regular intervals using the miniaturized multimeter. To confirm that the tattoos yielded accurate readings, the regional pH was verified using a conventional pH meter and glass electrode.

Figure 40A:
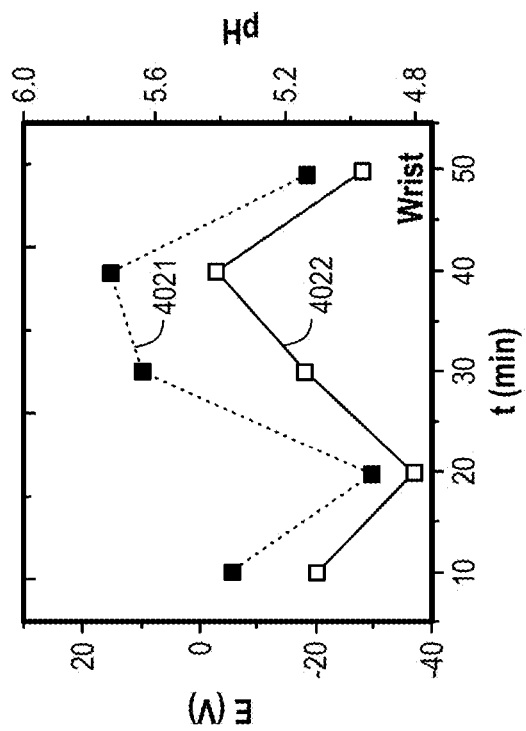
FIG. 40A shows a data plot of the real-time voltage-time response of an exemplary ISE tattoo sensor applied to a subject's neck to detect pH changes, e.g., as compared to that of a conventional pH meter.

FIG. 40A shows a data plot of the real-time voltage-time response of an exemplary ISE tattoo sensor applied to a subject's neck to detect pH changes (shown as waveform 4011), e.g., as compared to that of a conventional pH meter (with response shown as waveform 4012).

Figure 40B:
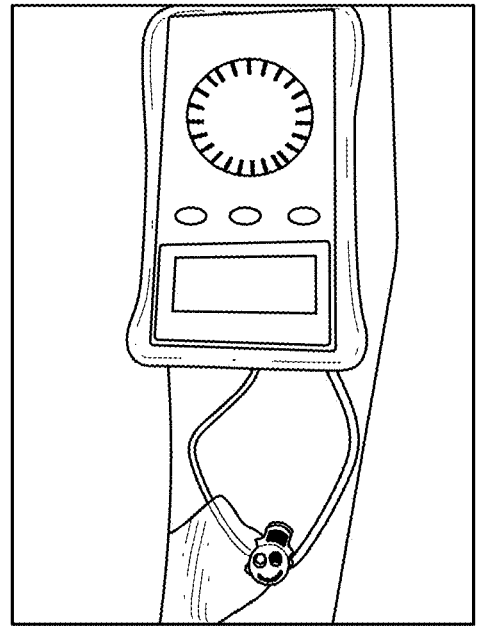
FIG. 40B shows a data plot of the real-time voltage-time response of an exemplary ISE tattoo sensor applied to a subject's wrist to detect pH changes, e.g., as compared to that of a conventional pH meter.

FIG. 40B shows a data plot of the real-time voltage-time response of an exemplary ISE tattoo sensor applied to a subject's wrist to detect pH changes (shown as waveform 4021), e.g., as compared to that of a conventional pH meter (with response shown as waveform 4022).

Figure 40C:
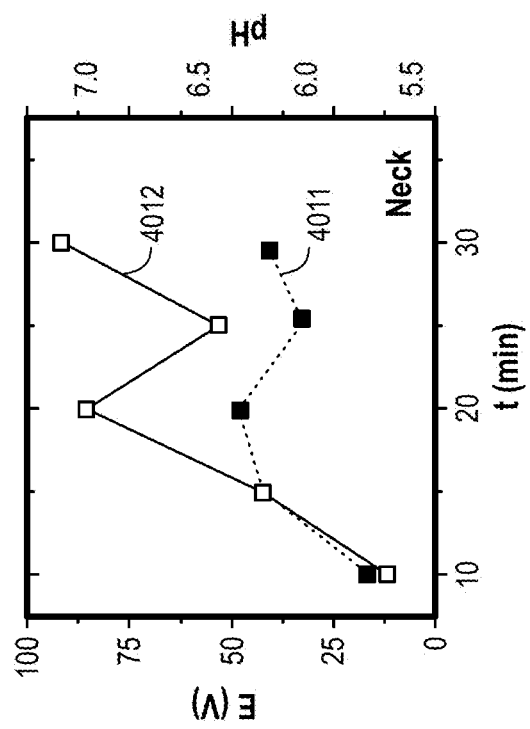
FIG. 40C shows a data plot of the real-time voltage-time response of an exemplary ISE tattoo sensor applied to a subject's lower back to detect pH changes, e.g., as compared to that of a conventional pH meter.

FIG. 40C shows a data plot of the real-time voltage-time response of an exemplary ISE tattoo sensor applied to a subject's lower back to detect pH changes (shown as waveform 4031), e.g., as compared to that of a conventional pH meter (with response shown as waveform 4032).

Figure 40D:
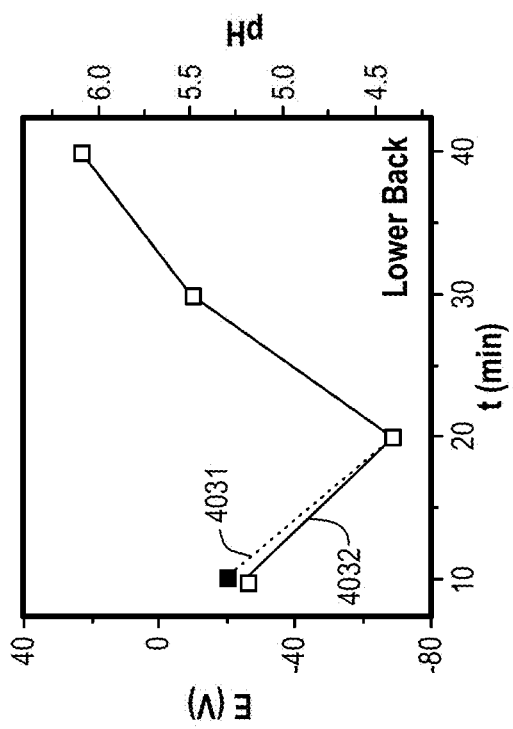
FIG. 40D shows an image showing the exemplary device used in these exemplary implementations (e.g., the tattoo ISE sensor interfaced with a digital multimeter) attached to the subject's wrist for the epidermal measurements of pH in human perspiration.

FIG. 40D shows an image showing the exemplary device used in these exemplary implementations (e.g., the tattoo ISE sensor interfaced with a digital multimeter) attached to the subject's wrist for the epidermal measurements of pH in human perspiration.

Although an athlete initially perspires at a low rate, this is soon followed by heavier perspiration as physical activity continues. Thus, an important requirement for such tattoo sensors is their ability to yield precise readings during a wide range of sweat flow rates. It was observed that during the first 10 min of exercise, the exemplary ISE tattoo sensor devices provided no response as the amount of perspiration generated was not sufficient to record a consistent open circuit potential. This was also true for the pH glass electrode. However, at the 10 min mark, sweat excretion became sufficient for the tattoo sensors to yield a stable reading. Initially, the pH measured at the three positions (e.g., the neck, wrist, and lower back) by the tattoo ISE sensors were almost the same (e.g., ~pH 5.3), as shown in FIG. 40A-40C.

In this exemplary implementation, the real-time sweat pH data obtained from the exemplary ISE tattoo sensor devices can be explained based on varying sweat rate at the respective body parts. The exemplary subject perspired most profusely in the vicinity of the neck, followed by the lower back and the wrists. As the sweat excretion rate increases, the relative concentration of lactate and pyruvate decreases due to dilution, and the pH concomitantly increases. The data plots of FIGS. 40A-40C illustrate that the exemplary ISE tattoo sensor devices performed favorably with a mean slope of ~54 mV/pH, and their potentiometric response at the different body locations followed closely the pH values recorded with the glass electrode.

During the entire course of the exemplary implementation, it was observed that the exemplary ISE tattoo sensor devices performed well during both moderate and profuse perspiration. However, owing to the combination of excessive sweating and the highly curvilinear morphology of the skin on the neck, the neck-based tattoo ISE sensor functioned reliably for about 30 min. It is also noted that the exemplary ISE tattoo sensor devices functioned satisfactorily even when minor cracks were observed (as long as connection to the multimeter was maintained). This can be attributed to the fact that the potentiometric response is independent of electrode area, e.g., which is in contrast to area-dependent voltammetric and amperometric type measurements.

In another aspect of the disclosed technology, techniques, systems, and devices are described for fabricating and implementing temporary transfer tattoo-based electrochemical biosensors for non-invasive monitoring of lactate in perspiration, e.g., in which the sensors are applied to skin or a wearable item.

Lactate is a key stress biomarker and has garnered substantial interest in the athletics field. Muscular fatigue is a major hindrance in an athlete's performance and thus extensive efforts are taken to improve one's stamina. This is especially true in intensive and endurance-based sports such as the triathlon, cycling, boxing etc. Lactate is widely recognized as an important biomarker of muscular exertion and fatigue and has been extensively utilized by coaches, exercise physiologists, and sports physicians to monitor an athlete's performance. When an individual engages in intense physical activity, the body makes the transition from aerobic to anaerobic respiration in order to satisfy the energy demands of the musculature. During this phase, the body consumes stored glycogen from the muscles to generate energy; an unwanted effect of this process is the production of lactate, which is associated with a burning sensation in the muscles. This process is known as "glycolysis" or "lactate acidosis". During glycolysis, the lactate levels in perspiration increases, as well. There exists a correlation between perspiration lactate and blood lactate, and therefore, perspiration can be used as the sample for the analysis of muscular exertion and fatigue in persons without the need for finger sticks or venipuncture.

The disclosed technology includes fabrication methods to produce temporary transfer tattoo electrochemical sensing devices for non-invasive enzymatic detection and quantification of lactate in human perspiration. Implementation of the disclosed T3 sensors can provide crucial insight into an athlete's metabolic response to controlled physical activity by offering critical insight into the temporal dynamics of lactate concentration in the perspiration. Currently, the gold-standard for lactate monitoring in the fitness, athletics, and sports domains is the use of blood lactate sensors, which are enzyme-functionalized electrochemical strips requiring finger stick blood samples, akin to blood glucose readings. The present blood lactate sensors show high sensitivity and selectivity towards lactate and are successful in detecting it within 5-15 seconds. However, a major drawback inherent to these sensors is their invasiveness and sample collection methodology. Furthermore, to obtain a detailed lactate profile, the blood is usually collected at a coarse interval of few minutes while the athlete engages in rigorous training, which invariably hinders performance. A non-invasive lactate sensor offering higher temporal resolution is thus highly desired.

The disclosed techniques for real-time non-invasive lactate sensing in human perspiration use the described printed electrochemical temporary transfer tattoo biosensors. These exemplary enzymatic T3 electrochemical biosensors are capable of adhering to the epidermis and demonstrate resiliency against continuous mechanical deformations common to epidermal wear. The biosensors can be implemented for real-time, on-body analysis for the detection and quantification of lactate in perspiration, e.g., during fitness and activity to provide useful insight into a user's health and athletic performance, in which the sensed data can be used for enhancing the athletic performance of the user.

Figure 41A:
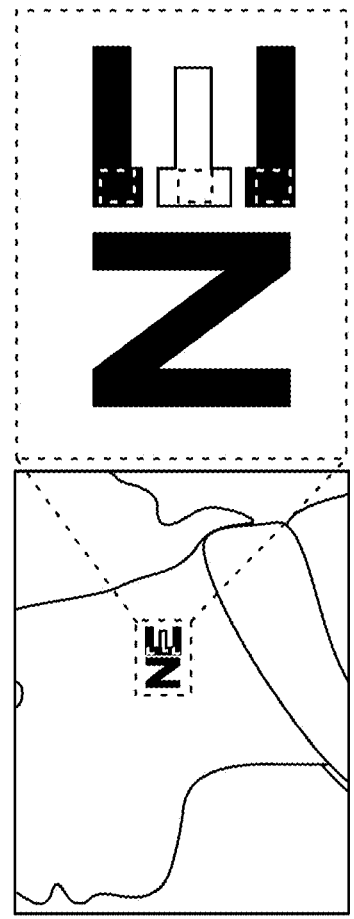
FIG. 41A shows a schematic illustration of an exemplary enzymatic T3 electrochemical sensor device including three electrodes (e.g., the working electrode, counter electrode, and reference electrode) configured in the design 'tattoo' design "NE" for electrochemical detection of L-Lactic acid.

In some implementations, an exemplary enzymatic T3 electrochemical sensor device includes a working electrode, a counter electrode, and a reference electrode configured on a flexible electrically insulative material structured to adhere to the skin (or a wearable item) of a user. FIG. 41A shows a schematic illustration of an exemplary enzymatic T3 electrochemical sensor device including three electrodes (e.g., the working electrode, counter electrode, and reference electrode) configured in the design 'tattoo' design "NE" for electrochemical detection of L-Lactic acid.

Figure 41C:
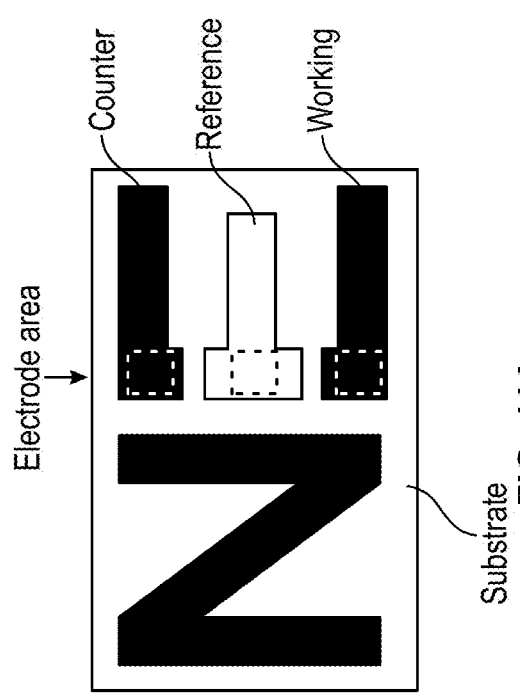
FIG. 41B shows a schematic illustrating an exemplary modified working electrode including the transducer layer coated by biocompatible polymer (e.g., chitosan).
Figure 41B:
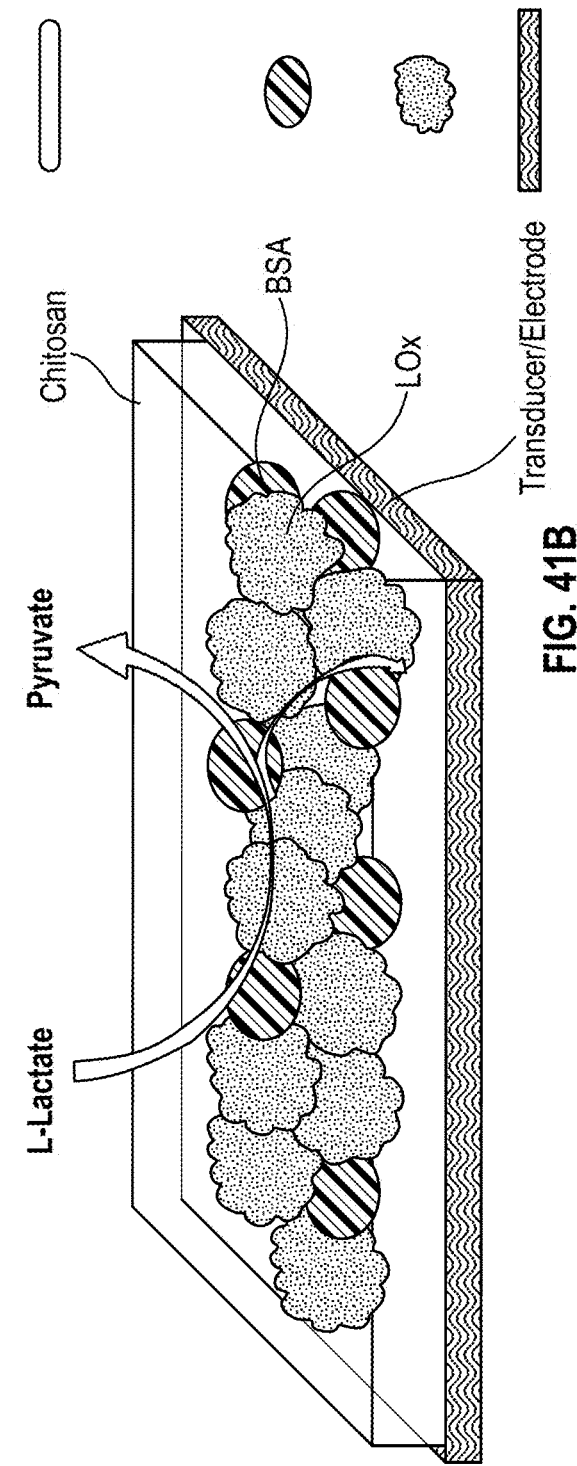

The working electrode of the exemplary T3 sensor can be functionalized with monolayers, ligands, enzyme catalysts and/or electroactive redox mediators, among other molecules or substances to enhance the detectability of the target enzyme. For example, in the exemplary T3 sensor of FIG. 41A, the working electrode is functionalized with tetrathiafulvalene (TTF), an electroactive redox mediator, and multi-walled carbon nanotubes in order to tether the active site of lactate oxidase, e.g., an enzyme catalyst, to form an electrochemical tranducer layer on the electrode surface of the working electrode. Also in this example, a layer of chitosan is deposited onto the enzyme-electrode to impede the efflux of the biocatalytic backbone from the electrode to the aqueous environment. FIG. 41B shows a schematic illustrating an exemplary modified working electrode including the transducer layer coated by biocompatible polymer (e.g., chitosan). Under this scheme, lactate diffuses through the chitosan membrane and is oxidized by LOx to pyruvate, releasing two electrons in the process, which give rise to an electrical current that can be measured between the working and counter electrodes.

For example, during bouts of physical exertion, the human body performs complex motions that cause the skin to undergo extreme mechanical deformations. Hence, wearable devices must survive such harsh conditions without compromising their performance. The disclosed T3 electrochemical biosensors possess the capability to withstand repeated iterations of mechanical deformation. Additionally, the disclosed T3 electrochemical biosensors possess the specificity to detect the target analyte or analytes desired, e.g., from human perspiration. FIG. 41C shows an image of the exemplary enzymatic T3 sensor device transferred on human skin.

Exemplary implementations were performed using the disclosed enzymatic T3 electrochemical sensor devices applied to skin of human subjects for in-situ sweat lactate profile recordings and analysis. A comparison of the profiles with previously reported data substantiate that the lactate epidermal biosensor platform performs desirably under conditions typical of use, e.g., demonstrating their utility as a non-invasive technique to assess lactate levels in order to assess and affect physical performance.

The exemplary implementations of the disclosed enzymatic T3 electrochemical sensor technology included the described materials, procedures, and data.

The exemplary implementations described herein included the use of the following materials and equipment. For example, tetrathiafulvalene (TTF), glutaraldehyde solution (8%), chitosan, acetic acid, bovine serum albumin (BSA), L-lactic acid, sodium phosphate monobasic (NaH$_2$PO$_4$), sodium phosphate dibasic (Na$_2$HPO$_4$), D(+)-glucose, L(+)-ascorbic acid, uric acid and creatinine were obtained and utilized in the exemplary implementations. Additionally, L-Lactate oxidase (LOx) and carboxy-functionalized multi-walled carbon nanotubes (MWNTs) were also acquired and used. Exemplary reagents were used without further purification. Carbon fibers (CFs) (e.g., 8 µm diameter, 6.4 mm length, 93% purity) were obtained and further processing was performed to reduce their length to approximately 2 mm, for example, and the CFs were cleaned with acetone. Electrochemical characterization was performed at room temperature leveraging a CH Instruments (Austin, Tex.) model 1232A electrochemical analyzer.

Exemplary enzymatic T3 electrochemical sensor devices were designed in the shape of "NE" (e.g., acronym for "NanoEngineering"). An exemplary fabrication process, e.g., similar to that described in FIG. 36A, was employed. Briefly, for example, the fabrication of the exemplary "NE"-designed enzymatic T3 sensors included dispersing chopped carbon fibers within both semi-conductive carbon (E3449) and conductive silver ink (E2414), e.g., to a concentration of 1.5% and 1.2%, respectively, to increase the tensile strength of the electrodes. Corresponding stencil patterns were designed and used for printing each layer on tattoo base paper, following the sequence of carbon, silver and insulator, using an MPM-SPM semi-automatic screen printer (Speedline Technologies, Franklin, Mass.). As shown in FIG. 41A, the 'E' portion of the exemplary device includes a reference electrode (e.g., fabricated from the exemplary silver ink), and a counter electrode and a working electrodes (e.g., fabricated from the exemplary carbon ink). A transparent insulator was screen printed on top to confine the electrode areas. Following every screen printing step, the printed tattoo paper was cured at 90° C. for 15 min in a convection oven.

Upon the fabrication of the exemplary NE"-designed enzymatic T3 sensor device, the working electrode was further functionalized. For these exemplary implementations, MWNTs were first suspended in ethanol (e.g., 5 mg/mL), and sonicated for several hours until uniform suspension was achieved. The suspension was then mixed with 0.1 M TTF ethanol/acetone (e.g., 9:1 (v/v)) solution in a volume ratio of 2:1 and sonicated for 1 h. For example, 3 µL of MWNTs/TTF suspension was subsequently cast onto the open area of the working electrode. After the electrode completely dried, 3 µL of LOx solution (e.g., 40 mg mL$^{-1}$ with 10 mg mL$^{-1}$ BSA) was cast on the electrode and dried under ambient condition, and later covered with 2 µL of 1 wt % chitosan solution. The electrodes were then cross-linked with glutaraldehyde vapor overnight at 4° C.

The transfer process of the exemplary NE"-designed enzymatic T3 sensor device on a host surface (e.g., including human skin) was similar to the previously described process, for example, as in FIG. 36A, with minor modifications. For example, in these exemplary implementations, a void was maintained around electrode areas to facilitate the flow of perspiration among electrodes for the on-body tests. For the exemplary in vitro implementations, the exemplary NE"-designed enzymatic T3 sensor were applied to the host surface such that the bio-functionalized side faced upwards, while during the exemplary on-body implementations, the bio-functionalized side faced downwards (in direct contact with human skin).

The exemplary implementations included evaluating the electrochemical performances of the exemplary lactate T3 sensor in vitro by transferring it onto a rigid plastic substrate and/or onto a flexible GORE-TEX textile for mechanical integrity studies. These analyses were performed using 0.1 M phosphate buffer, pH 7.0. For example, the operation potential for the exemplary lactate T3 sensor was determined in vitro by applying linear sweep voltammetry with a scan rate of 1 mV/s from −0.2 to 0.2V using 8 mM L-lactate. The amperometric responses were recorded at a constant potential of 0.05 V for 60 s after 1 min incubation. In the exemplary stability implementations, for example, amperometric response to 8 mM L-lactate was conducted every 30 min for an 8 h-period. In between the exemplary implementations, the tattoo was kept at room temperature. For exemplary interference assessments, potential interferents with average concentration existing in human sweat were examined.

The exemplary implementations included evaluating the electrochemical performances of the exemplary lactate T3 sensor in on-body epidermal L-lactate sensing applications. For example, the exemplary implementations included healthy subjects asked to wear a tattoo lactate sensor on their deltoid in order to assess real-time lactate generation. The sensor was connected to the CHI analyzer using fine stainless steel wires, and the real-time lactate profile was recorded using amperometry (time interval: 5 s, potential: +0.05V). Subjects were asked to mount a stationary cycle, begin cycling at a steady, slow cadence for 10 min. Following this 'warm-up' period, subjects were instructed to cycle with an increasing resistance every 3 min until maximum he/she can reach. This process ensured that the anaerobic respiration threshold was attained, hence augmenting the excretion of lactate in the perspiration. Later subjects were asked to gradually reduce their cadence during a 10 min 'cool-down' period. The exemplary subjects ingested no fluid during the duration of the fitness routine. During the workout, blood lactate concentrations were measured using a commercial lactate sensor. The correlation between sweat and blood lactate concentration were analyzed.

As shown in FIGS. 41A and 41B, the exemplary lactate T3 electrochemical sensors included a functionalized working electrode forming a MWNTs/TTF/LOx/Chitosan matrix. For example, during high body activity, e.g., caused during sports, fat nutrition, stress, infections and/or organ malfunction, the usual aerobic metabolism is incapable of satiating the energy needs of the human body. In such times, the anaerobic process (glycolysis or lactate acidosis) is initiated wherein the stored glycogen is consumed to produce energy and lactate by muscle cells. The sweat lactate concentration is a function of glycolysis and sweat rate and changes continuously with time. Moreover, the lactate concentration of the human sweat depends on a person's metabolism and can vary between 3 mM to 50 mM. However, in most cases the sweat lactate concentration fluctuates within 3-25 mM. Thus a wide linear detection range coupled with fast response time is mandatory for an ideal sweat lactate sensor.

For example, in the case of lactate, typical lactate sensors are often based on two types of enzymes, lactate dehydrogenase and lactate oxidase. However, one must recognize that for LDH, NAD$^+$ must be employed as the cofactor, which represents a noteworthy challenge given that this molecule must be immobilized on the electrode to prevent it from leaching into the solution while being able to diffuse, with relative ease, to the enzyme's active site. The detection of lactate from LOx is usually at a high potential (>+0.65V). At such high potentials, other electroactive metabolites become active and lead to false data.

In the disclosed technology, for example, mediators, e.g., such as TTF, are used in the exemplary T3 electrochemical biosensors to achieve electrocatalytic conversion of L-lactate by LOx at lower potential, e.g., thus avoiding interference by other electroactive species. To further improve the efficiency of the exemplary lactate T3 sensors, MWNTs are dispersed together with mediator to serve as the electron transducer on the working electrode. Furthermore, given the aim of epidermal usage of the tattoo sensor, the tattoo was coated with a biocompatible chitosan layer that functions as physical barrier and limits the efflux of the catalytic backbone from the tattoo and onto the underlying skin. This exemplary functionalization scheme of the working electrode of the exemplary lactate T3 electrochemical sensor is shown in FIG. 41B.

Exemplary implementations of the exemplary lactate T3 electrochemical sensor devices were performed in in vitro applications. For example, linear sweep voltammetry was applied first in the presence and absence of L-lactate in buffer. In this example, the exemplary lactate T3 sensor showed a peak value around +0.05 V, e.g., indicating that the MWNTs/TTF/LOx/Chit exhibits selective catalytic ability towards the oxidation of L-lactate. The potential of +0.05 V was applied for all the following amperometric detections. The exemplary lactate T3 sensors were then implemented, for example, to identify the detection range and the response time. In this exemplary implementation, the LOx functionalized T3 devices were exposed to varying concentrations of lactate prepared using, for example, 0.1M sodium phosphate buffer (e.g., pH 7.0).

Figure 42A:
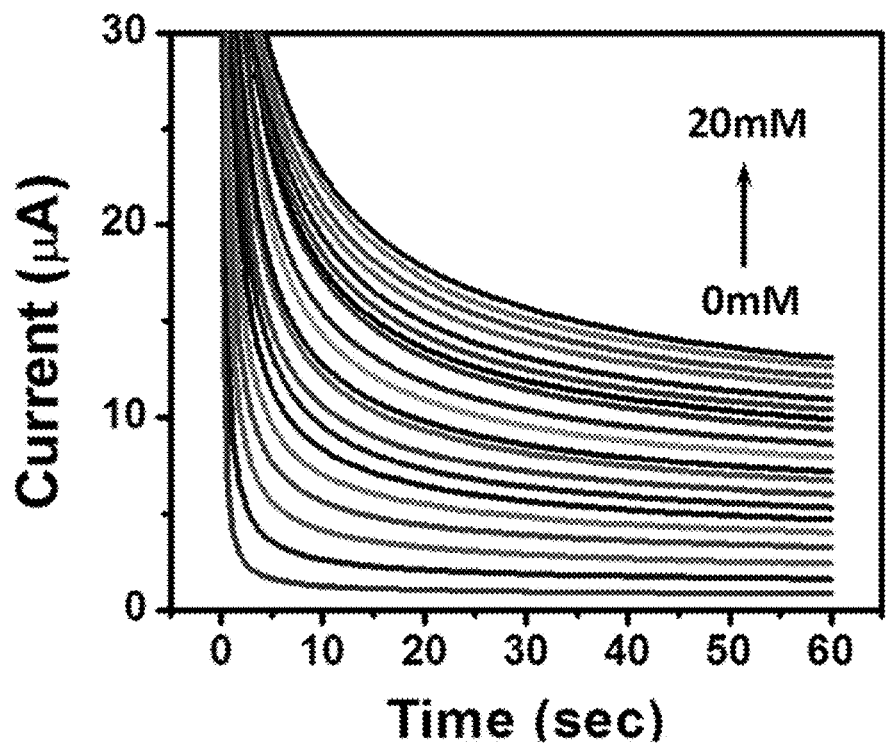
FIG. 42A shows an amperometric data plot of the responses for different concentrations of L-Lactate using the exemplary lactate T3 electrochemical sensor device, e.g., with 1 mM increment, $E_{applied}$=+0.05V.
Figure 42B:
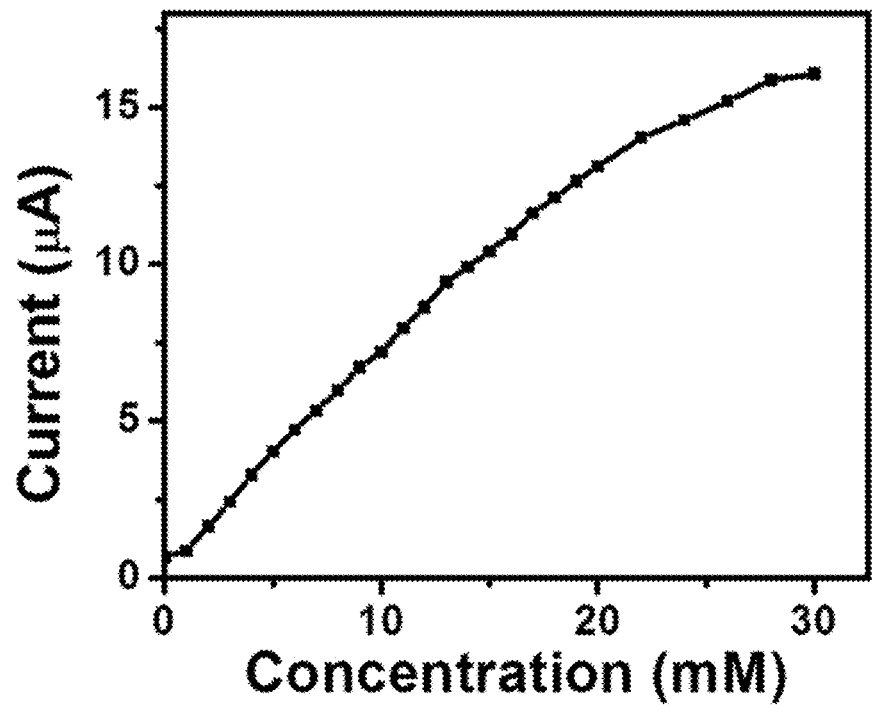
FIG. 42B shows the exemplary corresponding calibration plot of L-Lactate.

FIG. 42A shows an amperometric data plot of the responses for different concentrations of L-Lactate using the exemplary lactate T3 electrochemical sensor device, e.g., with 1 mM increment, $E_{applied}$=+0.05V. FIG. 42B shows the exemplary corresponding calibration plot of L-Lactate. As shown in FIG. 42A, the exemplary lactate T3 electrochemical sensors exhibited linear detection from 1 mM to 20 mM beyond which the signal gradually saturates with 644.2 nA/mM sensitivity and correlation (e.g., current (μA)=0.644 [L-lactate](mM)+0.689) between current and lactate concentration. For example, the large detection range and high sensitivity may be attributed to the high surface area provided by the MWNTs which can augment the enzyme loading capacity of the tattoos and the fast electron transfer between enzyme and transducer.

Figure 43A:
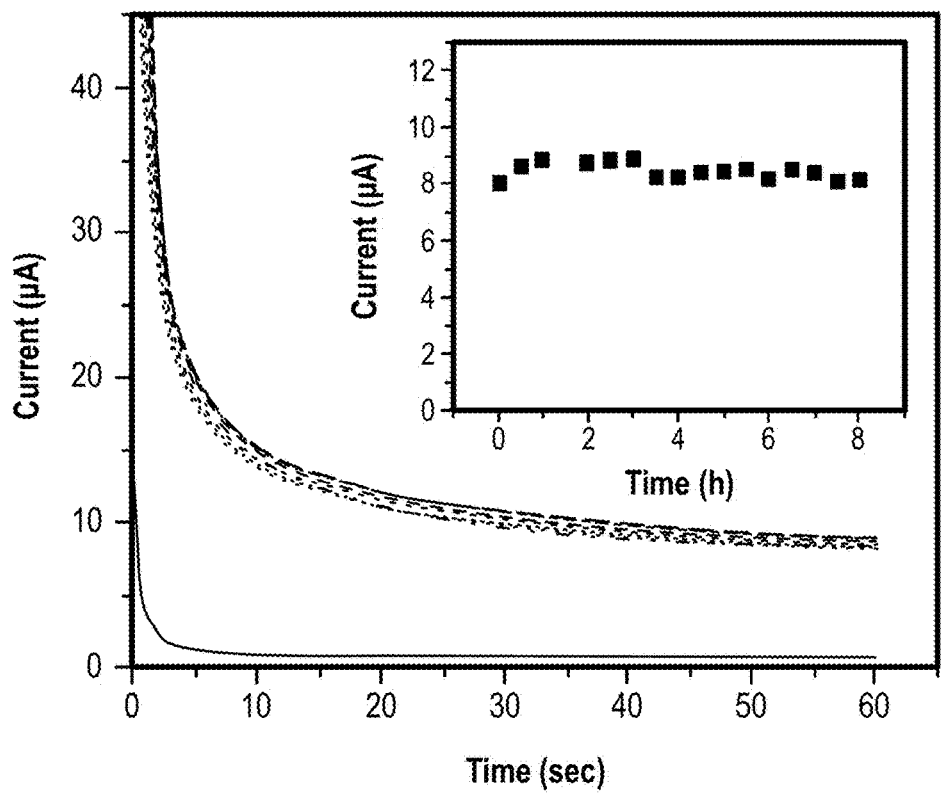
FIG. 43A shows a data plot showing the stability of an exemplary lactate T3 electrochemical sensor.

For example, a person can apply an exemplary lactate T3 sensor of the disclosed technology to the epidermis and continuously monitor the health status. For such uses, the lactate T3 sensors can provide stable reproducible signals at room temperature during long periods of operations. The stability of the lactate T3 sensors may depend on the stability of the enzyme. To evaluate this, a time dependent analysis of an exemplary lactate T3 sensor device was performed in which the response of the tattoo was recorded. FIG. 43A shows a data plot showing the stability of an exemplary lactate T3 electrochemical sensor. The inset plot shows the corresponding current-time data of the amperometric responses. The data plot of FIG. 43A shows that the exemplary sensor provided reproducible results (e.g., RSD=3.6%), which underscores its applicability for long term epidermal use.

Figure 43B:
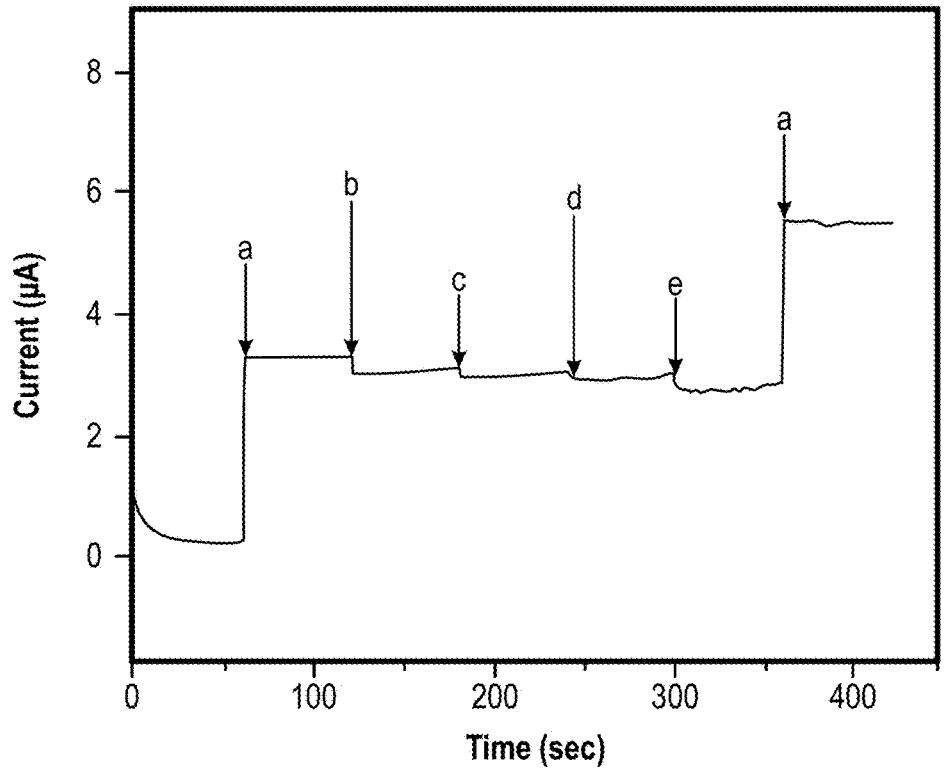
FIG. 43B shows a data plot of an interference implementation with (a) 4 mM L-lactate, (b) 84 μM creatinine, (c) 10 μM ascorbic acid, (d) 0.17 mM glucose and (e) 59 μM uric acid.

In addition, for example, the human sweat includes several metabolites and electrolytes. Out of these, creatinine, ascorbic acid, glucose and uric acid can affect the response of the exemplary enzymatic T3 sensors. An exemplary lactate T3 sensor device was implemented in presence of these exemplary interferents at physiological concentrations. FIG. 43B shows a data plot of an interference implementation with (a) 4 mM L-lactate, (b) 84 μM creatinine, (c) 10 μM ascorbic acid, (d) 0.17 mM glucose and (e) 59 μM uric acid. As shown in the data plot of FIG. 43B, the exemplary interferents exhibited minimal effect on the response due to lactate with signal deviation not more than 6% for each of the interferents.

For example, the human epidermis regularly experiences deformations due to bodily movements. Such epidermal deformations are a major cause of concern for wearable devices in which the devices undergo disfigurations similar to the skin. This can be true for epidermal electronics since these go directly on the human skin. As the human body moves, the skin can undergo bending, stretching and twisting stress. Mechanical strain can lead to increased surface area of printed wearable devices. The amperometric response is a function of the electrode area. Varying electrode area affects the sensor signal and can lead to undesired results.

Figure 44A:
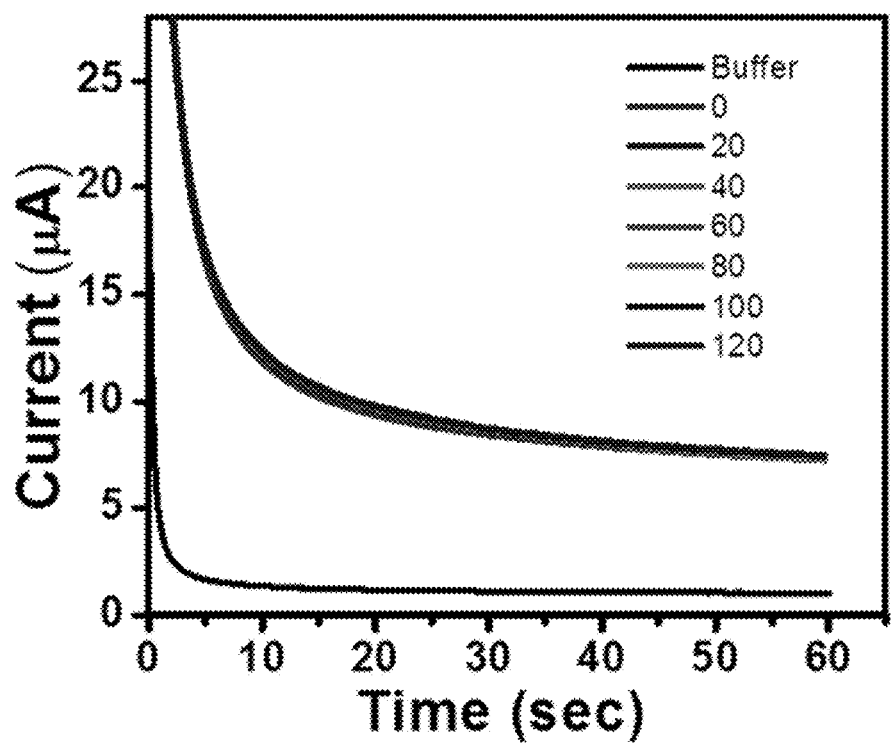
FIGS. 44A-44D show data plots of the electrochemical responses of an exemplary lactate T3 sensor transferred on a flexible GORE-TEX textile undergoing repeated bending (FIG. 44A) and stretching (FIG. 44C), with their normalized current plots (FIGS. 44B and 44D, respectively).
Figure 44B:
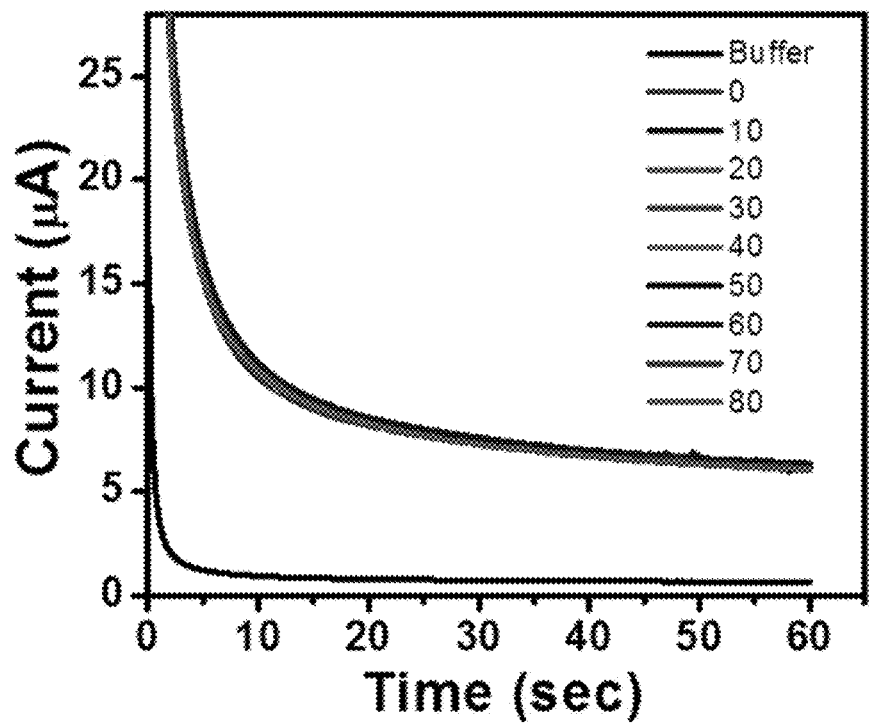
Figure 44C:
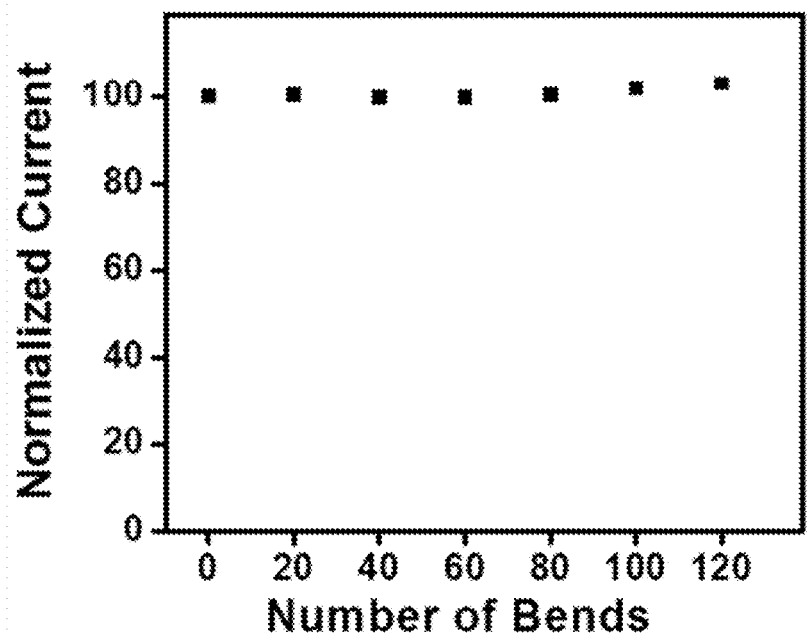
Figure 44D:
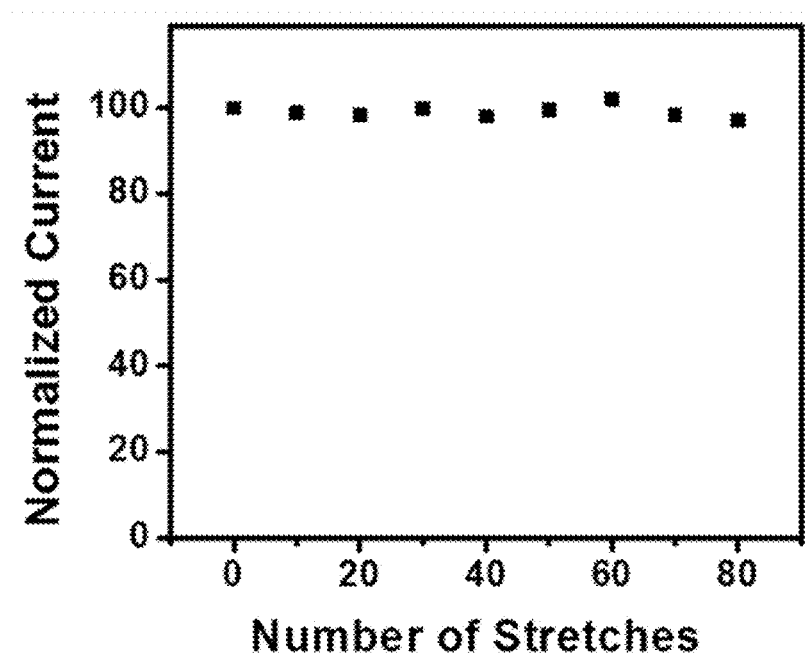

Exemplary implementations were performed to evaluate the mechanical resiliency of the exemplary lactate T3 electrochemical sensor devices. The robustness of the exemplary T3 sensor was implemented by applying it to GORE-TEX and bending it for 120 times by 90° while the sensor response was recorded after every 20 bending iterations. This was followed by stretching the same tattoo by 10% for a total of 80 times with data recorded every 10 stretching iterations. Each bending/stretching cycle included bending/stretching for 5 s followed by relaxation of another 5 s. FIGS. 44A-44D show data plots of the electrochemical responses of an exemplary lactate T3 sensor transferred on a flexible GORE-TEX textile undergoing repeated bending (FIG. 44A) and stretching (FIG. 44C), with their normalized current plots (FIGS. 44B and 44D, respectively). As demonstrated by the data in the data plots of FIGS. 44A-44D, the response of the exemplary lactate T3 sensor in each mechanical stress implementation remained substantially stable with an exemplary R.S.D. of 1.24% and 1.50% during bending and stretching, respectively. For example, the minimal deviation of the exemplary sensor response even after subjecting it to large number of stress cycles may be attributed to two reasons, e.g., (i) the carbon fiber dispersed in the carbon and Ag/AgCl inks and the MWNTs drop casted on the printed T3 sensor may enhance the resiliency of the tattoos towards mechanical deformations while providing electrical connectivity and (ii) the transparent insulator covering majority of the exemplary T3 sensor surface area may further help in avoiding crack developments within the device. Therefore, the disclosed enzymatic T3 sensors are a capable of performing desirably under various strains and thus serve as a compelling epidermal sensing platform.

Figure 45:
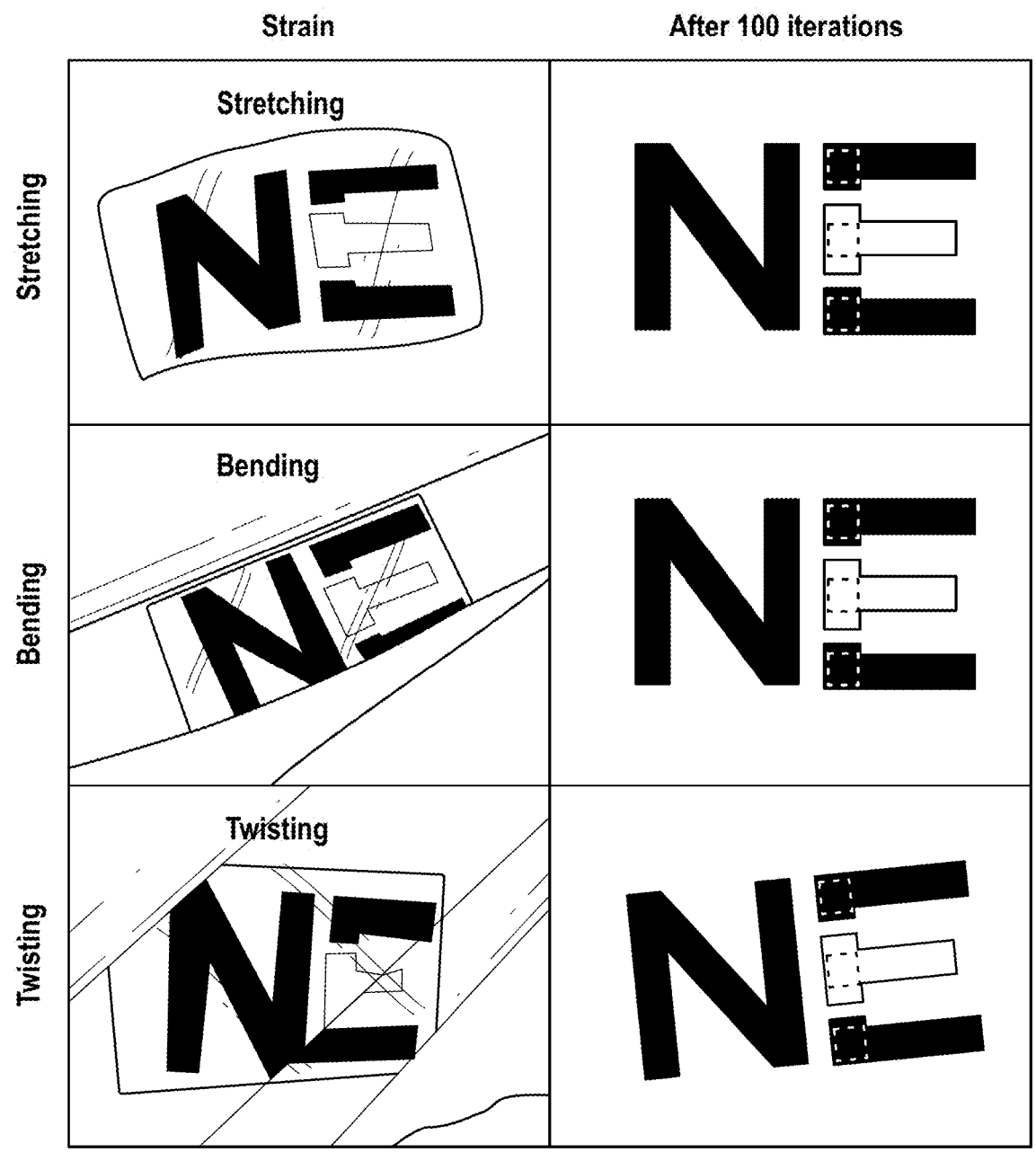
FIG. 45 shows images of exemplary lactate T3 sensors on human skin on the neck under mechanical strain including stretching (top row), bending (middle row), and twisting (bottom row) endured by a bare 'NE' tattoo during and subsequent to 100 stretching, bending, and twisting iterations (shown in the right column of images).

FIG. 45 shows images of exemplary lactate T3 sensors on human skin on the neck under mechanical strain including stretching (top row), bending (middle row), and twisting (bottom row) endured by a bare 'NE' tattoo during and subsequent to 100 stretching, bending, and twisting iterations (shown in the right column of images). The exemplary images demonstrate that the T3 sensors are quite resilient to such flexions.

The disclosed epidermal lactate T3 sensors can be implemented for real-time, online monitoring of the lactate concentration during human exercise. Examples of screen-printed temploraryt transfer tattoo lactate sensors were modified with LOx for the oxidation of sweat lactate and MWNTs/TTF to enhance transduction, which were used in various in vitro and on-body implementations. In the exemplary in vitro implementatoins, the exemplary enzymatic T3 sensors exhibited a wide linear range up to 20 mM with a high sensitivity of 644.2 nA/mM. The exemplary enzymatic T3 sensors also showed specific selectivity toward lactate, e.g., demonstrated in exemplary implementations that included adding several interfering metabolites common in sweat. In addition, for example, the electrochemical performance of the exemplary enzymatic T3 sensors was shown to be consistent with bending and stretching the tattoos transferred on GORE-TEX and human skin located at the neck. Exemplary results showed that the exemplary enzymatic T3 sensors can provide real-time sweat lactate concentration patterns.

In another aspect of the disclosed technology, the disclosed epidermal electrochemical sensors can be included with epidermal biofuel cells to form an on-body, wearable complete self-powering monitoring system.

Examples of the epidermal printed biofuel cells including methods, systems, and devices are described in the PCT Patent Application document, entitled "PRINTED BIOFUEL CELLS", filed Nov. 30, 2012, which is incorporated by reference in its entirety as part of the disclosure in this patent document.

Exemplary implementations of the printed biofuel cells and methods to fabricate them are described in this patent document.

The disclosed technology includes wearable epidermal biofuel cell devices to provide continuous power generation while worn on a human or other user. In some implementations, the exemplary wearable biofuel cell device can be applied to the wearer's epidermis as a temporary-transfer tattoo and is able to scavenge an ample supply of the biofuel L-lactic acid found in the wearer's perspiration in order to generate power. In this exemplary device, the electrodes of the wearable epidermal biofuel cell can be functionalized with lactate oxidase and platinum black within the anode and cathode, respectively, to achieve the power generating operation. Exemplary implementations of the exemplary wearable epidermal biofuel cell were performed to demonstrate the application of various forms of mechanical deformation relevant to practical epidermal applications, which resulted in minimal effects on the performance of the device. For example, an exemplary implementation of the epidermal tattoo biofuel cell device during a controlled fitness routine revealed a maximum power density of 68 $\mu W\ cm^{-2}$ was obtained, hence realizing power production from human perspiration. The epidermal bioenergy paradigm thus holds noteworthy potential for use in the fitness, sport, athletics, performance, and generalized healthcare monitoring domains.

As the cost of personal health monitoring continues to rise, the fitness and healthcare industries have become increasingly reliant on wearable sensors to quantify various physiological metrics in a non-intrusive, user-friendly, and cost-effective fashion to reduce such costs. For example, for epidermal biosensing applications, durability, light-weight, and intimate skin conformance are core requirements of such sensor devices to assess vital signs, e.g., such as heart rate, respiration rate, oxygenation of the blood, skin temperature, bodily motion, brain activity, and blood pressure, as well as chemical sensors capable of monitoring various physiological analytes on the wearer's epidermis as well as chemical agents in their local vicinity. For example, these conformal electronic and diagnostic technologies have advanced considerably to the point of integration of disparate systems on a single skin-adhesive substrate. However, further progress in this arena has been hindered by the lack of wearable and conformal power sources, especially those able to harness the mechanical or chemical energy produced by the wearer's body. While flexible and thin battery technologies have been developed, toxicity, longevity, device weight, and overall poor operational performance have precluded their use in transdermal applications, as well as the rigorous mechanical deformation encountered during bouts of physical activity remains to be addressed with respect to these devices. Additionally, piezoelectric energy harvesting materials have also been plagued by the low efficiencies associated with the electromechanical interconversion process in crystalline media lacking inversion symmetry. The disclosed wearable epidermal biofuel cell technology can be implemented to circumvent these challenges with conventional power sources and provide continuous extraction of biochemical fuels from the wearer's epidermis, which can further enable the development of epidermal electronics that can be utilized in the field.

Exemplary implementations of exemplary wearable epidermal biofuel cell devices were performed that demonstrated the ability to generate useful levels of power from the perspiration of live subjects in a non-invasive and continuous fashion through the use of temporary-transfer tattoos. In some implementations, this was accomplished via the selective oxidation of lactate present in the wearer's perspiration through the inclusion of the enzyme lactate oxidase in the anode matrix in conjunction with the water-insoluble electrochemical mediator tetrathiafulvalene (TTF). For example, lactic acid is the most abundant molecular constituent of the perspiration and is also a widely-recognized indicator of exercise intensity, muscular exertion, fatigue, and aerobic/anaerobic respiration. Charting lactate levels in real-time can thus yield timely information regarding an individual's metabolic response to a fitness routine, hence enabling the individual, trainer, coach, and/or healthcare provider to quantify performance levels. Advantageously, an individual's fitness levels and aerobic capacity can indirectly be inferred by the amount of current (and hence power density) produced by the device.

The disclosed tattoo biofuel cell devices address the requirements imparted by epidermal wear, e.g., including, but not limited to, the ability of the device to maintain its structural and electrochemical resiliency against repeated (and often severe) mechanical deformation such as sheer stress and strain. For example, the exemplary tattoo biofuel cell devices can include dispersed carbon fibers within the ink used to print the anode and cathode electrodes, multi-walled carbon nanotubes incorporated in the electrode contingents to facilitate electron transfer, as well as the immobilization of the catalyst (e.g., lactate oxidase) entrapped in a biocompatible chitosan membrane, which synergistically results in the fabrication of biofuel cells that are largely impervious to mechanical strain, stress, and degradation associated with epidermal wear. For example, operation of the exemplary tattoo biofuel cell devices can produce a redox current from the direct oxidation of lactate within the perspiration via biocatalysis at the anode (and concomitant catalytic reduction of oxygen at the cathode) to generate electrical energy at a load. As such, the disclosed tattoo biofuel cell devices can be implemented in a number of practical applications to satisfy the energy requirements of epidermal, transdermal, and percutaneous devices.

Exemplary materials and methods to implement the disclosed embodiment of the technology are presented. The following chemicals and reagents were used in the described implementations, which included tetrathiafulvalene (TTF), glutaraldehyde solution (8%), chitosan, Pt black, bovine serum albumin (BSA), lactic acid, glucose, potassium phosphate monobasic ($KH_2PO4$), potassium phosphate dibasic ($K_2HPO_4$), hydrochloric acid (HCl), ammonium hydroxide ($NH_4OH$), sodium chloride (NaCl), potassium chloride (KCl), calcium chloride (CaCl$_2$), magnesium chloride (MgCl$_2$), and sodium bicarbonate (NaHCO$_3$). Lactate oxidase (LOx) and carboxy-functionalized multi-walled carbon nanotubes (MWNTs-COOH) were obtained for use in the exemplary implementations. Exemplary reagents were used without further purification. Carbon fibers (e.g., 8 µm diameter, 6.4 mm length, 93% purity) were obtained and further processed to reduce their length to approximately 2 mm.

The fabrication of the exemplary tattoo biofuel cells used in the described implementations included the following processes and procedures, which were utilized in exemplary demonstrations and implementations of the disclosed embodiment under exemplary conditions disclosed herein. Design of the temporary transfer tattoo pattern was accomplished in AutoCAD (Autodesk, San Rafael, Calif.) and fabricated on 75 µm-thick stainless steel through-hole and mesh stencils (Metal Etch Services, San Marcos, Calif.). Unique stencil patterns were used for each layer printed. Chopped carbon fibers were dispersed within a conductive carbon (E3449) ink to increase the tensile strength of the electrode. Printing was performed using an MPM-SPM semi-automatic screen printer (Speedline Technologies, Franklin, Mass.). Blank temporary transfer tattoo paper and the accompanying adhesive substrate were used.

Figure 46:
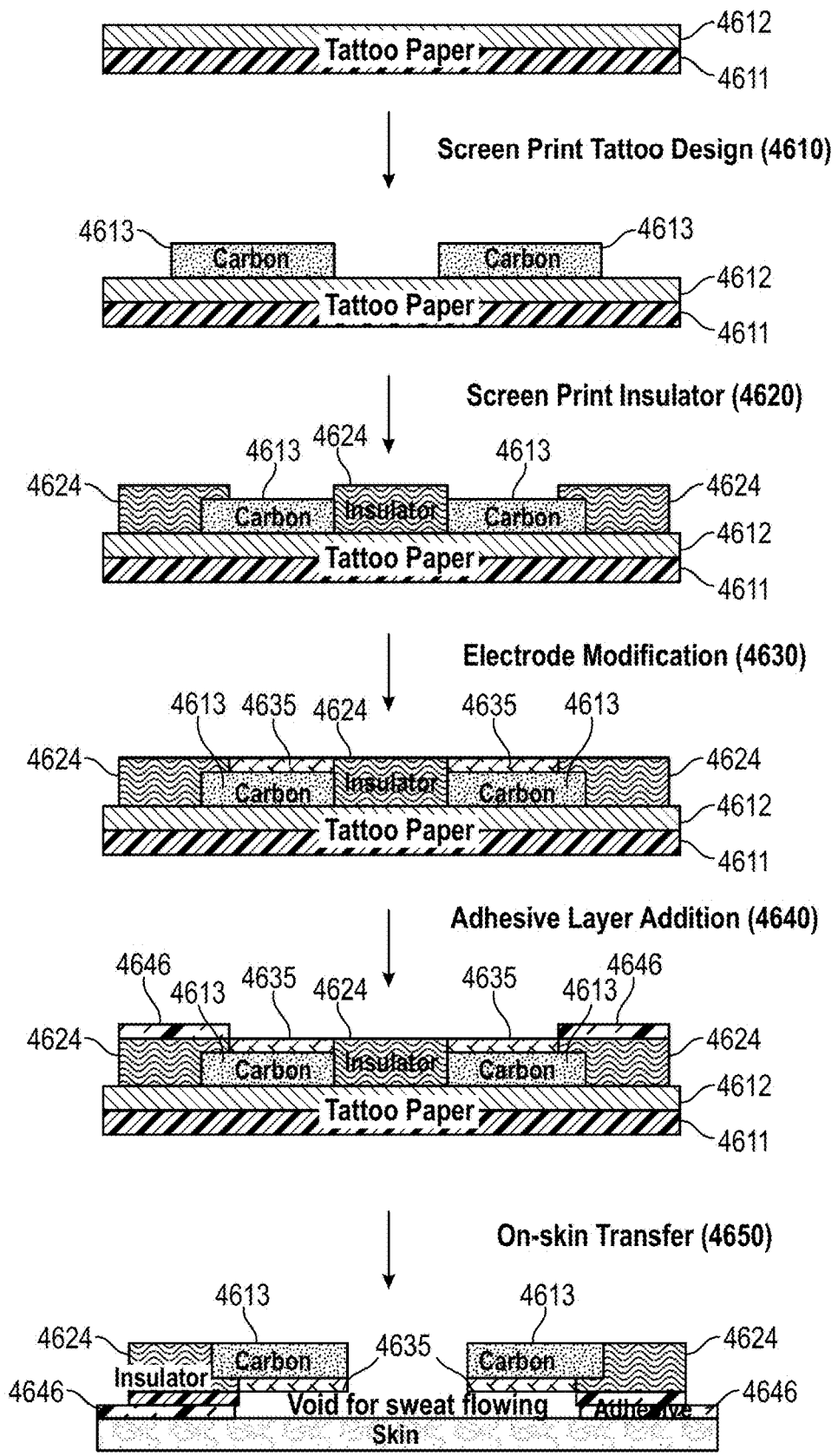
FIG. 46 shows a schematic illustration of an exemplary method to fabricate tattoo biofuel cells using screen printing techniques.

FIG. 46 shows a schematic illustration of an exemplary method to fabricate tattoo biofuel cells using screen printing techniques. The fabrication method includes a process 4610 to deposit electrodes 4613 on a tattoo paper substrate comprising a release agent 4612 coated on a base paper 4611. For example, the release agent 4612 can include hydrophobic material that releases upon exposure moisture, e.g., such as polydimethylsiloxane (PDMS), a cellulosic-based material, a silicone material, among others. For example, the electrodes 4613 can formed by screen printing, roll-to-roll printing, aerosol deposition, inkjet printing, or other printing techniques to fabricate a printed anode and cathode of the tattoo biofuel cell device. The electrodes 4613 can be formed of a carbon-based ink material or other electrically conductive material, which can include a catalyst, e.g., including, but not limited to, an enzyme biocatalyst or noble metal catalyst, dispersed within the ink. Implementation of the process 4610 to deposit the electrodes 4613 can also include the formation of interconnects, contact pads, or other electrical components of the tattoo biofuel cell device. The process 4610 can include a curing procedure to thermally or UV cure the electrodes 1613 on the tattoo paper substrate material. In some implementations, the process 4610 can include the deposition and curing of an underlayer of an electrically conductive material, which can include the interconnects, contact pads, or other electrical components of the tattoo biofuel cell device. The fabrication method includes a process 4620 to deposit a layer of a transparent insulator material 4624 on the tattoo paper substrate exposing the electrodes 4613. The fabrication method includes a process 4630 to modify the electrodes 4613 with a biochemical modifier 4635. In some implementations, the process 4630 can include attaching the catalyst as the biochemical modifier 4635 to the anode and/or cathode by coating the catalyst as a layer on the surface of the anode and/or cathode electrode; by entrapping the catalyst in an electropolymerized conducting polymer formed on the surface of the anode and/or cathode electrode; by entrapping the catalyst using a selectively permeable scaffold-like structure, e.g., such as an electro-permeable membrane, formed on the surface of the anode and/or cathode electrode; by covalently bonding the catalyst to the surface of the anode and/or cathode electrode; or by electrostatically anchoring the catalyst to the surface of the anode and/or cathode electrode. In some implementations, the process 4630 can include attaching an electroactive mediator as the biochemical modifier 4635, in addition to or alternatively to the catalyst, to the anode and/or cathode electrode using any of the described techniques. The fabrication method includes a process 4640 to deposit an adhesive layer of an adhesive material 4646 over at least a portion of the transparent insulator material 4624 on the tattoo paper substrate, e.g., still exposing the electrodes 4613, to produce the tattoo biofuel cell device ready for implementation and wearable on a user's body. For example, subsequent to the fabrication method, the tattoo biofuel cell device can be attached to a user in an on-skin transfer process 4650, in which the adhesive layer is directly attached to the skin and the tattoo paper substrate is peeled off of the device by removing the release agent 4612 (e.g., which also removes the base paper 4611). For example, in some implementations, the fabricated tattoo biofuel cell device can include a void region to permit sweat or other substance including the biofuel to flow.

The two electrode constituents of the tattoo biofuel cell were designed in the shape of 'UC' (acronym for the University of California). As shown in FIG. 46, the entire contingent was printed on the tattoo base paper using carbon fiber-reinforced (1.5% wt.) carbon ink via the thick-film screen printing fabrication process utilizing the stencil set. This was followed by the screen printing of a transparent insulator (Dupont 5036, Wilmington, Del.) on top of the carbon electrodes. The stencil employed for the transparent insulator ink was designed to insulate all but the active areas of the two electrodes. Following every screen printing step, the printed tattoo paper was cured at 90° C. for 15 min in a convection oven.

Following the fabrication of the tattoo BFC, the anode ('U') was modified with LOx while the electrode 'C' was functionalized with Pt black to serve as the cathode. With respect to the bioanode modification, a suspension of carbon nanotubes in ethanol (5 mg/mL) was sonicated for several hours, and then mixed with 0.1 M TTF ethanol/acetone solution in a 2.0:1.6 volume ratio. The suspension was subsequently cast onto the open area of the anode. After the electrodes completely desiccated, 5 µL LOx solution (40 mg/mL with 10 mg/mL BSA) was cast on the electrode, and then covered with 2 µL of 1 wt % chitosan solution. The electrodes were then cross-linked with glutaraldehyde vapor and stored at 4° C. overnight. To modify the tattoo BFC cathode, an aqueous solution of 10 mg/mL Pt black was sonicated and 10 µL of the suspension was cast on the electrode. Following complete desiccation, 1 µL Nafion solution (5 wt %) was cast on the electrode to act as a protective layer.

As illustrated in FIG. 46, in order to transfer the tattoos to a substrate, a transparent adhesive sheet was first applied to the tattoo paper, which ensured that the tattoo adhered satisfactorily to the body/substrate. A rectangular region was excised from the adhesive sheet such that the active anode and cathode areas remained unobstructed to enable the facile diffusion of lactate and oxygen to the respective electrode contingents. In order to apply the adhesive layer to the substrate, one of the transparent protective sheets from the adhesive sheet was removed and the adhesive layer was first mated with plain tattoo base paper. Later, the second transparent protective sheet mated with the adhesive sheet was removed to expose the adhesive layer. A void was also left between the anode and cathode contingents to facilitate the flow of perspiration between these two components. Next, the tattoo contingent was applied to the substrate, the base paper was dabbed with water to dissolve the release agent, and the wet base paper was gently removed to expose the adhesive layer on the substrate. The tattoo BFC was finally placed on the adhesive sheet already located on the substrate and removed by dabbing it with water and gently peeling the base paper from the substrate.

In one exemplary embodiment of the disclosed tattoo biofuel cell device, an epidermal biofuel cell device includes a substrate formed of a flexible electrically insulative material structured to adhere to the skin of a user, an anode formed on the substrate of an electrically conductive material, the anode including a catalyst to facilitate the conversion of a fuel substance in a biological fluid to a first product in an oxidative process that releases electrons captured at the anode, thereby extracting energy from the fuel substance, a cathode configured on the substrate adjacent to the anode and separated from the anode by a spacing region, the cathode formed of a material that is electrically conductive and capable of reducing an oxygenated substance in the biological fluid to a second product in a chemical reduction process in which the second product gains electrons, and an anode electrode interface component and a cathode electrode interface component formed on the substrate and electrically coupled to the anode and the cathode, respectively, via electrical interconnects, in which the extracted energy is addressable as electrical energy at the anode electrode interface component and the cathode electrode interface component.

Exemplary implementations of the exemplary tattoo biofuel cell device were performed to perfect the device with regards to the electrochemical performance in vitro. For example, the tattoo biofuel cells were first evaluated by transferring the pattern onto a rigid plastic substrate or onto a flexible GORE-TEX textile for mechanical integrity studies. For example, 0.2 M McIlvaine buffer (pH 5.5) was utilized to emulate the average pH value of human perspiration. With respect to in vitro stability evaluation, artificial perspiration was prepared with the following electrolytes, metabolites, and small molecules, e.g., including $Na_2SO_4$, $NaHCO_3$, $KCl$, $MgCl_2$, $NaH_2PO_4$, $CaCl_2$, acetic acid, lactic acid, pyruvic acid, glucose, uric acid, urea, creatinine and ascorbic acid. The pH of the artificial perspiration stock solution was adjusted to 5.3 by 5 M $NH_4OH$. The exemplary solutions were prepared with ultra-pure water (18.2 $M\Omega \cdot cm$). Electrochemical characterization was performed at room temperature leveraging a CH Instruments (Austin, Tex.) model 1232A potentiostat.

Healthy volunteer subjects participated in the exemplary power generation experiments. Each volunteer was instructed to wear a temporary transfer tattoo BFC on their upper bicep in order to assess real-time power generation. The BFC was connected to an external 100 k$\Omega$ load resistor ($R_L$) in order to achieve maximum power transfer. This value was selected to most closely match the internal series resistance ($R_s$) such that the maximum power transfer condition was satisfied ($R_s=R_L$). Electrical current was recorded every 5 s using a Keithley (Cleveland, Ohio) 6514 system electrometer interfaced with a computer system including at least a processor and a memory unit including a control program (e.g., instructions in Matlab) to continuously process acquired current readings via the GPIB interface and interpolated the concomitant power generated per unit area ($P_{DENSITY}=I^2 R_L/A_E$, $A_E=0.06$ cm$^2$). In order to filter extraneous noise, a 10-point moving average was iterated at each data point. For example, the subjects were instructed to mount a stationary cycle and a heart rate (HR) monitor was employed to track the subjects' HR. Subjects were instructed to begin cycling at a steady, slow cadence for 3 min. Following this 'warm-up' period, subjects were instructed to cycle at an increasing pace until 80% of their maximum heart rate was achieved in order to ensure that the anaerobic respiration threshold was attained, hence augmenting the excretion of lactic acid in the perspiration Immediately following the subjects' transition to the anaerobic regime, the subjects were instructed to maintain their current cadence for 15 min in order to observe the temporal evolution of the lactate level. Following the 15 min intense exercise activity, subjects were instructed to gradually reduce their cadence during a 3 min 'cool-down' period. The volunteers ingested no fluid (dehydrated state) prior to and during the duration of the fitness routine.

Figure 47:
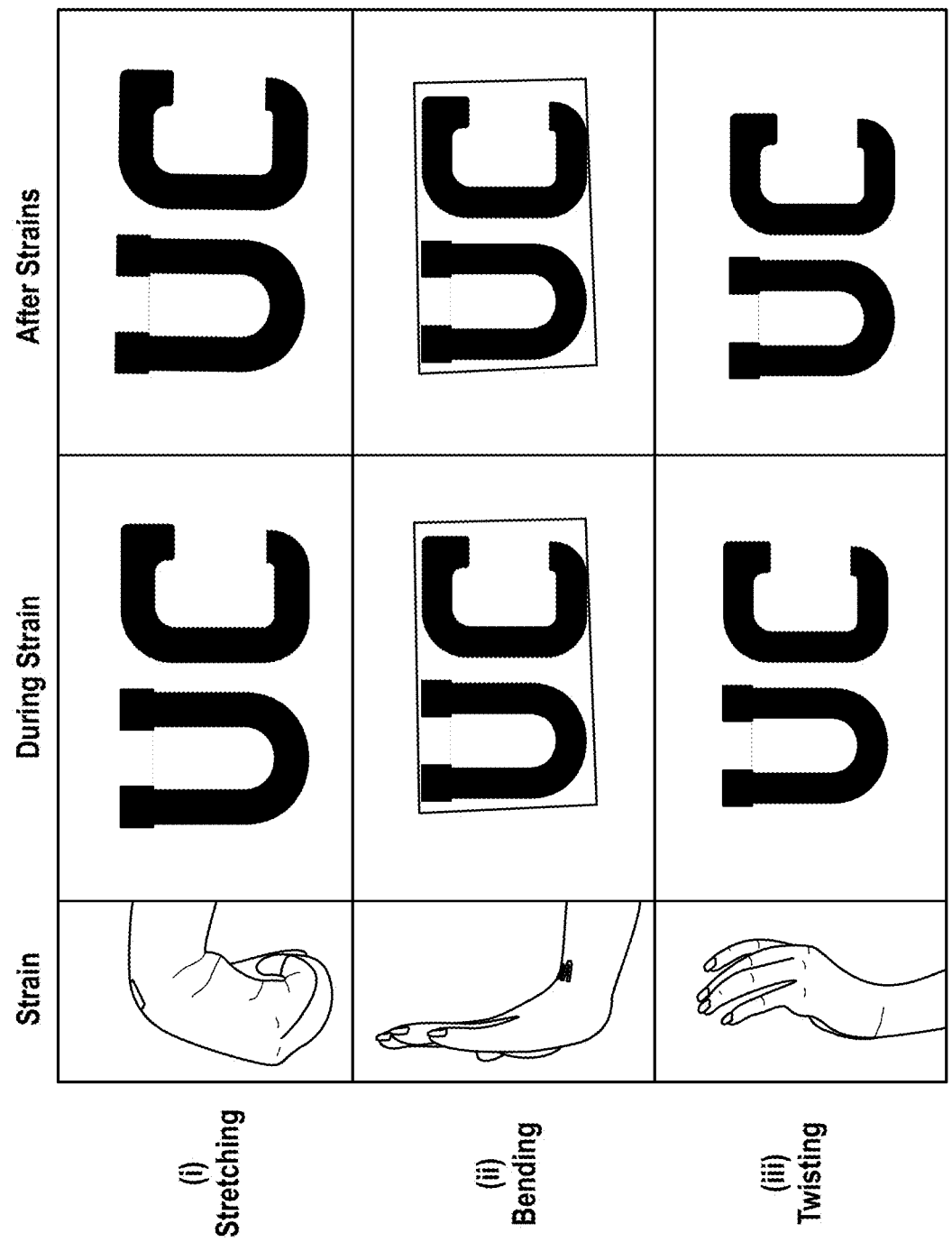
FIG. 47 shows images of the epidermal tattoo biofuel cells during mechanical stress caused by continuous body movements including (i) stretching, (ii) bending, and (iii) twisting.

Exemplary implementations of exemplary wearable epidermal biofuel cell devices were performed that demonstrated resiliency against mechanical stress caused by continuous body movements. For example, the longevity of such epidermal-mounted devices depend greatly on their ability to adhere well to the human skin without developing fractures that damage the devices. The most common body movements involve flexions, which typically comprise of bending, stretching, and/or twisting of the epidermal layer. Accordingly, such devices must encompass an intrinsic flexibile and stretchable nature in addition to being able to adhere well to the epidermis. The disclosed tattoo biofuel cell devices include dispersion of carbon fibers within the inks employed to print these devices, which provide a conductive, interleaved backbone that aids in maintaining the electrical conductivity under various biomechanical stressors. Similarly, the use of an adhesive layer firmly attaches the tattoo biofuel cells to the skin. Visual analysis of the tattoo biofuel cell device on the dorsal region of a human wrist under repeating bending, stretching, and twisting dorsiflexion movements was performed for a total of 50 iterations. FIG. 47 shows images of the epidermal tattoo biofuel cells during mechanical stress caused by continuous body movements including (i) stretching, (ii) bending, and (iii) twisting. The left column of image in FIG. 47 provides the side view of dorsal movements; the middle column provides images of the top view of the biofuel cell tattoos during the various deformations; and the right column provides images of the top view of the biofuel cell tattoos at the end of each movement. The images demonstrate that the tattoo biofuel cell devices are quite resilient to flexions that emulate epidermal wear, e.g., as a consequence of the overlying insulator layer, which serves to maintain the structural integrity of the printed carbon layer. Accordingly, the epidermal biofuel cell devices can perform desirably under various strains and thus can serve as a compelling platform for various epidermal applications.

To date, the majority of lactate biofuel cells have been based on the lactate dehydrogenase enzyme. However, in these existing devices, NAD$^+$ must be employed as the cofactor, which represents a noteworthy challenge given that this molecule must be immobilized on the electrode to prevent it from leeching into the matrix while being able to diffuse, with relative ease, to the enzyme's active site.

The disclosed technology includes an exemplary lactate-based biofuel cell utilizing the lactate oxidase (LOx) enzyme for non-invasive power generation from human perspiration, e.g., by selectively catalyzing the oxidation of lactate in the perspiration as the biofuel for epidermal power generation. In some implementations the electrodes of the exemplary tattoo biofuel cell device are functionalized to achieve efficient bioelectrocatalytic conversion, e.g., in which the 'U' of the tattoo (anode) was functionalized with MWNTs/

TTF/LOx, hence serving as the bioanode to catalyze the oxidation of lactate to pyruvate in the presence of oxygen (cofactor). The cathode 'C' made use of a drop-casted Pt black layer, protected with a Nafion proton-exchange membrane.

Figure 48B:
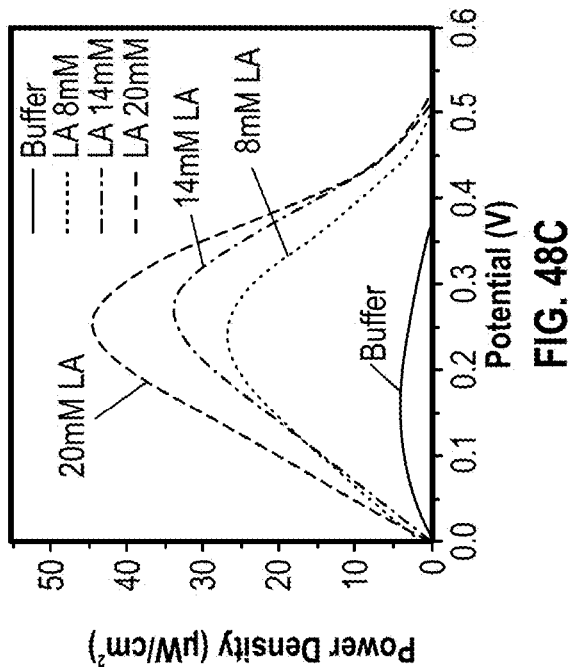
FIG. 48B shows a data plot of polarization curves of the exemplary functionalized MWNTs/TTF/LOx bioanode in the absence of presence of 14 mM lactic acid in 0.2 M McIlvaine buffer solution, pH 5.5, respectively.
Figure 48C:
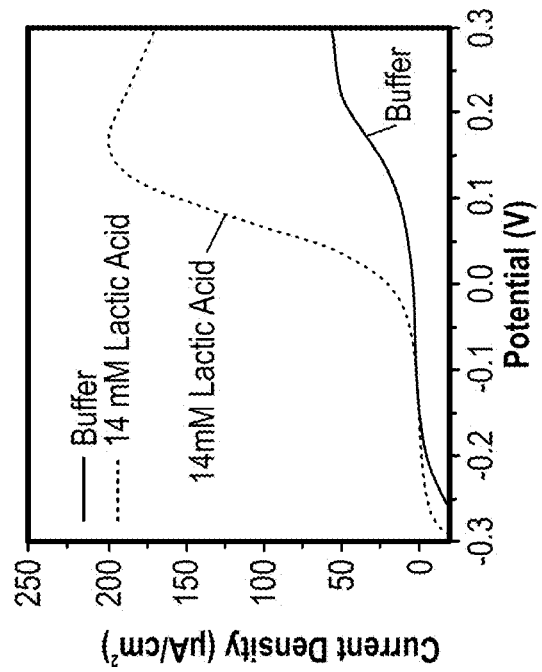
FIG. 48C shows a data plot of power density achieved from the exemplary tattoo biofuel cell device with different lactic acid concentrations.
Figure 48A:
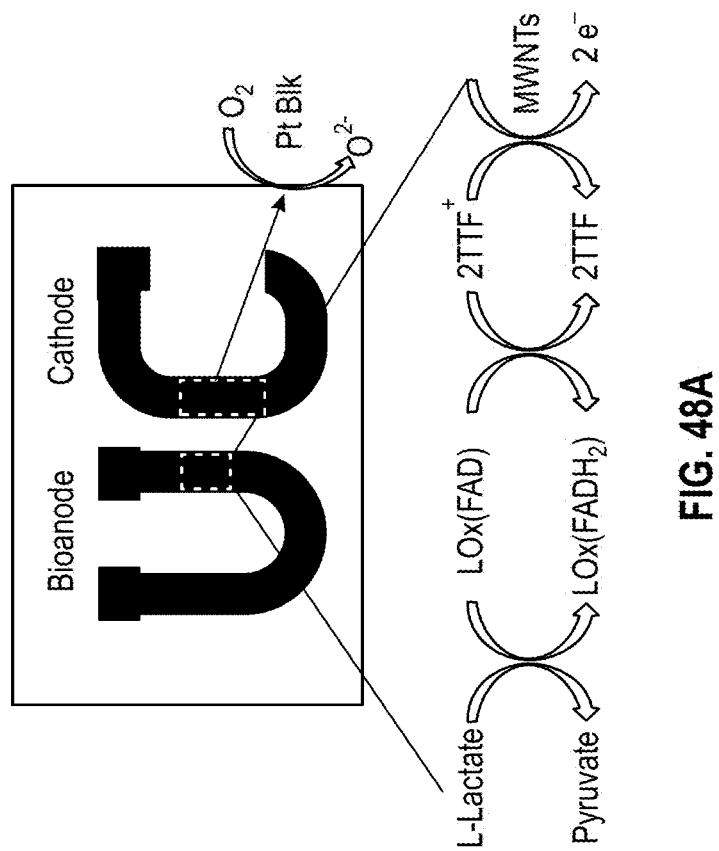
FIG. 48A shows an image of the exemplary functionalized device.

An image of the exemplary functionalized device is shown in FIG. 48A. The bioanode of the exemplary tattoo biofuel cell device was functionalized with the mediator TTF and MWNTs. This bioanode was then covered with a layer of chitosan, e.g., a naturally-derived biopolymer well-known for its biocompatibility. For example, chitosan not only serves to protect the modified enzyme electrode, but it also functions as a physical barrier to limit the efflux of the biocatalytic backbone from the tattoo and onto the underlying substrate.

FIG. 48B shows a data plot of polarization curves of the exemplary functionalized MWNTs/TTF/LOx bioanode in the absence of presence of 14 mM lactic acid in 0.2 M McIlvaine buffer solution, pH 5.5, respectively. The electrocatalytic activity of the MWNTs/TTF/LOx bioanode was determined in vitro with an external Ag/AgCl (1 M KCl) electrode and a Pt wire counter electrode. Polarization curves were recorded by applying linear sweep voltammetry with a scan rate of 1 mV/s in McIlvaine buffer pH 5.5 with 14 mM lactic acid, and normalized by the surface area of the electrode as a function of potential. As shown in FIG. 48B, the TTF-mediated oxidation of lactic acid initiates from around −0.1 V with a peak potential of 0.14 V (vs. Ag/AgCl), indicating that the MWNTs/TTF/LOx exhibits selective catalytic ability towards the oxidation of lactic acid, and hence serves as a suitable bioelectrocatalytic cascade for the bioanode constituent of the BFC. For example, TTF can be used a selective mediator to aid in electron transfer between the LOx active site and the electrode surface. Other mediators, e.g., including, but not limited to, derivatives of ferrocene and Meldola's blue, can also be used as the selective mediator of the bioanode. It is noted that although able to mediate the electro-oxidation of lactic acid, these other small-molecule mediators are water-soluble, and the oxidation current obtained may be decayed as a consequence of the leaching of the mediator. Compared with these mediators, TTF encompasses several noteworthy advantages, namely lower oxidation potential and more stable performance. Also, the incorporation of MWNTs further shifted the lactic acid oxidation onset potential more negatively and further enhanced the oxidation current, which may be due to the electron donor-acceptor interaction between TTF and negatively charged MWNTs, resulting in facilitated electron transfer to the electrode. Therefore, the MWNTs/TTF/LOx cascade is well-suited to serve as the bioanode, and, together with a Pt black cathode, a complete lactic acid biofuel cell can be assembled on the exemplary temporary transfer tattoo substrate.

FIG. 48C shows a data plot of power density achieved from the exemplary tattoo biofuel cell device with different lactic acid concentrations. As shown in the figure, the exemplary tattoo biofuel cell device approached 25 µW cm$^{-2}$ with 8 mM lactic acid (dissolved in buffer), and increased to 34 and 44 µW cm$^{-2}$ with further increased lactic acid concentrations of 14 mM and 20 mM, respectively. A small signal was observed during control experiments (no lactic acid added).

While this patent document contain many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. A non-invasive epidermal electrochemical sensor device, comprising:
   an adhesive membrane;
   a flexible or stretchable substrate disposed over the adhesive membrane;
   an anodic electrode assembly disposed over the flexible or stretchable substrate, the anodic electrode assembly including an iontophoretic electrode;
   a cathodic electrode assembly disposed over the flexible or stretchable substrate and adjacent to the anodic electrode assembly, wherein the cathodic electrode assembly includes an iontophoretic electrode;
   wherein at least one of the anodic electrode assembly or the cathodic electrode assembly include a sensing electrode that includes a working electrode and at least one of a counter electrode or a reference electrode, and wherein the iontophoretic electrode in the anodic electrode assembly or the cathodic electrode assembly that includes the sensing electrode is disposed on the flexible or stretchable substrate to at least partially encompass the working electrode and the at least one of the counter electrode or the reference electrode,
   an electrode interface assembly including independent electrically conductive contacts disposed on the flexible or stretchable substrate and electrically coupled to each electrode of the anodic electrode assembly and the cathodic electrode assembly; and
   wherein the iontophoretic electrodes in the anodic electrode assembly and the cathodic electrode assembly are operable to pass an electrical signal between the iontophoretic electrodes to apply an electric field to drive ion flow from interstitial fluid (ISF) toward the working electrode and the at least one of the counter electrode or the reference electrode,
   wherein the working electrode includes an electrochemical transducer layer including a catalyst to selectively catalyze a corresponding analyte in the ISF to cause a reaction detectable at the anodic and cathodic electrode assemblies, and
   wherein the electrically conductive contacts of the electrode interface assembly are configured to electrically couple to one or more electrical circuitry to transmit a sensor signal indicative of the reaction to detect the analyte, wherein the adhesive membrane includes a silicone membrane, a urethane membrane, or an acrylic adhesive membrane, wherein the adhesive membrane includes a gel layer.

2. The non-invasive epidermal electrochemical sensor device of claim 1, wherein the gel layer includes hydrogel or cryogel.

3. The non-invasive epidermal electrochemical sensor device of claim 1, wherein the gel layer includes a charged chemical agent.

4. The non-invasive epidermal electrochemical sensor device of claim 3, wherein the charged chemical agent includes a chemical agent that enhances extraction of ISF.

5. The non-invasive epidermal electrochemical sensor device of claim 4, wherein the ISF includes biofluid and the chemical agent includes skin permeation enhancers.

6. The non-invasive epidermal electrochemical sensor device of claim 5, wherein the iontophoretic electrodes are configured to pass the electrical signal between the iontophoretic electrodes to apply the electric field to extract ISF to the surface of the skin for detecting chemical analyte in the ISF.

7. The non-invasive epidermal electrochemical sensor device of claim 5, wherein the electrical signal passed between the iontophoretic electrodes include an electrical current.

8. The non-invasive epidermal electrochemical sensor device of claim 5, wherein the electrical current is 0.3 mA/cm2 or less.

9. The non-invasive epidermal electrochemical sensor device of claim 3, wherein the ISF includes biofluid and the charged chemical agent includes sweat inducing chemical agent.

10. The non-invasive epidermal electrochemical sensor device of claim 9, wherein the biofluid includes sweat and the sweat inducing chemical agent includes pilocarpine.

11. The non-invasive epidermal electrochemical sensor device of claim 10, wherein the iontophoretic electrodes are configured to pass the electrical signal between the iontophoretic electrodes to apply the electric field to administer sweat inducing chemical into the skin to locally generate sweat that contains the chemical analyte to be detected.

12. The non-invasive epidermal electrochemical sensor device of claim 10, wherein the electrical signal passed between the iontophoretic electrodes include an electrical current.

13. The non-invasive epidermal electrochemical sensor device of claim 10, wherein the electrical current is 0.3 mA/cm2 or less.

14. The non-invasive epidermal electrochemical sensor device of claim 1, wherein the eel layer is disposed to cover the iontophoretic electrode in the anodic electrode assembly, the iontophoretic electrode in the cathodic electrode assembly, or both of the iontophoretic electrodes in the anodic electrode assembly and the cathodic electrode assembly.

15. The non-invasive epidermal electrochemical sensor device of claim 1, wherein the sensor signal is generated using an amperometric technique, a potentiometric technique, or a voltammetric technique.

16. The non-invasive epidermal electrochemical sensor device of claim 1, wherein the sensor signal is associated with an electrochemical or redox reaction sustained at the anodic and cathodic electrode assemblies.

17. The non-invasive epidermal electrochemical sensor device of claim 1, wherein the electrically conductive contacts of the electrode interface assembly is magnetic to magnetically and electrically couple to the one or more electrical circuitry that are external to the non-invasive epidermal electrochemical sensor device.

18. The non-invasive epidermal electrochemical sensor device of claim 1, wherein the electric circuitry is integrated with the non-invasive epidermal electrochemical sensor device.

19. The non-invasive epidermal electrochemical sensor device of claim 18, wherein the integrated electric circuitry is configured to perform continuous data collection and monitoring.

20. The non-invasive epidermal electrochemical sensor device of claim 18, wherein the integrated electric circuitry includes at least one of a power source, a signal processing circuitry, or a wireless communication circuitry.

21. The non-invasive epidermal electrochemical sensor device of claim 20, wherein the integrated electric circuitry includes the wireless communication circuitry to wirelessly transmit the sensor signal to an external device.

22. The non-invasive epidermal electrochemical sensor device of claim 21, wherein the external device includes a wearable device.

23. The non-invasive epidermal electrochemical sensor device of claim 1, wherein the analyte includes glucose and the catalyst includes a redox mediator.

24. The non-invasive epidermal electrochemical sensor device of claim 23, wherein the redox mediator includes glucose oxidase (GOx) or glucose dehydrogenase (GDH).

25. The non-invasive epidermal electrochemical sensor device of claim 24, wherein the electrochemical transducer layer includes a solution of GOx or GDH and a solution of a biocompatible polymer to immobilize the GOx or GDH in the electrochemical transducer layer.

26. The non-invasive epidermal electrochemical sensor device of claim 25, wherein the biocompatible polymer includes chitosan.

27. The non-invasive epidermal electrochemical sensor device of claim 23, wherein the non-invasive epidermal electrochemical sensor device is operable to extract the glucose from the ISF in a region containing the working electrode and the at least one of the counter electrode or the reference electrode at the cathodic electrode assembly to cause the working electrode of the cathodic electrode assembly to react with the glucose via the redox mediator for selective glucose detection.

28. The non-invasive epidermal electrochemical sensor device of claim 1, wherein the flexible or stretchable substrate includes at least one of paper, silicone polyurethane, plastic, or textile.

29. The non-invasive epidermal electrochemical sensor device of claim 1, wherein the at least one of the counter electrode or the reference electrode and the iontophoretic electrodes include Ag/AgCl electrodes.

30. The non-invasive epidermal electrochemical sensor device of claim 1, wherein the working electrode includes a hydrogen peroxide sensing transducer.

31. The non-invasive epidermal electrochemical sensor device of claim 30, wherein the hydrogen peroxide sensing transducer includes Prussian Blue.

32. The non-invasive epidermal electrochemical sensor device of claim 1, wherein the iontophoretic electrodes are arranged to extract interstitial fluid (ISF) in a region within 10 mm or less of the working electrode and the at least one of the counter electrode or the reference electrode.

33. The non-invasive epidermal electrochemical sensor device of claim 1, including a first insulating layer formed over the anodic electrode assembly and a second insulating layer formed over the cathodic electrode assembly, the first and second insulating layers to confine electrode and contact areas of the device.

* * * * *